(12) United States Patent
Dow et al.

(10) Patent No.: US 6,930,107 B2
(45) Date of Patent: *Aug. 16, 2005

(54) 6-AZAURACIL DERIVATIVES AS THYROID RECEPTOR LIGANDS

(75) Inventors: Robert L. Dow, Waterford, CT (US); Yuan-Ching P. Chiang, East Lyme, CT (US); Kimberly G. Estep, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/763,451

(22) Filed: Jan. 23, 2004

(65) Prior Publication Data

US 2004/0157844 A1 Aug. 12, 2004

Related U.S. Application Data

(63) Continuation of application No. 09/671,668, filed on Sep. 27, 2000, now Pat. No. 6,787,652.
(60) Provisional application No. 60/156,842, filed on Sep. 30, 1999.

(51) Int. Cl.$^7$ .................. C07D 253/075; A61K 31/53; A61P 11/06
(52) U.S. Cl. ....................... 514/242; 544/182
(58) Field of Search ................. 544/182, 242; 514/242

(56) References Cited

U.S. PATENT DOCUMENTS

| | | | | |
|---|---|---|---|---|
| 3,852,289 | A | 12/1974 | Mylari et al. | 260/248 AS |
| 3,882,115 | A | 5/1975 | Mylari | 260/248 AS |
| 3,883,525 | A | 5/1975 | Mylari | 260/248 AS |
| 3,883,527 | A | 5/1975 | Brennan | 260/248 AS |
| 3,883,528 | A | 5/1975 | Mylari | 260/248 AS |
| 3,896,172 | A | 7/1975 | Mylari et al. | 260/578 |
| 3,905,971 | A | 9/1975 | Miller | 260/247.5 C |
| 3,912,723 | A | 10/1975 | Miller | 260/239.7 |
| 4,198,407 | A | 4/1980 | Rosner et al. | 424/249 |
| 4,239,888 | A | 12/1980 | Miller | 544/309 |
| 4,640,917 | A | 2/1987 | Rosner et al. | 514/222 |
| 5,256,631 | A | 10/1993 | Lindner et al. | 504/229 |

FOREIGN PATENT DOCUMENTS

| | | | |
|---|---|---|---|
| CA | 979457 | 12/1975 | 260/248.6 |
| CA | 992538 | 7/1976 | 260/238.1 |
| DE | 2358851 | 6/1974 | C07D/55/06 |
| DE | 2532363 | 2/1977 | |
| EP | 0737672 | 10/1996 | C07C/281/14 |
| WO | WO9418229 | 8/1994 | C07K/5/06 |
| ZA | 917390 | 9/1991 | |

OTHER PUBLICATIONS

Wolft Manfred E. "Burger's Medicinal Chemistry, 5ed, Part 1", John Wiley & Sons, 1995, pp. 975–977.*

Banker, G.S. et al, "Modern Pharmaceutics, 3ed.", Marcel Dekker, New York. 1996, p. 596.*

A. H. Underwood, et al., *Nature*, vol. 324: pp. 425–429 (1986).

B. L. Mylari, et al., J. Med. Chem., 1977, vol. 20, No. 4, 475–483, "Anticoccidial Derivatives of 6–Azauracil. 1. Enhancement of Activity by Benzylation of Nitrogen–1. Observations on the Design of Nucleotide Analogues in Chemotherapy."

M. W. Miller, et al., J. Med. Chem., 1979, vol. 22, No. 12, 1483–1487, "Anticoccidial Derivatives of 6–Azauracil. 2. High Potency and Long Plasma Life of N1–Phenyl Structures[12]".

M. W. Miller, t al., J. M d. Chem., 1980, vol. 23, No. 10, 1083–1087. "Anticoccidial Derivatives of 6–Azauracil. 3. Synthesis, High Activity, and Short Plasma Half–life of 1–Phenyl–6–azauracils Containing Sulfonamide Substituents[1]."

M. W. Miller, et al., J. Med. Chem., 1981, vol. 24, No. 11, 1337–1342, "Anticoccidial Derivatives of 6–Azauracil. 4. A 1000–fold Enhancement of Potency by Phenyl Sulfide and Phenyl Sulfone Side Chains[1]."

(Continued)

*Primary Examiner*—Venkataraman Balasubramanian
(74) *Attorney, Agent, or Firm*—J. Michael Dixon

(57) ABSTRACT

The present invention provides novel compounds of the Formula I

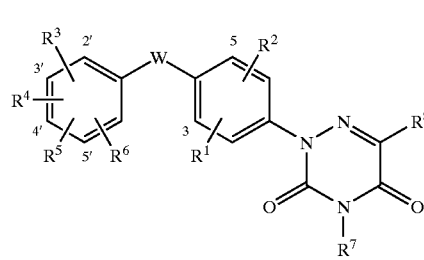

(I)

and prodrugs thereof, geometric and optical isomers thereof, and pharmaceutically acceptable salts of such compounds, prodrugs and isomers, wherein $R^1$ to $R^8$ and W are as described herein. Pharmaceutical compositions containing such compounds, prodrugs, isomers or pharmaceutically acceptable salts thereof, and methods, pharmaceutical compositions and kits for treating obesity, overweight condition, hyperlipidemia, thyroid disease, hypothyroidism, thyroid cancer and related disorders and diseases such as diabetes mellitus, atherosclerosis, hypertension, coronary heart disease, hypercholesteremia, depression, osteoporosis, cardiac arrhythmias, glaucoma and congestive heart failure are also provided.

9 Claims, No Drawings

OTHER PUBLICATIONS

R. D. Carroll, et al., J. Med. Chem., 1983, vol. 26, No. 1, 96–100, "Anticoccidial Derivatives of 6–Azauracil. 5. Potentiation by Benzophenone Side Chains".

K.–B. Rhyu, et al., J. Chem. Inf. Comput. Sci., 1996, vol. 36, No. 3, "A 3D–QSAR Study of Anticoccidial Triazines Using Molecular Shape Analysis."

K.–B. Rhyu, et al. J. Chem. Inf. Comput. Sci., 1995, vol. 35, No. 4, 771–778, "a 3D–QSAR Study of Anticoccidial Triazines Using Molecular Shape Analysis."

A. C. Good, et al., J. Med. Chem., 1993, vol. 36, No. 20, 2929–2937, "QSAR's from Similarity Matrices. Technique Validation and Application in the Comparison of Different Similarity Evaluation Methods."

J. W. McFarland, J. Med. Chem., 1992, vol. 35, No. 14, 2543–2550, "Comparative Molecular Field Analysis of Anticoccidial Triazines".

J. W. McFarland, et al., J. Med. Chem., 1991, vol. 34, No. 6, 1908–1911, "Linear Discriminant and Multiple Regression Analyses of Anticoccidial Triazines".

A. N. Chekhlov, et al., Dokl. Akad. Nauk (1993), 329 (5), 603–7.

N. S. Zefirov, et al., Dokl. Akad. Nauk (1992), 327 (4–6), 504–8.

A. P. Ricketts, et al., Antimicrobial Agents and Chemotherapy, Oct. 1992, vol. 36, pp. 2338–2341, "In Vivo Expression of in Vitro Anticoccidial Activity".

M. J. Lynch, et al., J. Agric. Food. Chem., vol. 25, No. 6, pp. 1344–1353, 1977, "Tissue Residue and Comparative Metabolism Studies on Triazuril in the Chicken, Rat, Dog, and Monkey."

J. F. Ryley, et al., Parasitology (1974), 68, 69–79, "Anticoccidial activity of an azauracil derivative."

* cited by examiner

6-AZAURACIL DERIVATIVES AS THYROID RECEPTOR LIGANDS

CROSS REFERENCE TO RELATED APPLICATION

This application is a continuation of U.S. patent application Ser. No. 09/871,668 filed Sep. 27, 2000, which is now U.S. Pat. No. 6,787,652, which claims the benefit of U.S. Provisional Application Ser. No. 60/156,842, filed Sep. 30, 1999, the contents of each are hereby incorporated by reference.

FIELD OF THE INVENTION

The present invention relates to novel thyroid receptor ligands and, more particularly, relates to novel 6-azauracils, and derivatives thereof, which are useful in the treatment of obesity, overweight condition, hyperlipidemia, thyroid disease, hypothyroidism, thyroid cancer and related disorders and diseases such as diabetes mellitus, atherosclerosis, hypertension, coronary heart disease, hypercholesteremia, depression, osteoporosis, cardiac arrhythmias, glaucoma and congestive heart failure. Also provided are methods, pharmaceutical compositions and kits for treating such diseases and disorders.

BACKGROUND OF THE INVENTION

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid are generally treated with hormone replacement by administering either naturally occurring thyroid hormones or thyromimetic analogues which mimic the effects of thyroid hormones.

Two naturally occurring thyroid hormones, namely, thyroxine or 3,5,3',5'-tetraiodo-L-thyronine (commonly referred to as "$T_4$") and 3,5,3'-triiodo-L-thyronine (commonly referred to as "$T_3$"), are shown below:

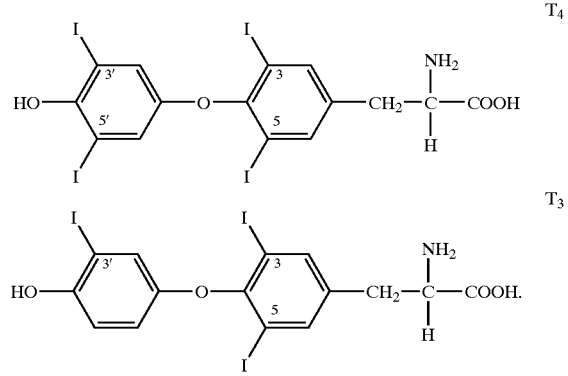

$T_3$ is the more biologically active of the two and, as will be appreciated from the structural formulae provided above, differs from $T_4$ by the absence of the 5' iodine. $T_3$ may be produced directly from the thyroid gland, or, in peripheral tissues, by the removal of the 5' iodine by deiodinase enzymes. Thyromimetic analogs are often designed to be structurally similar to $T_3$. In addition, naturally occurring metabolites of $T_3$ are known.

As discussed above, thyroid hormones affect cardiac functioning, for example, by causing an increase in the heart rate and, accordingly, an increase in oxygen consumption. While the increase in oxygen consumption may result in certain desired metabolic effects, nonetheless, it does place an extra burden on the heart, which in some situations, may give rise to damaging side effects. Therefore, as is known in the art, such as described by A. H. Underwood et al. in an article published in Nature, Vol. 324: pp. 425–429 (1986), efforts have been made to synthesize thyroid hormone analogs which function to lower lipids and serum cholesterol without generating the adverse cardiac effects referred to above.

Certain 6-azauracils and derivatives thereof are known in the art. U.S. Pat. Nos. 3,905,971 and 3,912,723 disclose certain 2-phenyl-as-triazine-3,5(2H,4H)diones and certain 2-substituted-phenyl-as-triazine-3,5(2H,4H) diones and their use as agents for the control of coccidiosis.

U.S. Pat. Nos. 3,883,527 and 3,883,528 disclose processes for producing certain 2-aryl-as-triazine-3,5(2H,4H)-diones, which are useful as coccidiostats.

Canadian Patent Nos. 979457 and 992538 disclose certain 2-phenyl-as-triazine-3,5(2H,4H)diones, derivatives thereof, compositions containing said compounds and process for preparing said compounds, which compounds are useful in controlling coccidiosis.

U.S. Pat. Nos. 3,896,172 and 3,852,289 disclose processes for preparing certain 1,2,4-triazine-3,5(2H,4H)diones having a p-chlorophenylthio-substituted 2-aryl moiety, which compounds are useful as coccidiostats.

U.S. Pat. Nos. 3,882,115 and 3,883,525 disclose processes for preparing certain 1,2,4-triazine-3,5(2H,4H)diones having a 2-aryl moiety which is substituted with, for example, 2-chlorophenoxy and 2-chloro-4-(N-methyl-N-ethylsulfamoyl)phenoxy.

U.S. Pat. No. 5,256,631 and South African Patent No. 91/7390 disclose certain substituted 1,2,4-triazinediones, processes for preparing them and their use as antiprotozoal agents. German Patent No. 25 32 363 discloses certain 1,2,4-triazin-3,5(2H,4H)-dione compounds having a 4-amino-phenoxy-substituted 2-phenyl group. South African Patent No. 73/9126 discloses a process for preparing certain 2-aryl-6-carboxy-1,2,4-triazine-3,5(2H,4H)-diones.

U.S. Pat. No. 4,640,917 discloses substituted 2-phenyl-hexahydro-1,2,4-triazine-3,5-diones which are useful for controlling protozoal diseases. U.S. Pat. No. 4,198,407 discloses certain substituted 2-phenyl-1,2,4-triazine-3,5(2H,4H)-diones and coccidiostatic agents containing them.

Published European Patent Application 0 737 672 discloses a method of producing 1,2,4-triazin-3-one derivatives having a substituent at the 2-position.

U.S. Pat. No. 4,239,888 discloses certain 1-phenyluracils and their utility as coccidiostats.

B. L. Mylari et al., J. Med. Chem. 1977, 20, 475–483; M. W. Miller et al., J. Med. Chem. 1979, 22, 1483–1487; and M. W. Miller et al., J. Med. Chem. 1980, 23, 1083–1087; discloses certain anticoccidial derivatives of 6-azauracil.

M. W. Miller et al., J. Med. Chem. 1981, 24, 1337–1342, discloses certain anticoccidial derivatives of 6-azauracil having phenyl sulfide and phenyl sulfone side chains.

R. D. Carroll et al., J. Med. Chem. 1983, 26, 96–100, discloses certain anticoccidial derivatives of 6-azauracil having a p-benzophenone side chain.

K.-B. Rhyu et al., J. Chem. Inf. Comput. Sci. (1996), 36(3), 620; K.-B. Rhyu et al., J. Chem. Inf. Comput. Sci. (1995), 35(4), 771–8; A. C. Good et al., J. Med. Chem. (1993). 36(20), 2929–37; J. W. McFarland, J. Med. Chem. (1992), 35 (14), 2543–50; and J. W. McFarland et al., J. Med. Chem. (1991). 34 (6), 1908–11; disclose various techniques for studying the quantitative structure-activity relationships among certain anticoccidial 2-(substituted phenyl)-1,2,4-triazine-3,5(2H,4H)-diones.

A. N. Chekhlov et al., Doki. Akad. Nauk (1993), 329 (5), 603–7, discloses the molecular and crystal structure of 2-[3,5-dichloro-4-(m-trifluoromethylphenylthio)phenyl]-1, 2,4-triazine-3,5(2H,4H)-dione.

N. S. Zefirov et al., Dokl. Akad. Nauk (1992), 327 (4–6), 504–8, discloses the quantitative relationship between the structure of 2-substituted 1,2,4-triazine-3,5(2H,4H)-diones and their anticoccidial activity.

A. P. Ricketts et al., Antimicrob. Agents Chemother. (1992), 36 (10), 2338–41, discloses the study of the relationship between the in vitro anticoccidial activity and the in vivo efficacy of compounds such as the aryl triazine compound, 3-chloro-4-[2-chloro-4-(4,5-dihydro-3,5-dioxo-1,2,4-triazin-2(3H)-yl)-6-methylphenoxy]-N-ethyl-N-methyl-benzenesulfonamide.

M. J. Lynch and S. K. Figdor, J. Agric. Food Chem. (1977), 25 (6), 1344–53, disclose tissue residue and comparative metabolism studies on tiazuril, 2-[3,5-dimethyl-4-(4-chlorophenylthio)phenyl-as-triazine-3,5(2H,4H)dione, in the chicken, rat, dog and monkey.

J. F. Ryley et al., Parasitology (1974), 68 (Pt. 1), 69–79, discloses the anticoccidial activity of an azauracil derivative, 2-[3,5-dichloro-4-(4-chlorophenylthio)phenyl-as-triazine-3, 5(2H,4H)dione.

All of the documents cited herein, including the foregoing, are incorporated by reference herein in their entireties.

SUMMARY OF THE INVENTION

The present invention provides compounds of Formula I:

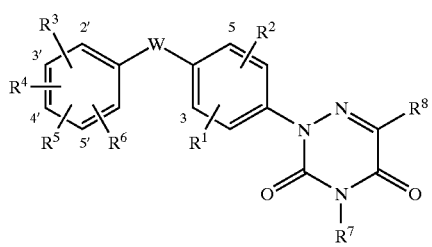

(I)

isomers thereof, prodrugs of said compounds or isomers, or pharmaceutically acceptable salts of said compounds, isomers or prodrugs; wherein W is (a) —O—, (b) —S(O)$_m$—, (c) —NR$^{30}$—, (d) —C(O)—, (e) —HC=CH—, (f) —CH$_2$—, (g) —CHF—, (h) —CF$_2$— or (i) —CH(OH)—;

R$^1$ and R$^2$ are independently (a) hydrogen, (b) halogen, (c) —(C$_1$-C$_6$)alkyl, (d) —CN, (e) —OR$^{12}$ or (f) -trifluoromethyl;

R$^3$ is (a) hydrogen, (b) halogen, (C) —(C$_1$-C$_6$)alkyl optionally substituted with one to three substituents independently selected from the group consisting of halogen, —OCF$_3$ and —CF$_3$, (d) —CN, (e) —OR$^{12}$, (f) -trifluoromethyl, (g) —NO$_2$, (h) —SO$_2$—R$^{13}$, (i) —C(O)$_2$R$^9$, (j) —C(O)NR$^{19}$R$^{20}$, (k) —C(O)R$^{16}$, (l) —NR$^{21}$C(O)—NR$^{21}$R$^{22}$, (m) —NR$^{19}$—C(O)R$^{20}$ or (n) —NR$^{17}$R$^{18}$;

R$^4$ is (a) —C(R$^{14}$)(R$^{15}$)(R$^{16}$), (b) —(C$_0$-C$_3$)alkyl-NR$^{17}$R$^{18}$, (c) —C(O)NR$^{19}$R$^{20}$, (d) —NR$^{19}$—C(O)—R$^{20}$, (e) —(C$_0$-C$_3$)alkyl-NR$^{21}$—C(O)—NR$^{21}$R$^{22}$, (f) —S(O)$_m$—R$^{22}$, (g) —S(O)$_2$—NR$^{21}$R$^{22}$, (h) —NR$^{21}$—S(O)$_2$—R$^{22}$, (i) -aryl, (j) -het, (k) —OR$^{33}$ or (l) halogen; provided that in substituents (f) and (h), R$^{22}$ is other than —OR$^{34}$; and provided that when substituent (b) is —(C$_0$)alkyl-NR$^{17}$R$^{18}$, R$^{18}$ is other than —C(O)—R$^{28}$ or —S(O)$_2$—R$^{29}$;

or R$^3$ and R$^4$ may be taken together to form a carbocyclic ring of Formula —(CH$_2$)$_b$— or a heterocyclic ring selected from the group consisting of -Q-(CH$_2$)$_c$— and —(CH$_2$)$_j$-Q-(CH$_2$)$_k$— wherein Q is O, S or NR$^{25}$; wherein said carbocyclic ring is optionally substituted with one or more substituents independently selected from Group V; and wherein said heterocyclic ring is optionally substituted with one or more substituents independently selected from Group Z;

R$^5$ is —OR$^{23}$;

or R$^4$ and R$^5$ may be taken together to form a heterocyclic ring selected from the group consisting of —CR$^{31}$=CR$^{32}$—NH—, —N=CR$^{31}$—NH—, —CR$^{31}$=CR$^{32}$—O— and —CR$^{31}$=CR$^{32}$—S—;

R$^6$ is (a) hydrogen, (b) halogen, (c) —(C$_1$–C$_6$)alkyl optionally substituted with one to three substituents independently selected from the group consisting of halogen, —OCF$_3$ and —CF$_3$, (d) —CN, (e) —OR$^{12}$, (f) -trifluoromethyl, (g) —NO$_2$, (h) —SO$_2$—R$^{13}$, (i) —C(O)$_2$R$^9$, (j) —C(O)NR$^{19}$R$^{20}$ (k) —C(O)R$^{16}$, (l) —NR$^{21}$C(O)NR$^{21}$R$^{22}$, (m) —NR$^{19}$—C(O)R$^{20}$ or (n) —NR$^{17}$R$^{18}$;

R$^7$ is (a) hydrogen, (b) —(C$_1$–C$_4$)alkyl wherein each carbon atom is optionally substituted with 1 to 3 halo atoms or (c) —(CH$_2$)$_n$COOR$^9$;

R$^8$ is (a) hydrogen, (b) —(C$_1$-C$_6$)alkyl, (c) —C(O)—OR$^9$, (d) —C(O)NR$^{10}$R$^{11}$ or (e) —CN; provided that in substituent (c), R$^9$ is other than methyl or ethyl; and provided that in substitutent (d), R$^{10}$ and R$^{11}$ are not both hydrogen;

R$^9$ is (a) —(C$_1$–C$_{12}$)alkyl optionally substituted with one or more substitutents independently selected from Group V, (b) —(C$_2$–C$_{12}$)alkenyl optionally substituted with phenyl, (c) —(C$_2$–C$_{12}$)dialkenyl, (d) —(C$_3$–C$_{10}$)cycloalkyl, (e) -aryl or (f) -het;

R$^{10}$ and R$^{11}$ are independently (a) hydrogen, (b) —(C$_1$–C$_{12}$)alkyl optionally substituted with one or more substituents independently selected from Group V, (c) —(C$_3$–C$_{10}$)cycloalkyl optionally substituted with one or more substituents independently selected from Group V, (d) —(C$_2$–C$_{12}$)alkenyl or (e) -het;

or R$^{10}$ and R$^{11}$ for any occurrence may be taken together with the nitrogen atom to which are they attached to form het;

R$^{12}$ is (a) hydrogen or (b) —(C$_1$–C$_6$)alkyl wherein each carbon atom is optionally substituted with 1 to 3 fluoro atoms;

R$^{13}$ is (a) —(C$_1$–C$_{12}$)alkyl optionally substituted with one or more substituents independently selected from Group V, (b) —(C$_2$–C$_{12}$)alkenyl, (c) —(C$_3$–C$_{10}$)cycloalkyl, (d) —NR$^{17}$R$^{18}$, (e) -aryl or (f) -het;

R$^{14}$ is (a) hydrogen, (b) —(C$_1$–C$_6$)alkyl or (c) —O—R$^{34}$;

R$^{15}$ is (a) hydrogen or (b) —(C$_1$–C$_6$)alkyl;

or R$^{14}$ and R$^{15}$ are taken together with the carbon atom to which they are attached to form a carbonyl group;

$R^{16}$ is (a) hydrogen, (b) —$(C_1-C_6)$alkyl wherein each carbon atom is optionally substituted with 1 to 3 fluoro atoms, (c) —$(C_0-C_6)$alkyl-$(C_3-C_{10})$cycloalkyl, (d) —$(C_0-C_6)$alkyl-aryl or (e) —$(C_0-C_6)$alkyl-het;

$R^{17}$ is (a) hydrogen, (b) —$(C_1-C_{12})$alkyl optionally substituted with one or more substituents independently selected from Group V, (c) -aryl, (d) -het, (e) —$OR^{34}$ or (f) —$(C_3-C_{10})$cycloalkyl;

$R^{18}$ is (a) hydrogen, (b) —$(C_1-C_{12})$alkyl optionally substituted with one or more substituents independently selected from Group V, (c) -aryl, (d) -het, (e) —$C(O)$—$R^{28}$, (f) —$S(O)_2$—$R^{29}$, (g) —$OR^{34}$ or (h) —$(C_3-C_{10})$cycloalkyl;

or $R^{17}$ and $R^{18}$ for any occurrence are taken together with the nitrogen atom to which they are attached to form het;

$R^{19}$ and $R^{20}$ for each occurrence are independently (a) hydrogen, (b) —$(C_1-C_{12})$alkyl optionally substituted with one or more substituents independently selected from Group V, (c) —$(C_0-C_6)$alkyl-aryl, (d) —$(C_0-C_6)$alkyl-het, (e) —$C(O)$—$NR^{26}R^{27}$, (f) —$C(O)$—$R^{28}$, (g) —$S(O)_2$—$R^{29}$, (h) —$OR^{34}$ or (i) —$(C_3-C_{10})$cycloalkyl;

or $R^{19}$ and $R^{20}$ for any occurrence are taken together with the nitrogen atom to which they are attached to form het;

$R^{21}$ and $R^{22}$ for each occurrence are independently (a) hydrogen, (b) —$(C_1-C_{12})$alkyl optionally substituted with one to three substituents independently selected from Group V, (c) -aryl, (d) -het, (e) —$(C_3-C_{10})$cycloalkyl or (f) —$OR^{34}$;

or $R^{21}$ and $R^{22}$ are taken together with the nitrogen atom to which they are attached to form het;

$R^{23}$ is (a) hydrogen, (b) —$(C_1-C_4)$alkyl optionally substituted with one or more substituents independently selected from Group V or (c) —$C(O)$—$R^{24}$;

$R^{24}$ is (a) hydrogen, (b) —$(C_1-C_{12})$alkyl optionally substituted with one or more substituents independently selected from Group V, (c) —$(C_2-C_{12})$alkenyl, (d) —$(C_3-C_{10})$cycloalkyl, (e) -aryl or (f) -het;

$R^{25}$ for each occurrence is independently (a) hydrogen, (b) —$(C_1-C_6)$alkyl, (c) —$COR^{29}$ or (d) —$SO_2R^{29}$;

$R^{26}$ and $R^{27}$ for each occurrence are independently (a) hydrogen, (b) —$(C_1-C_6)$alkyl, (c) —$(C_3-C_{10})$cycloalkyl, (d) —$(C_0-C_6)$alkyl-aryl, or (e) —$(C_0-C_6)$alkyl-het, $R^{28}$ is (a) hydrogen, (b) —$(C_1-C_{12})$alkyl optionally substituted with one or more substituents independently selected from Group V, (c) —$(C_2-C_{12})$alkenyl, (d) —$(C_3-C_{10})$cycloalkyl, (e) -aryl or (f) -het;

$R^{29}$ is (a) —$(C_1-C_{12})$alkyl optionally substituted with one or more substituents independently selected from Group V, (b) —$(C_2-C_{12})$alkenyl, (c) —$(C_3-C_{10})$cycloalkyl, (d) -aryl or (e) -het;

$R^{30}$ is (a) hydrogen, (b) —$(C_1-C_{12})$alkyl optionally substituted with one or more substituents independently selected from Group V, (c) —$(C_1-C_{12})$alkenyl, (d) —$(C_3-C_{10})$cycloalkyl, (e) —$C(O)$—$R^{31}$ or (f) —$S(O)_m$—$R^{32}$;

$R^{31}$ is (a) hydrogen, (b) —$(C_1-C_{12})$alkyl optionally substituted with one or more substituents independently selected from Group V, (c) —$(C_2-C_{12})$alkenyl, (d) —$(C_3-C_{10})$cycloalkyl, (e) -aryl, (f) -het or (g) —$OR^{34}$;

$R^{32}$ is (a) hydrogen, (b) —$(C_1-C_{12})$alkyl optionally substituted with one or more substituents independently selected from Group V, (c) —$(C_2-C_{12})$alkenyl, (d) —$(C_3-C_{10})$cycloalkyl, (e) -aryl or (f) -het;

$R^{33}$ is (a) —$(C_0-C_6)$alkyl-aryl, (b) —$(C_0-C_6)$alkyl-het, (c) —$(C_7-C_{12})$alkyl optionally substituted with one or more substituents independently selected from Group V, (d) —$(C_1-C_6)$alkyl wherein at least one carbon atom is substituted with 1 to 3 fluoro atoms, (e) —$(C_2-C_{12})$alkenyl or (f) —$(C_3-C_{10})$cycloalkyl;

$R^{34}$ is (a) -aryl, (b) -het, (c) —$(C_1-C_{12})$alkyl optionally substituted with one or more substituents independently selected from Group V, (d) —$(C_2-C_{12})$alkenyl or (e) —$(C_3-C_{10})$cycloalkyl;

—$(C_3-C_{10})$cycloalkyl for each occurrence is a fully or partially saturated mono-, bi- or tricyclic ring containing three to ten carbon atoms; wherein in the bicyclic ring, a monocyclic cycloalkyl ring is spiro fused to another cycloalkyl ring or is fused via two carbon atoms to a benzene ring or another cycloalkyl ring; and wherein in the tricyclic ring, a bicyclic ring is spiro fused to a cycloalkyl ring or is fused via two atoms to a benzene ring or another cycloalkyl ring;

said —$(C_3-C_{10})$cycloalkyl optionally contains one to three bridging atoms independently selected from carbon, oxygen, sulfur and nitrogen; said bridging atoms are attached to two carbon atoms in the ring; and said bridging atoms are optionally substituted with one to three groups independently selected from —$(C_1-C_6)$alkyl and hydroxy;

said cycloalkyl ring is optionally substituted on one ring if the moiety is monocyclic, on one or both rings if the moiety is bicyclic, or on one, two or three rings if the moiety is tricyclic, with one or more substitutents independently selected from Group V;

Group V is (a) —$(C_1-C_6)$alkyl optionally substituted with one or two hydroxy, (b) —$(C_2-C_5)$alkynyl, (c) -halogen, (d) —$NR^{35}R^{36}$, (e) —$NO_2$, (f) —$OCF_3$, (g) —$OR^{37}$, (h) —$SR^{37}$, (i) -oxo, (j) -trifluoromethyl, (k) —CN, (l) —$C(O)NR^{35}$—OH, (m) —$COOR^{35}$, (n) —O—$C(O)$—$(C_1-C_6)$alkyl, (o) —$(C_3-C_{10})$cycloalkyl optionally substituted with CN, (p) —$(C_0-C_6)$alkyl-aryl, (q) —$(C_0-C_6)$alkyl-het, (r) —$C(O)$—$(C_1-C_6)$alkyl or (s) —$C(O)$-aryl;

$R^{35}$ and $R^{36}$ for each occurrence are independently (a) hydrogen, (b) —$(C_1-C_6)$alkyl or (c) —$(C_0-C_6)$alkyl-aryl;

$R^{37}$ is (a) hydrogen, (b) —$(C_1-C_6)$alkyl optionally substituted with one or more halo, hydroxy or methoxy, (c) —$(C_0-C_6)$alkyl-aryl or (d) —$(C_0-C_6)$alkyl-het;

aryl is (a) phenyl optionally substituted with one or more substituents independently selected from Group Z; (b) naphthyl optionally substituted with one or more substituents independently selected from Group Z or (c) biphenyl optionally substituted with one or more substituents independently selected from Group Z;

het for each occurrence is a 4-, 5-, 6-, 7- and 8-membered fully saturated, partially saturated or fully unsaturated mono-, bi- or tricyclic heterocyclic ring containing from one to four heteroatoms independently selected from the group consisting of oxygen, sulfur and nitrogen; wherein in the bicyclic ring, a monocyclic heterocyclic ring is spiro fused to a —$(C_3-C_8)$cycloalkyl ring or to another heterocyclic ring which is fully or partially saturated; or is fused via two atoms to a benzene ring, a —$(C_3-C_8)$cycloalkyl ring or another heterocyclic ring; and wherein in the tricyclic ring, a bicyclic ring is spiro fused to a —$(C_3-C_8)$cycloalkyl ring or to another heterocyclic ring which is fully or partially saturated; or is fused via two atoms to a benzene ring, a $(C_3-C_6)$cycloalkyl ring, or another heterocyclic ring;

said het optionally contains one to three bridging atoms independently selected from oxygen, sulfur and nitrogen; said bridging atoms are attached to two other atoms in the ring; and said bridging atoms are optionally substituted with one to three groups independently selected from —($C_1$–$C_6$) alkyl and hydroxy;

said het optionally has one or two oxo groups substituted on carbon or one or two oxo groups substituted on sulfur;

said het is optionally substituted on carbon or nitrogen, on one ring if the moiety is monocyclic, on one or both rings if the moiety is bicyclic, or on one, two or three rings if the moiety is tricyclic, with one or more substituents independently selected from Group Z;

Group Z for each occurrence is independently (a) hydrogen, (b) halogen, (c) trifluoromethyl, (d) hydroxy, (e) —$OCF_3$, (f) —CN, (g) —$NO_2$, (h) —($C_1$–$C_6$)alkyl optionally substituted with one or more substituents independently selected from the group consisting of hydroxy, halogen, —$OCF_3$ and —$CF_3$, (i) —($C_2$–$C_6$)alkenyl optionally substituted with phenyl, (j) —($C_2$–$C_5$)alkynyl, (k) —($C_1$–$C_6$) alkoxy, (l) —($C_0$–$C_6$)alkyl-phenyl optionally substituted with one or more substituents independently selected from the group consisting of halogen, —$OCF_3$, —$CF_3$, —($C_1$–$C_4$) alkyl, —($C_1$–$C_4$)alkoxy and —$C(O)CH_3$, (m) —($C_0$–$C_6$) alkyl-naphthyl optionally substituted with one or more substituents independently selected from the group consisting of halogen, —$OCF_3$, —$CF_3$, —($C_1$–$C_4$)alkyl, —($C_1$–$C_4$) alkoxy and —$C(O)CH_3$, (n) —$C(O)_2R^{35}$, (o) —($C_0$–$C_6$) alkyl-$C(O)NR^{35}R^{36}$, (p) —($C_0$–$C_6$)alkyl-$C(O)R^{38}$, (q) —$NR^{35}R^{36}$, (r) —$NR^{35}$—$C(O)NR^{35}R^{36}$, (s) —$NR^{35}$—C(O)$R^{36}$, (t) —$OR^{37}$, (u) —$SR^{37}$, (v) —($C_3$–$C_{10}$)cycloalkyl, (w) —($C_0$–$C_6$)alkyl-pyridinyl optionally substituted with one or more —($C_1$–$C_6$)alkyl which is optionally substituted with one or more substituents independently selected from the group consisting of hydroxy and halo, (x) —($C_0$–$C_6$) alkyl-piperidinyl optionally substituted with one or more —($C_1$–$C_6$)alkyl which is optionally substituted with one or more substituents independently selected from hydroxy and halo, (y) —$SO_2$—$R^{37}$, (z) —$SO_2$—$NR^{35}R^{36}$ or (a1) —S-phenyl-$CH_2OH$;

$R^{38}$ is (a) —($C_1$–$C_6$)alkyl, (b) —(CO—$C_6$)alkyl-phenyl, (c) —($C_0$–$C_6$)alkyl-phenanthrenyl optionally substituted with one to three $CF_3$, (d) —($C_0$–$C_6$)alkyl-pyrrolidinyl or (e) —($C_0$–$C_6$)alkyl-morpholinyl;

or any two Z Groups for any occurrence in the same variable may be taken together to form (a) a carbocyclic ring of the formula —$(CH_2)_e$— or (b) a heterocyclic ring selected from the group consisting of —$O(CH_2)_fO$—, —$(CH_2)_g$ NH— and —CH=CHNH—;

m is 0, 1 or 2;

n is 0, 1, 2 or 3;

b is 3, 4, 5, 6 or 7;

c, f, g, j and k are each independently 2, 3, 4, 5 or 6; and e is 3, 4, 5, 6 or 7;

provided that in a compound of Formula I: 1) the substituent —$C(R^{14})(R^{15})(R^{16})$ in $R^4$ is other than ($C_1$–$C_4$) alkyl; and 2) $R^4$ is halo only when $R^8$ is —C(O)—$OR^9$ or —$C(O)NR^{10}R^{11}$.

More particularly, the present invention provides compounds of Formula I, and prodrugs, isomers or pharmaceutically acceptable salts thereof, wherein W is oxygen.

More particularly, the present invention provides compounds of Formula I, and prodrugs, isomers or pharmaceutically acceptable salts thereof, wherein $R^1$ is located at the 3 position, $R^2$ is located at the 5 position, $R^3$ is located at the 2' position, $R^4$ is located at the 3' position, $R^5$ is located at the 4' position and $R^6$ is located at the 5' position.

More particularly, the present invention provides compounds of Formula I, and prodrugs, isomers or pharmaceutically acceptable salts thereof, wherein $R^3$ is hydrogen, $R^5$ is hydroxy or methoxy, $R^6$ is hydrogen, $R^7$ is hydrogen and $R^8$ is hydrogen.

More particularly, the present invention provides compounds of Formula I, and prodrugs, isomers or pharmaceutically acceptable salts thereof, wherein $R^1$ and $R^2$ are each independently methyl, bromo or chloro.

More particularly, the present invention provides compounds of Formula I, and pharmaceutically acceptable salts thereof, wherein $R^4$ is $S(O)_2NR^{21}R^{22}$; $R^{21}$ is hydrogen or methyl; and $R^{22}$ is (a) —($C_5$–$C_8$)alkyl, (b) bicyclo[2.2.1] hept-2-yl, (c) 1,2,3,4-tetrahydro-naphthalen-1-yl, (d) cyclobutyl, (e) cyclopentyl, (f) cyclohexyl or (g) phenyl optionally substituted with one or more fluoro. Even more particularly, the present invention provides such compounds, and pharmaceutically acceptable salts thereof, wherein $R^1$ is methyl or chloro, $R^2$ is methyl or chloro, $R^5$ is hydroxy and $R^{21}$ is hydrogen.

In addition, more particularly, the present invention provides compounds of Formula I, and pharmaceutically acceptable salts thereof, wherein $R^4$ is $S(O)_2NR^{21}R^{22}$; $R^{21}$ and $R^{22}$ are taken together with the nitrogen atom to which they are attached to form het; and het is (a) piperidinyl optionally substituted with one or more substituents independently selected from the group consisting of methyl and phenyl, (b) pyrrolidinyl, (c)1,3,3-trimethyl-6-aza-bicyclo [3.2.1]octanyl, (d) indolinyl, (e) spiro[8-azabicyclo[3.2.1] octane-3,2'-(3'H)-dihydro-furan], (f) spiro[8-azabicyclo [3.2.1]octane-3,2'-[1,3]dioxolane] or (g) 8-aza-bicyclo [3.2.1]octanyl optionally substituted with one or more substituents independently selected from the group consisting of oxo and hydroxy. Even more particularly, the present invention provides such compounds, and pharmaceutically acceptable salts thereof, wherein $R^1$ is methyl or chloro, $R^2$ is methyl or chloro, and $R^5$ is hydroxy.

In addition, more particularly, the present invention provides compounds of Formula I, and pharmaceutically acceptable salts thereof, wherein $R^4$ is —$C(O)NR^{19}R^{20}$, $R^{19}$ is hydrogen; and $R^{20}$ is (a) cyclopentyl optionally substituted with one or more —$CH_2OH$, (b) bicyclo[2.2.1]hept-2-yl optionally substituted with one or more substituents independently selected from the group consisting of —$CH_2OH$ and methyl, or (c) bicyclo[3.1.1]hept-3-yl optionally substituted with one or more methyl. Even more particularly, the present invention provides such compounds, and pharmaceutically acceptable salts thereof, wherein $R^1$ and $R^2$ are each chloro or dibromo, and $R^5$ is hydroxy.

In addition, more particularly, the present invention provides compounds of Formula I, and pharmaceutically acceptable salts thereof, wherein $R^4$ is —$C(O)NR^{19}R^{20}$; $R^{19}$ and $R^{20}$ are taken together with N to form het; het is (a) piperidinyl optionally substituted with one or more substituents independently selected from the group consisting of methyl and phenyl, (b) pyrrolidinyl, (c) azepanyl, (d) indolinyl or (e) 3,4-dihydro-1H-isoquinolinyl. Even more particularly, the present invention provides such compounds, and pharmaceutically acceptable salts thereof, wherein $R^1$ and $R^2$ are each chloro and $R^5$ is hydroxy.

In addition, more particularly, the present invention provides compounds of Formula I, and pharmaceutically acceptable salts thereof, wherein $R^4$ is —$CH_2$—$NR^{17}R^{18}$; $R^{17}$ is hydrogen; and $R^{18}$ is (a) phenyl optionally substituted with one or more substituents independently selected from methyl and fluoro, (b) benzo[1,3]dioxol-5-yl or (c) indanyl. Even more particularly, the present invention provides such compounds, and pharmaceutically acceptable salts thereof, wherein $R^1$ and $R^2$ are each chloro or bromo and $R^5$ is hydroxy.

In addition, more particularly, the present invention provides compounds of Formula I, and pharmaceutically acceptable salts thereof, wherein $R^4$ is —$CH_2$—$NR^{17}R^{18}$; $R^{17}$ and $R^{18}$ are taken together with the nitrogen atom to which they are attached to form het; and het is piperidinyl optionally substituted with one or more methyl. Even more particularly, the present invention provides such compounds, and pharmaceutically acceptable salts thereof, wherein $R^1$ and $R^2$ are each chloro and $R^5$ is hydroxy.

In addition, more particularly, the present invention provides compounds of Formula I, and pharmaceutically acceptable salts thereof, wherein $R^4$ is —$NR^{19}$—$C(O)$—$R^{20}$; $R^{19}$ is hydrogen; and $R^{20}$ is (a) cyclohexyl, (b) phenyl optionally substituted with one or more substituents independently selected from the group consisting of —$OCF_3$, -fluoro and —$CF_3$, (c) -isoxazolyl optionally substituted with methyl or (d) —$(C_3-C_5)$alkyl. Even more particularly, the present invention provides such compounds, and pharmaceutically acceptable salts thereof, wherein $R^1$ and $R^2$ are each chloro and $R^5$ is hydroxy.

In addition, more particularly, the present invention provides compounds of Formula I, and pharmaceutically acceptable salts thereof, wherein $R^4$ is —$S(O)_2R^{22}$; and $R^{22}$ is (a) phenyl optionally substituted with one or more substituents independently selected from the group consisting of methyl and ethyl, (b) indanyl or (c) —$(CH_2)$—$(C_4-C_6)$ cycloalkyl. Even more particularly, the present invention provides such compounds, and pharmaceutically acceptable salts thereof, wherein $R^1$ and $R^2$ are each chloro and $R^5$ is hydroxy.

In addition, more particularly, the present invention provides compounds of Formula I, and pharmaceutically acceptable salts thereof, wherein $R^4$ is —$C(R^{14})(R^{15})(R^{16})$; $R^{14}$ is hydroxy; $R^{15}$ is hydrogen; and $R^{16}$ is (a) phenyl optionally substituted with one or more fluoro or (b) —$(C_1-C_5)$alkyl. Even more particularly, the present invention provides such compounds, and pharmaceutically acceptable salts thereof, wherein $R^1$ is methyl, chloro or bromo; and $R^2$ is methyl, chloro or bromo.

In addition, more particularly, the present invention provides compounds of Formula I, and pharmaceutically acceptable salts thereof, wherein $R^4$ is —$C(R^{14})(R^{15})(R^{16})$; $R^{14}$ is hydrogen or methyl; $R^{15}$ is hydrogen; and $R^{16}$ is (a) phenyl optionally substituted with one or more fluoro or (b) —$(C_1-C_5)$alkyl. Even more particularly, the present invention provides such compounds, and pharmaceutically acceptable salts thereof, wherein $R^1$ is methyl, chloro or bromo; $R^2$ is methyl, chloro or bromo; and $R^5$ is hydroxy.

In addition, more particularly, the present invention provides compounds of Formula I, and pharmaceutically acceptable salts thereof, wherein $R^4$ is —$C(R^{14})(R^{15})(R^{16})$; $R^{14}$ and $R^{15}$ are taken together with the carbon atom to which they are attached to form a carbonyl group; and $R^{16}$ is (a) phenyl optionally substituted with one or more fluoro (b) or —$(C_1-C_5)$alkyl. Even more particularly, the present invention provides such compounds, and pharmaceutically acceptable salts thereof, wherein $R^1$ is methyl, chloro or bromo; $R^2$ is methyl, chloro or bromo; and $R^5$ is hydroxy.

In addition, more particularly, the present invention provides compounds of Formula I, and pharmaceutically acceptable salts thereof, wherein $R^4$ is —$NR^{21}$—$C(O)$—$NR^{21}R^{22}$; each $R^{21}$ is hydrogen; and $R^{22}$ is phenyl optionally substituted with one or more chloro. Even more particularly, the present invention provides such compounds, and pharmaceutically acceptable salts thereof, wherein $R^1$ and $R^2$ are each methyl or chloro; and $R^5$ is hydroxy.

In addition, more particularly, the present invention provides compounds of Formula I, and pharmaceutically acceptable salts thereof, wherein $R^4$ is $NR^{21}$—$S(O)_2$—$R^{22}$; $R^{21}$ is hydrogen; and $R^{22}$ is —$(C_0-C_2)$alkyl-phenyl optionally substituted with one or more fluoro. Even more particularly, the present invention provides such compounds, and pharmaceutically acceptable salts thereof, wherein $R^1$ is chloro, methyl or bromo; $R^2$ is chloro, methyl or bromo; and $R^5$ is hydroxy.

In another aspect, the present invention provides compounds of Formula I, and prodrugs, isomers and pharmaceutically acceptable salts thereof, wherein $R^1$ and $R^2$ are each independently chloro or methyl; $R^3$ is hydrogen; $R^4$ and $R^5$ are taken together to form

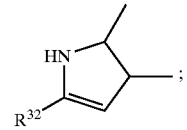

$R^6$ is hydrogen; and $R^{32}$ is hydrogen or methyl.

In another aspect, the present invention provides compounds of Formula I, and prodrugs, isomers and pharmaceutically acceptable salts thereof, wherein $R^3$ is hydrogen, $R^4$ is Br, $R^5$ is hydroxy or methoxy, $R^6$ is hydrogen and $R^7$ is hydrogen. More particularly, the present invention provides such compounds, and pharmaceutically acceptable salts thereof, wherein $R^1$ and $R^2$ are each methyl. Even more particularly, the present invention provides such compounds, and pharmaceutically acceptable salts thereof, wherein $R^8$ is —$C(O)NR^{10}R^{11}$; $R^{10}$ is hydrogen; and $R^{11}$ is (a) —$CH_2$-furanyl (b) —$CH_2$-phenyl optionally substituted with one or more $CF_3$, (c) —$CH_2$-cyclohexyl optionally substituted with one or more CN, (d) —$CH_2$-pyridinyl, (e) —$(CH_2)_3$-imidazolyl or (f) —$(CH_2)_2$—$N(CH_3)_2$.

In addition, more particularly, the present invention provides compounds of Formula I, and pharmaceutically acceptable salts thereof, wherein $R^8$ is —$C(O)NR^{10}R^{11}$; $R^{10}$ and $R^{11}$ are taken together with the nitrogen atom to which they are attached to form het; and het is (a) thiazolidinyl or (b) 4-oxo-piperidinyl optionally substituted with one or more carboxylic acid methyl ester.

In addition, more particularly, the present invention provides compounds of Formula I, and pharmaceutically acceptable salts thereof, wherein $R^8$ is —$C(O)OR^9$; and $R^9$ is —$(CH_2)_2$-piperazinyl optionally substituted with one or more 4-acetyl-phenyl.

Unless otherwise provided herein:

"Alkyl" means a straight or branched hydrocarbon chain radical, including as the case may be, for example, methyl, ethyl, n-propyl, isopropyl, n-butyl and the like. For example, alkyl groups include groups such as the following —$(C_1-C_4)$alkyl, —$(C_1-C_6)$alkyl, —$(C_1-C_{12})$alkyl and —$(C_7-C_{12})$alkyl. An alkyl group may be optionally substituted with one or more substituents, preferably one to three substitutents. For example, an alkyl group may be optionally substituted with one or more substituents independently selected from Group V, as defined above, preferably one to three substituents independently selected from Group V.

"Alkenyl" means a straight or branched unsaturated, univalent aliphatic radical.

"Alkoxy" means an alkyl radical which is attached to the remainder of the molecule by oxygen, including as the case may be, for example, methoxy.

"Alkynyl" means a straight or branched acyclic hydrocarbon radical with one triple bond, including as the case may be, for example, acetylene.

"Carbocyclic" (carbocycle) means an unsaturated, or a partially or fully saturated ring having only carbon atoms in its nucleus, including as the case may be an aryl (an organic radical derived from an aromatic hydrocarbon by the removal of one atom, e.g., phenyl from benzene, also including, for example, naphthyl). A carbocyclic ring may be optionally substituted with one or more substituents, preferably one to three substituents. For example, a carbocyclic ring may be optionally substituted with one or more substituents independently selected from Group V, as defined above, preferably one to three substituents independently selected from Group V.

"Cycloalkane" means a saturated, monocyclic hydrocarbon, including as the case may be, for example, cyclohexane.

"Cycloalkyl" means a monocyclic or polycyclic radical derived from a cycloalkane, including as the case may be, for example, cyclopentyl and cyclohexyl. For example, cycloalkyl groups include groups such as $-(C_3-C_{10})$ cycloalkyl. A cycloalkyl group may be optionally substituted with one or more substituents, preferably one to four substituents. For example, a cycloalkyl group may be optionally substituted with one or more substituents independently selected from Group V, as defined above, preferably one to four substituents independently selected from Group V.

"Aryl" means an organic radical derived from an aromatic hydrocarbon by the removal of one atom, for example, phenyl from benzene. Other aryl groups include, for example, naphthyl and biphenyl. An aryl group may be optionally substituted with one or more substituents, preferably one to three substituents. For example, an aryl group may be optionally substituted with one or more substituents independently selected from Group Z, as defined above, preferably one to three substituents independently selected from Group Z.

"Halo" or "halogen" means a radical derived from the elements fluorine, chlorine, bromine or iodine.

"Heterocyclic" ("heterocycle" or "het"), as used herein, unless otherwise indicated, includes aromatic and non-aromatic heterocyclic groups containing one or more heteroatoms, generally 1 to 4 heteroatoms, each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, tetrahydroquinolyl, tetrahydroisoquinolyl, piperidino, piperidyl, morpholino, morpholinyl, thiomorpholino, thiomorpholinyl, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furanyl, benzofuranyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). A heterocyclic group may be optionally substituted with one or more substituents, preferably one to three substituents. For example, a heterocyclic group may be optionally substituted with one or more substituents independently selected from Group Z, as defined above, preferably one to three substituents independently selected from Group Z.

Where heterocyclic groups are specifically recited or covered as substituents for the compounds of Formula I, it is understood that, unless specifically noted otherwise, all suitable isomers of such heterocyclic groups are intended.

"Hydrate" is a crystalline form of a compound or salt thereof, containing one or more molecules of water of crystallization, i.e., a compound of Formula I or a salt thereof, containing water combined in the molecular form.

"Pharmaceutically acceptable" means that the carrier, diluent, vehicle excipients and/or salt must be compatible with the other ingredients of the formulation, and not deleterious to the recipient thereof.

"Pharmaceutically acceptable salts" of the compounds of this invention may be formed of the compound itself, prodrugs, e.g. esters, isomers and the like, and include all of the pharmaceutically acceptable salts which are most often used in pharmaceutical chemistry; for example, salts may be formed with inorganic or organic acids such as hydrochloric acid, hydrobromic acid, hydroiodic acid, carboxylic acids, sulfonic acids including such agents as naphthalenesulfonic, ethanesulfonic, hydroxyethanesulfonic, methanesulfonic ("mesylate"), benzenesulfonic ("besylate") and toluenesulfonic acids, e.g., p-toluenesulfonic ("tosylate"), sulfuric acid, nitric acid, phosphoric acid, tartaric acid, pyrosulfuric acid, metaphosphoric acid, succinic acid, formic acid, phthalic acid, malic acid, maleic acid, lactic acid, ascorbic acid, glycollic acid, gluconic acid, mandelic acid, glutamic acid, aspartic acid, fumaric acid, pyruvic acid, phenylacetic acid, pamoic acid, nicotinic acid, and the like. Suitable pharmaceutically acceptable salts also include alkali metal salts (e.g. sodium, potassium salts), alkaline earth metal salts (e.g. magnesium, calcium salts), amine salts (e.g. ammonium, alkylammonium, dialkylammonium, trialkylammonium, tetraalkylammonium, diethanolammonium, tri-ethanolammonium and guanidinium salts). Preferred salts include salts of organic acids selected from formic, acetic, trifluoroacetic, propionic, benzoic, citric, maleic, tartaric, methanesulfonic, benzenesulfonic or toluenesulfonic; salts of inorganic acids selected from hydrochloric, hydrobromic, sulfuric or phosphoric; salts of amino acids selected from aspartic and glutamic; and salts of sodium and potassium.

"Polymorph" is a compound or salt thereof, such as the compound of Formula I or a salt thereof, which occurs in two or more forms.

"Prodrug" is a drug precursor which, following administration, releases the drug in vivo via some chemical or physiological process (e.g., a prodrug on being brought to the physiological pH or through enzyme action is converted to the desired drug form); exemplary prodrugs upon cleavage release the corresponding free acid, and such hydrolyzable ester-forming residues of the compounds of Formula I include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxy-carbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as b-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

"Radical" is a group of atoms that behaves as a single atom in a chemical reaction, e.g., an organic radical is a group of atoms which confers characteristic properties on a compound containing it, or which remains unchanged during a series of reactions.

"Solvate" is a molecular or ionic complex of molecules or ions of a solvent with those of a solute; a "solvate" wherein the solvent is water, forms "hydrates" or hydrated ions.

"Spirocycloalkyl" means cycloalkyl having a spiro union (the union formed by a single atom which is the only common member of the rings).

"Treating," "treat" or "treatment" includes, inter alia, preventative (e.g., prophylactic), palliative and curative treatment.

"Therapeutically effective amount" means an amount of a compound that ameliorates, attenuates, or eliminates one or more symptoms of a particular disease or condition or prevents or delays the onset of one of more symptoms of a particular disease or condition.

"Patient" means animals, such as dogs, cats, cows, horses, sheep, and humans. Particularly preferred patients are mammals, including both males and females.

The present invention provides methods of treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) which comprise administering to said mammal a therapeutically effective amount of a compound of Formula I, an isomer thereof, a prodrug of said compound or isomer, or a pharmaceutically acceptable salt of said compound, isomer or prodrug, as described above. Especially preferred are such methods wherein said condition is obesity. Such methods further comprise administering an anorectic agent or a lipase inhibitor.

In another aspect, the present invention provides methods of treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) which comprise administering to said mammal a therapeutically effective amount of a compound of Formula I, an isomer thereof, a prodrug of said compound or isomer, or a pharmaceutically acceptable salt of said compound, isomer or prodrug, as described above, and an anorectic agent.

In another aspect, the present invention provides methods of treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) which comprise administering to said mammal a therapeutically effective amount of a compound of Formula I, an isomer thereof, a prodrug of said compound or isomer, or a pharmaceutically acceptable salt of said compound, isomer or prodrug, as described above, and a lipase inhibitor.

In a preferred aspect, the present invention provides methods of treating obesity in mammals (including a human being) which comprise administering to said mammal an obesity treating effective amounts of a compound of Formula I, an isomer thereof, a prodrug of said compound or isomer, or a pharmaceutically acceptable salt of said compound, isomer or prodrug, as described above. In yet another preferred aspect, the present invention provides methods of inducing weight loss in a mammal which comprise administering to said mammal a therapeutically effective amount of a compound of Formula I, an isomer thereof, a prodrug of said compound or isomer, or a pharmaceutically acceptable salt of said compound, isomer or prodrug.

In another aspect, the present invention provides methods of treating obesity in mammals (including a human being) which comprise administering to said mammal obesity treating effective amounts of a compound of Formula I, an isomer thereof, a prodrug of said compound or isomer, or a pharmaceutically acceptable salt of said compound, isomer or prodrug, as described above, and an anorectic agent.

In another aspect, the present invention provides methods of treating obesity, in a mammal (including a human being) which comprise administering to said mammal obesity treating effective amounts of a compound of Formula I, an isomer thereof, a prodrug of said compound or isomer, or a pharmaceutically acceptable salt of said compound, isomer or prodrug, as described above, and a lipase inhibitor.

In another aspect, the present invention provides pharmaceutical compositions comprising an amount of a compound of Formula I, an isomer thereof, a prodrug of said compound or isomer, or a pharmaceutically acceptable salt of said compound, isomer or prodrug, as described above, and a pharmaceutically acceptable vehicle, diluent or carrier.

In another aspect, the present invention provides pharmaceutical compositions comprising a compound of Formula I, an isomer thereof, a prodrug of said compound or isomer, or a pharmaceutically acceptable salt of said compound, isomer or prodrug, as described above; an anorectic agent and a pharmaceutically acceptable vehicle, diluent or carrier.

In another aspect, the present invention provides pharmaceutical compositions comprising a compound of Formula I, an isomer thereof, a prodrug of said compound or isomer, or a pharmaceutically acceptable salt of said compound, isomer or prodrug, as described above; a lipase inhibitor and a pharmaceutically acceptable vehicle, diluent or carrier.

In another aspect, the present invention provides pharmaceutical compositions for treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) comprising an amount of a compound of Formula I, an isomer thereof, a prodrug of said compound or isomer, or a pharmaceutically acceptable salt of said compound, isomer or prodrug, as described above, and a pharmaceutically acceptable vehicle, diluent or carrier.

In another aspect, the present invention provides pharmaceutical compositions for treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) comprising a compound of Formula I, an isomer thereof, a prodrug of said compound or isomer, or a pharmaceutically acceptable salt of said compound, isomer or prodrug, as described above; an anorectic agent, and a pharmaceutically acceptable vehicle, diluent or carrier.

In another aspect, the present invention provides pharmaceutical compositions for treating a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal (including a human being) comprising a compound of Formula I, an isomer thereof, a prodrug of said compound or isomer, or a pharmaceutically acceptable salt of said compound, isomer or prodrug, as described above; a lipase inhibitor, and a pharmaceutically acceptable vehicle, diluent or carrier.

In another preferred aspect, the present invention provides pharmaceutical compositions for treating obesity in a mammal (including a human being) comprising a compound of Formula I, an isomer thereof, a prodrug of said compound or isomer, or a pharmaceutically acceptable salt of said compound, isomer or prodrug, as described above, and a pharmaceutically acceptable vehicle, diluent or carrier. In yet another preferred aspect, the present invention provides pharmaceutical compositions for inducing weight loss comprising a weight loss-treating amount of a compound of Formula I, an isomer thereof, a prodrug of said compound or isomer, or a pharmaceutically acceptable salt of said compound, isomer or prodrug; and a pharmaceutically acceptable carrier, vehicle or diluent.

In a preferred aspect, the present invention provides pharmaceutical compositions for treating obesity in a mammal (including a human being) comprising a compound of Formula I, an isomer thereof, a prodrug of said compound or isomer, or a pharmaceutically acceptable salt of said compound, isomer or prodrug, as described above; an anorectic agent, and a pharmaceutically acceptable vehicle, diluent or carrier.

In yet another aspect, the present invention provides pharmaceutical compositions for treating obesity in a mammal (including a human being) comprising a compound of Formula I, an isomer thereof, a prodrug of said compound or isomer, or a pharmaceutically acceptable salt of said compound, isomer or prodrug, as described above; a lipase inhibitor, and a pharmaceutically acceptable vehicle, diluent or carrier.

In another aspect, the present invention provides kits for the treatment of a condition selected from obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure which comprise: a first compound, said first compound being a compound of Formula I, an isomer thereof, a prodrug of said compound or isomer, or a pharmaceutically acceptable salt of said compound, isomer or prodrug, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container for containing said first and second dosage forms; wherein the amounts of said first and second compounds result in a therapeutic effect.

In another preferred aspect, the present invention provides kits for the treatment of a obesity which comprise: a first compound, said first compound being a compound of Formula I, an isomer thereof, a prodrug of said compound or isomer, or a pharmaceutically acceptable salt of said compound, isomer or prodrug, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

In another aspect, the present invention provides kits for the treatment of a condition selected from the group consisting of obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure which comprises:

a first compound, said first compound being a compound of Formula I, an isomer thereof, a prodrug of said compound or isomer, or a pharmaceutically acceptable salt of said compound, isomer or prodrug and a pharmaceutically acceptable carrier, vehicle or diluent, in a first unit dosage form;

a second compound, said second compound being useful for the treatment of a condition selected from the group consisting of obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure, and a pharmaceutically acceptable carrier, vehicle or diluent in a second unit dosage form; and a container for containing said first and second dosage forms; wherein the amounts of said first and second compounds result in a therapeutic effect.

In another aspect, the present invention provides methods of treating a condition selected from the group consisting of obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal which comprises administering to said mammal a therapeutically effective amount of a compound of Formula I, an isomer thereof, a prodrug of said compound or isomer, or a pharmaceutically acceptable salt of said compound, isomer or prodrug, in combination with at least one additional compound useful for treating a condition selected from the group consisting of obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure.

In another aspect, the present invention provides pharmaceutical compositions comprising an amount of a compound of Formula I, an isomer thereof, a prodrug of said compound or isomer, or a pharmaceutically acceptable salt of said compound, isomer or prodrug; at least one additional compound useful for treating a condition selected from the group consisting of obesity, overweight condition, hyperlipidemia, thyroid disease, hypothyroidism, thyroid cancer, diabetes mellitus, atherosclerosis, hypertension, coronary heart disease, hypercholesteremia, depression, osteoporosis, cardiac arrhythmias, glaucoma and congestive heart failure in a mammal; and a pharmaceutically acceptable carrier, vehicle or diluent.

DETAILED DESCRIPTION OF THE INVENTION

Unless otherwise noted, throughout this document: ° C. is degrees Centigrade; % is percent; Calc. is calculated data; cm is centimeter; DEE is diethyl ether; DME is dimethyl ether; DMF is dimethylformamide; DMSO is dimethylsulfoxide; DTT is dithiothreitol; EtOAc is ethyl acetate; EtOH is ethanol; Found is found data; g is gram or grams; h is hour or hours; kg is kilogram or kilograms; KOH is potassium hydroxide; L is liter or liters; M is molar (concentration); MeOH is methanol; mg is milligram or milligrams; min is minute or minutes; mL is milliliter or milliliters; mm is millimole or millimoles; mM is millimolar (concentration); MS is mass spectrum; N is normal (concentration); NaOH is sodium hydroxide; nM is nanomolar (concentration); NMR is proton nuclear magentic resonance spectrum; psi is pounds per square inch; RT is room temperature; TEA is triethylamine; TFA is trifluoroacetic acid; THF is tetrahydrofuran; $\mu$g is microgram or micrograms; and $\mu$L is microliter or microliters.

As disclosed herein, a compound within the scope of Formula I shall at all times be understood to include all active forms of such compounds, including, for example, the free form thereof, e.g., the free acid or base form and also, all prodrugs, polymorphs, hydrates, solvates, stereoisomers, e.g., diastereomers and enantiomers, and the like, and all pharmaceutically acceptable salts as described above. It will also be appreciated that suitable active metabolites of compounds within the scope of Formula I, in any suitable form, are also included herein.

More specifically, certain compounds suitable for use in the present invention such as, for example, certain compounds of Formula I may have asymmetric centers and therefore exist in different enantiomeric forms. All suitable optical isomers, geometric isomers and stereoisomers of such compounds, and mixtures thereof, are considered to be within the scope of the invention. With respect to such compounds, the present invention includes the use of a racemate, a single enantiomeric form, a single diastereomeric form, or mixtures thereof, as suitable. Moreover, such compounds may exist in several tautomeric forms, including the enol form, the keto form and mixtures thereof. All such tautomeric forms and mixtures thereof are included within the scope of the present invention.

In addition, those skilled in the art will easily recognize that physiologically active compounds which have accessible hydroxy groups are frequently administered in the form of pharmaceutically acceptable esters. The compounds of this invention can be administered as esters, formed on the hydroxy groups. While the mechanism has not yet been investigated and not wishing to be bound by theory, it is believed that such esters are metabolically cleaved in the body, and that the actual drug is the hydroxy compound itself. It is possible, as has long been known in pharmaceutical chemistry, to adjust the rate or duration of action of the compound by suitable choices of ester groups.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples below, by substituting a readily available isotopically-labelled reagent for a non-isotopically labelled reagent.

Those skilled in the art will understand from this disclosure how to prepare the compounds of the present invention using any suitable known method. Moreover, the reaction Schemes of the present description illustrate the preparation of the compounds of the present invention and, unless otherwise indicated, the variables in the reaction Schemes are as described above. In addition, the Examples provided herein further illustrate the preparation of the compounds of the present invention.

The starting materials for each synthetic Scheme and Example provided by this description are either commercially available or are prepared according to methods known to those skilled in the art such as described, for example, in the following references: M. W. Miller et al., *J. Med. Chem.* 1981, 24, 1337–1342, preferably the procedures as described in Scheme III at pages 1339–1340; and M. W. Miller et al., *J. Med. Chem.* 1979, 22, 1483–1487, which are hereby incorporated by reference herein.

More specifically, those skilled in the art will understand based upon these references and upon the present disclosure how to prepare the intermediates in the following schemes, wherein W is, for example, oxygen or —$(SO_2)_m$ and the other variables are as described above. It is particularly preferred that W is oxygen. Intermediates in the following schemes, wherein W is, for example, —C(O)— and the other variables are as described above, can be prepared according to literature procedures, such as those described above, e.g., Canadian Patent Nos. 979457 and 992538 and R. D. Carroll et al., J. Med. Chem. 1983, 26, 96–100. Intermediates in the following schemes, wherein W is, for example, —CH₂—, —CHF—, —CF₂— or —CH(OH)— and the other variables are as described above, can be prepared from the intermediates, wherein W is —C(O)— and the other variables are as described above, according to procedures known in the art. Intermediates in the following schemes, wherein W is, for example, —NR³⁰— and the other variables are as described above, can be prepared according to literature procedures, such as those described above, e.g., Canadian Patent Nos. 979457 and 992538. Intermediates in the following schemes, wherein W is, for example, —HC=CH— and the other variables are as described above, can be prepared by procedures analogous to those described in the literature, such as in Dale et al., *J. Amer. Chem. Soc.* 1959, 81, 2143–2145.

It should be understood that the following Schemes are provided solely for the purposes of illustration and do not limit the invention which is defined by the claims.

Scheme A

The compound of Formula A-1 is formylated by reacting it with hexamethylenetetramine at about 65° C. in a suitable acidic reagent, such as, for example, TFA, to give the compound of Formula A-2. The compound of Formula A-2 is demethylated using a suitable boron trihalide, such as boron trichloride or boron tribromide, in a suitable organic solvent, such as 1,2-dichloroethane or dichloromethane, to give the compound of Formula A-3. The aldehyde of Formula A-3 is oxidized to give the carboxylic acid of Formula A-4, using methods well known in the art, for example, Jones oxidation. Preferred oxidation methods include Jones oxidation (chromic acid/aqueous sulfuric acid) and those employing sodium hypochlorite (NaClO, t-butanol in THF).

The carboxylic acid of Formula A-4 is converted to the carboxamide compound of Formula A-5 according to methods known in the art. For example, employment of an acid chloride or anhydride (symmetrical or mixed) of the com-

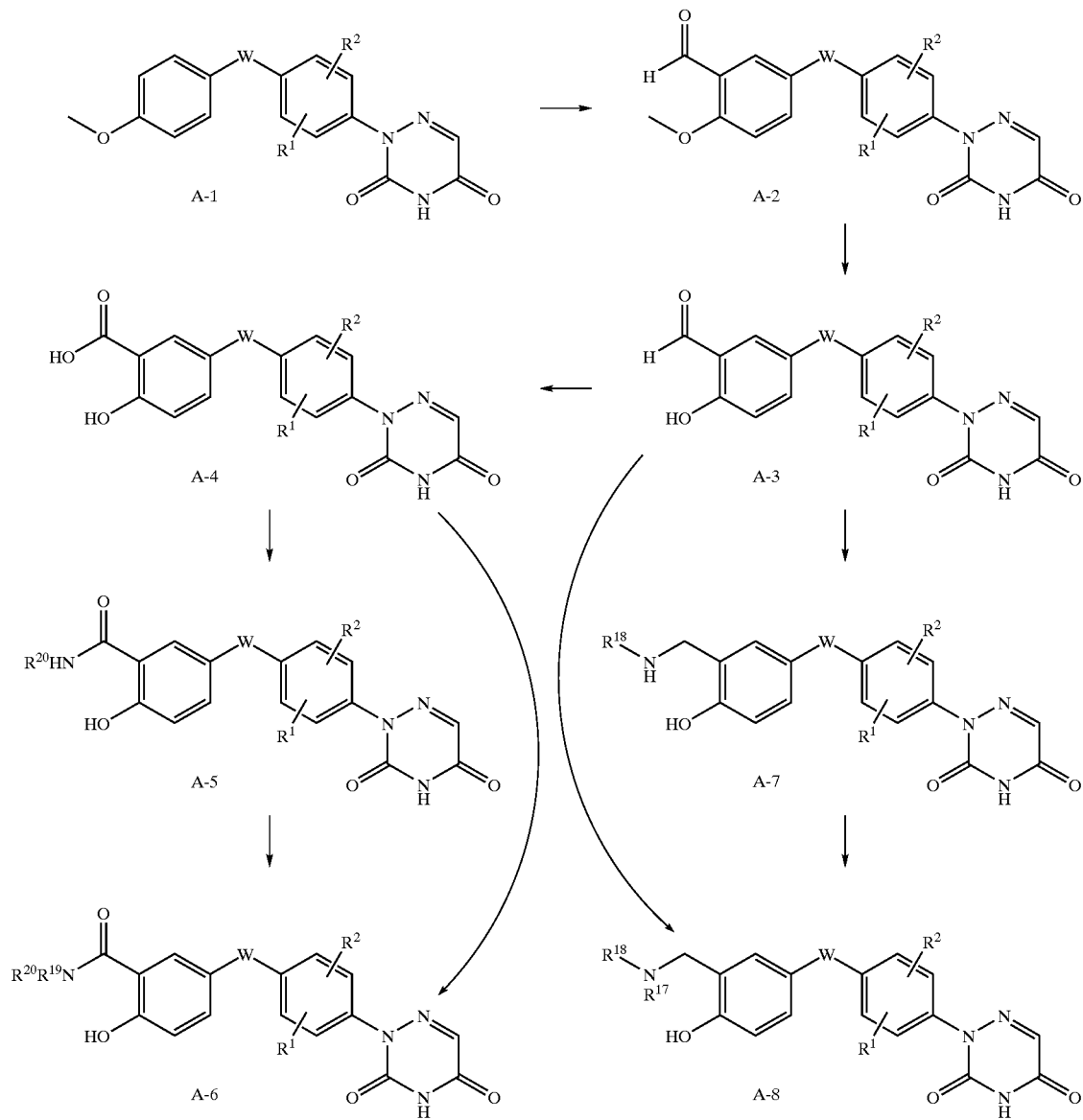

Scheme A pound of Formula A-4 with a primary amine of Formula $R^{20}NH_2$ in a suitable dried aprotic solvent, such as, for example, dichloromethane, THF, DME or DEE, in the presence of a base, such as TEA, dimethylaminopyridine (DMAP) or pyridine, gives the compound of Formula A-5. Also, the carboxylic acid of Formula A-4 is converted to the carboxamide compound of Formula A-6 according to methods known in the art. For example, the carboxylic acid of Formula A-4 is reacted with N-hydroxysuccinimide and dicyclohexylcarbodiimide in a suitable solvent, such as 1,2-dimethoxyethane, and a secondary amine of Formula $R^{19}R^{20}NH$ with a suitable base, such as triethylamine, in a suitable solvent, such as dimethoxyethane to give the carboxamide of Formula A-6. Alternatively, an acid chloride or anhydride (symmetrical or mixed) of the carboxylic acid of Formula A-4 is reacted with a secondary amine of Formula $R^{19}R^{20}NH$ in a suitable solvent in the presence of a suitable base, as described above, to give the carboxamide of Formula A-6.

The aldehyde of Formula A-3 is converted to the aminomethyl derivatives of Formula A-7 and A-8 by methods known in the art. A preferred method utilizes reductive amination, which is accomplished by the reaction of the aldehyde of Formula A-3 with a primary amine of Formula $R^{18}NH_2$ or a secondary amine of Formula $R^{18}R^{17}NH$ and a reducing agent in a suitable solvent to give the compounds of Formula A-7 and A-8, respectively. This reaction is preferably performed in the presence of 3 Å molecular sieves. Preferred reducing agents are sodium cyanoborohydride, sodium triacetoxyborohydride and sodium borohydride. Preferred organic solvents include EtOH, MeOH and 1,2-dichloroethane.

Alternatively, the compound of Formula A-8 can be prepared from the compound of Formula A-7 by reductive alkylation. For example, treatment of the compound of Formula A-7 with an aldehyde and a reducing agent in the presence of 3 Å molecular sieves in a suitable organic solvent, such as methanol, ethanol and 1,2-dichloroethane. Preferred reducing agents are sodium cyanoborohydride, sodium triacetoxyborohydride and sodium borohydride.

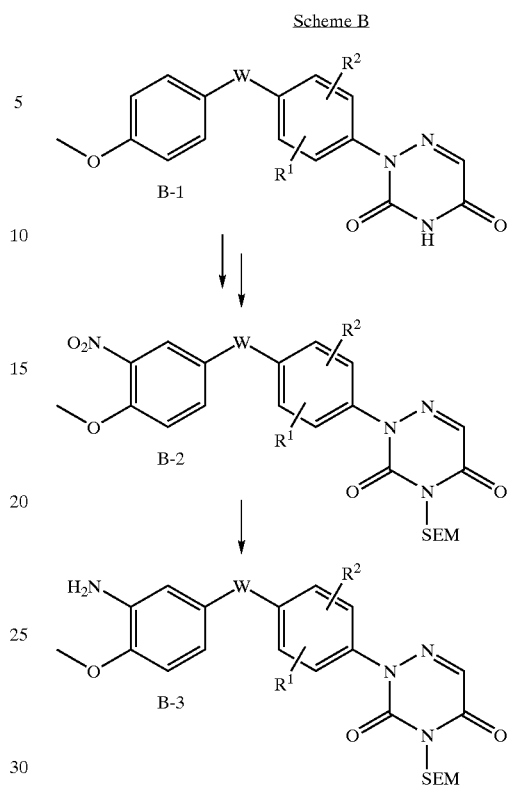

Scheme B

The compound of Formula B-1 is converted to the nitro compound of Formula B-2 using nitric acid in acetic acid. The hydrogen on the nitrogen of the 6-aza-uracil ring is protected by reacting it with sodium hydride and 2-(trimethylsilyl)ethoxymethyl chloride (SEM) in DMF. This compound is then reduced to the corresponding aniline of Formula B-3 by, for example, catalytic hydrogenation (palladium/carbon catalyst in ethyl acetate) or chemical reduction with zinc dust or tin (II) chloride. The aniline of Formula B-3 is used as the starting material in Schemes B-1 through B-5.

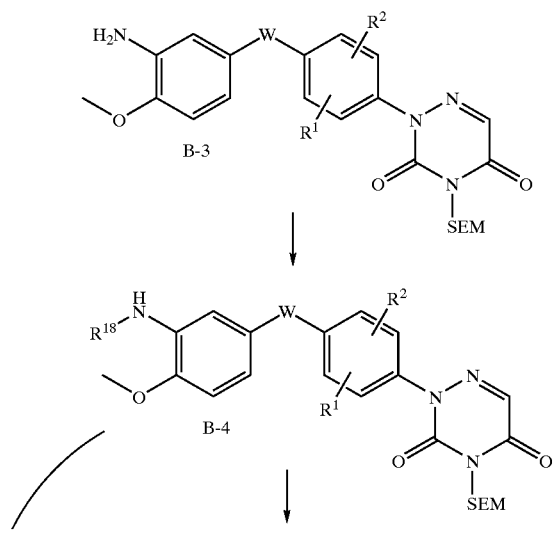

Scheme B-1

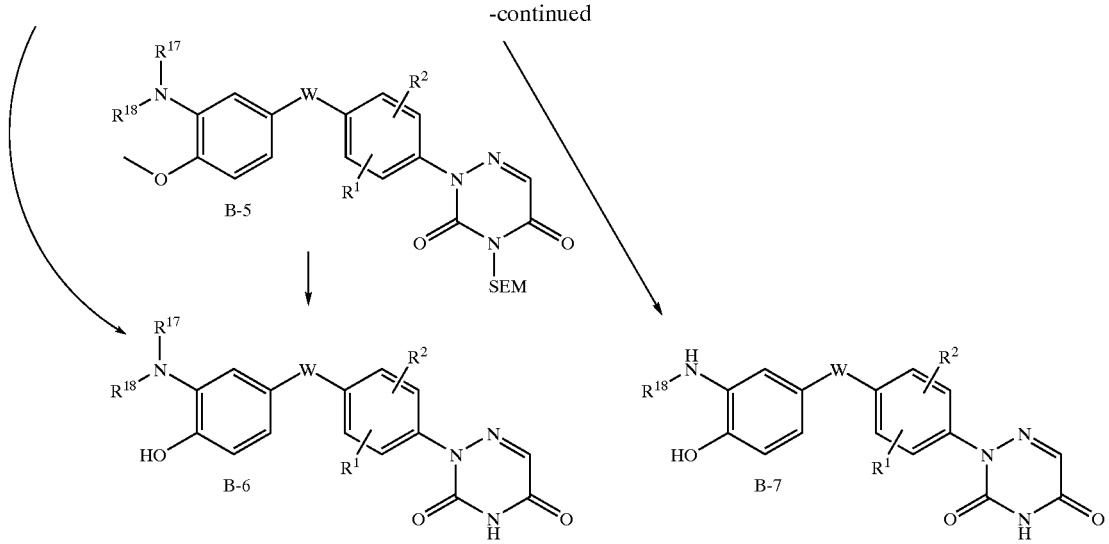

Scheme B-1

The compound of Formula B-3 is converted to the compounds of Formula B-4 and B-5 wherein $R^{17}$ and $R^{18}$ are as defined above by methods known in the art. A preferred method utilizes reductive amination, which is accomplished by the reaction of a suitable aldehyde or a suitable ketone with a compound of Formula B-3 and a reducing agent in a suitable solvent to give the compound of Formula B-4. This reaction is preferably performed in the presence of 3 Å molecular sieves. Preferred reducing agents are sodium cyanoborohydride, sodium triacetoxyborohydride and sodium borohydride. Preferred organic solvents include EtOH, MeOH and 1,2-dichloroethane. Likewise, the compound of Formula B-4 is converted to the compound of Formula B-5 by reductive amination using the conditions described above.

The compound of Formula B-4 is demethylated and deprotected using a suitable boron trihalide, such as boron trichloride or boron tribromide, in a suitable organic solvent such as 1,2-dichloroethane or 1,2-dichloromethane, to give the compound of Formula B-7. Likewise, the compound of Formula B-5 is demethylated and deprotected using similar conditions to give the compound of Formula B-6.

Scheme B-2

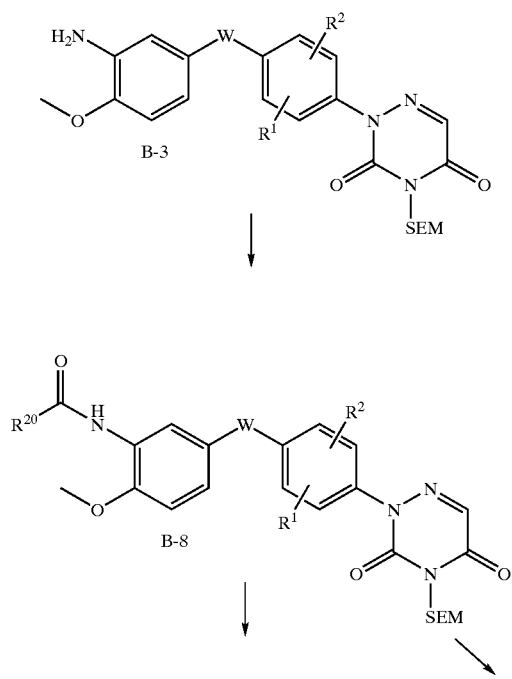

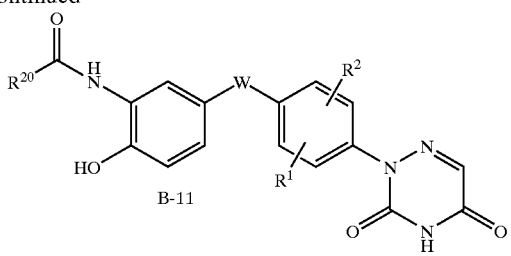

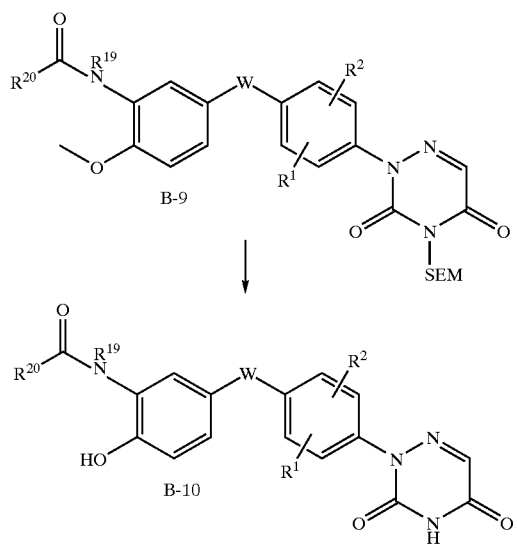

Scheme B-2

The compound of Formula B-3 is acylated with carbonyl chloride (acid chloride) in the presence of a suitable base, such as triethylamine (TEA) or N,N-diisopropylethylamine, to give the compound of Formula B-8. The compound of Formula B-8 is alkylated to give the compound of Formula B-9 wherein $R^{19}$ is, for example, alkyl, using a suitable alkylating agent such as, for example, an alkyl halide, under conditions known in the art and as described above. For example, a preferred alkylation method uses a suitable alkylating agent, such as, for example, an alkyl halide, in the presence of a suitable base, such as, for example, potassium carbonate, sodium hydride, potassium t-butoxide, NaOH or KOH, in a suitable organic solvent, such as, for example, acetone, THF, DMSO, 2-propanol or an aqueous MeOH solution.

The compound of Formula B-9 is demethylated and deprotected using a suitable boron trihalide, such as boron trichloride or boron tribromide, in a suitable organic solvent such as 1,2-dichloroethane or 1,2-dichloromethane, to give the compound of Formula B-10. Likewise, the compound of Formula B-8 is demethylated and deprotected using similar conditions to give the compound of Formula B-11.

Scheme B-3

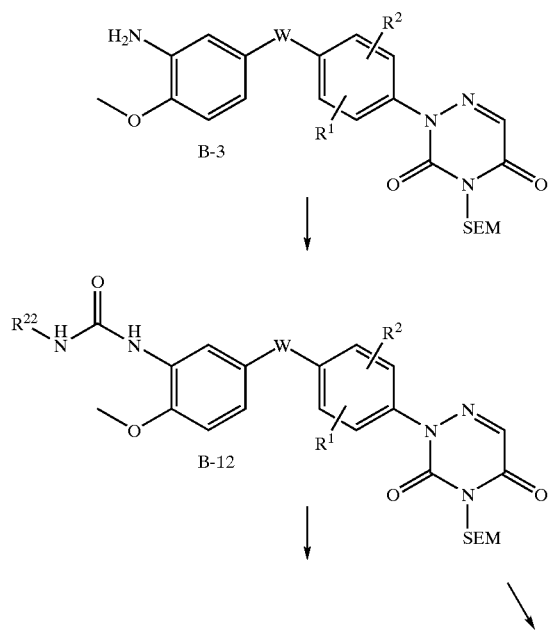

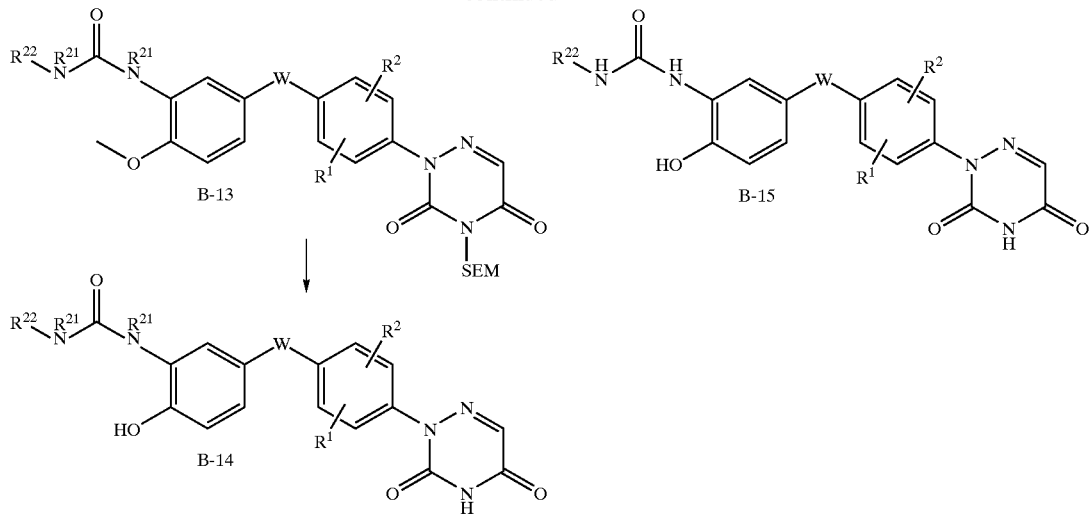

Scheme B-3

The compound of Formula B-3 is reacted with $R^{21}NCO$ and a base such as triethylamine or N,N-diisopropylethylamine in methylene chloride to give the urea compound of Formula B-12. The compound of Formula B-12 is alkylated to give the compound of Formula B-13 using a suitable alkylating agent such as, for example, an alkyl halide, under conditions known in the art and as described above.

The compound of Formula B-13 is demethylated and deprotected using a suitable boron trihalide, such as boron trichloride or boron tribromide, in a suitable organic solvent such as 1,2-dichloroethane or 1,2-dichloromethane, to give the compound of Formula B-14. Likewise, the compound of Formula B-12 is demethylated and deprotected using similar conditions to give the compound of Formula B-15.

Scheme B-4

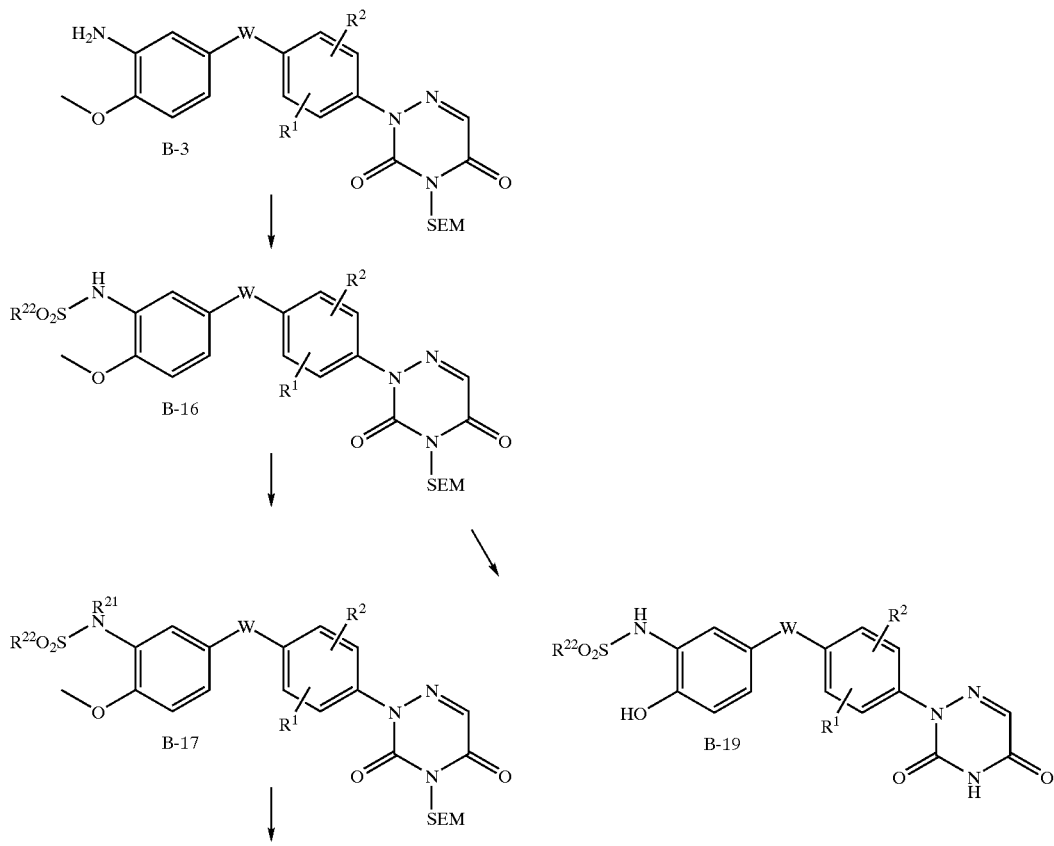

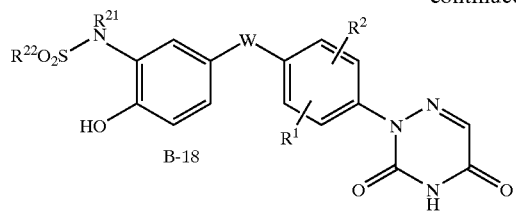

B-18

Scheme B-4

The compound of Formula B-3 is sulfonylated with a sulfonyl chloride in the presence of a suitable base, such as triethylamine (TEA) or N,N-diisopropylethylamine, to give the compound of Formula B-16. The compound of Formula B-16 is alkylated to give the compound of Formula B-17 using a suitable alkylating agent such as, for example, an alkyl halide, under conditions known in the art and as described above. The compound of Formula B-17 is demethylated and deprotected using a suitable boron trihalide, such as boron trichloride or boron tribromide, in a suitable organic solvent such as 1,2-dichloroethane or dichloromethane, to give the compound of Formula B-18. Likewise, the compound of Formula B-16 is demethylated and deprotected using similar conditions to give the compound of Formula B-19.

Scheme B-5

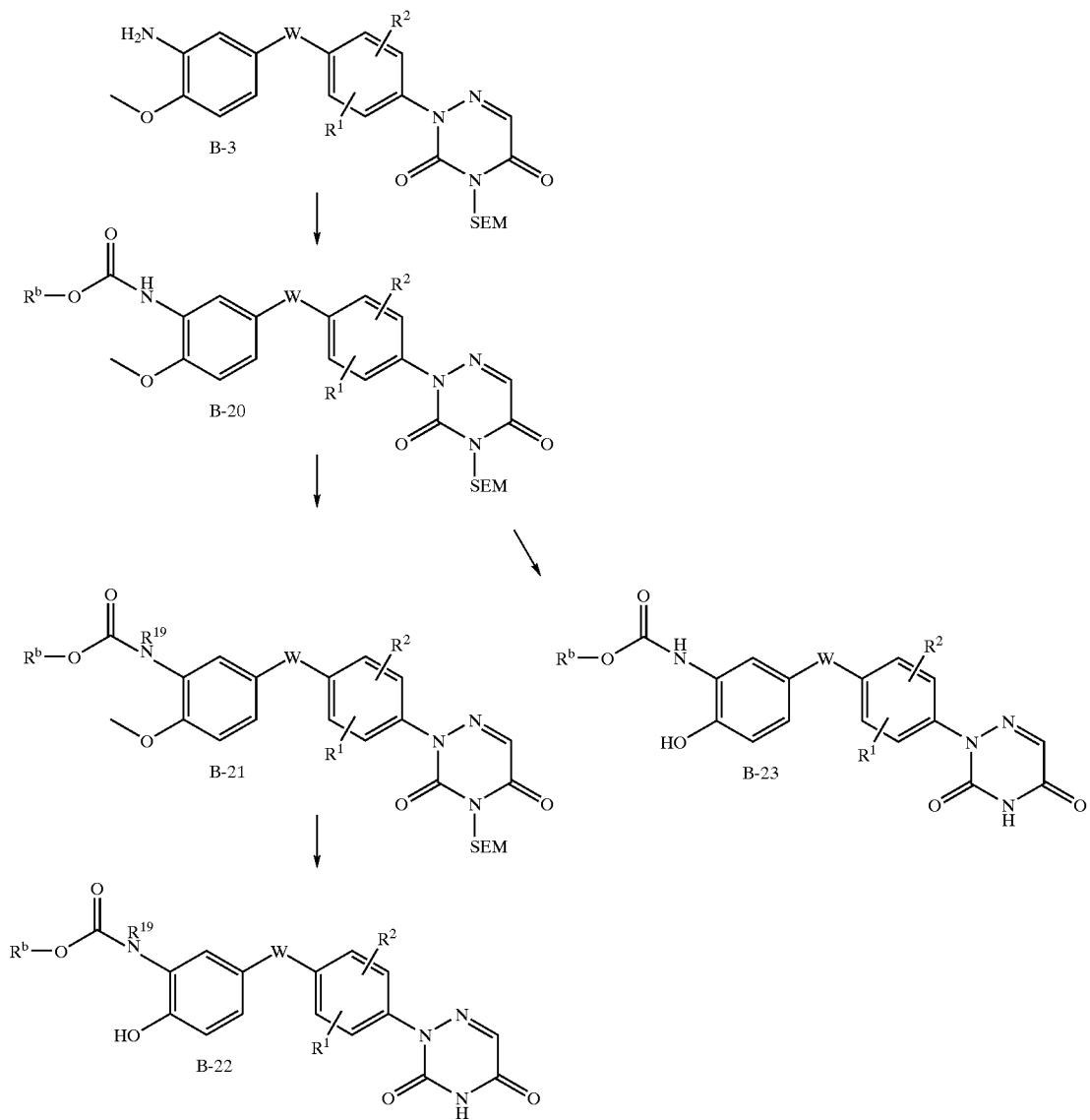

Scheme B-5

The compound of Formula B-3 is reacted with $R^b$—OC(O)Cl wherein $R^b$ is, for example, alkyl or aryl, in the presence of a suitable base, such as triethylamine (TEA) or N,N-diisopropylethylamine, to give the compound of Formula B-20. The compound of Formula B-20 is alkylated to give the compound of Formula B-21, wherein $R^{19}$ is, for example, alkyl, using a suitable alkylating agent such as, for example, an alkyl halide, under conditions known in the art and as described above.

The compound of Formula B-21 is demethylated and deprotected using a suitable boron trihalide, such as boron trichloride or boron tribromide, in a suitable organic solvent such as 1,2-dichloroethane or dichloromethane, to give the compound of Formula B-22. Likewise, the compound of Formula B-20 is demethylated and deprotected using similar conditions to give the compound of Formula B-23.

Scheme C

The compound of Formula C-1 is reacted with chlorosulfonic acid at 0° C. to room temperature to obtain the chlorosulfonylated compound of Formula C-2. The compound of Formula C-2 is reacted with a primary amine of Formula $R^{22}NH_2$ in a suitable solvent, such as, for example, dichloromethane, THF, MeOH, EtOH or acetonitrile, in the presence of a suitable base, such as, for example, TEA or diisopropylethylamine, to give the compound of Formula C-3. Likewise, the compound of Formula C-2 is reacted with a secondary amine of Formula $R^{22}R^{21}NH$ under similar conditions to give the compound of Formula C-4.

The compound of Formula C-3 is demethylated using a suitable boron trihalide, such as boron trichloride or boron tribromide, in a suitable organic solvent, such as 1,2-

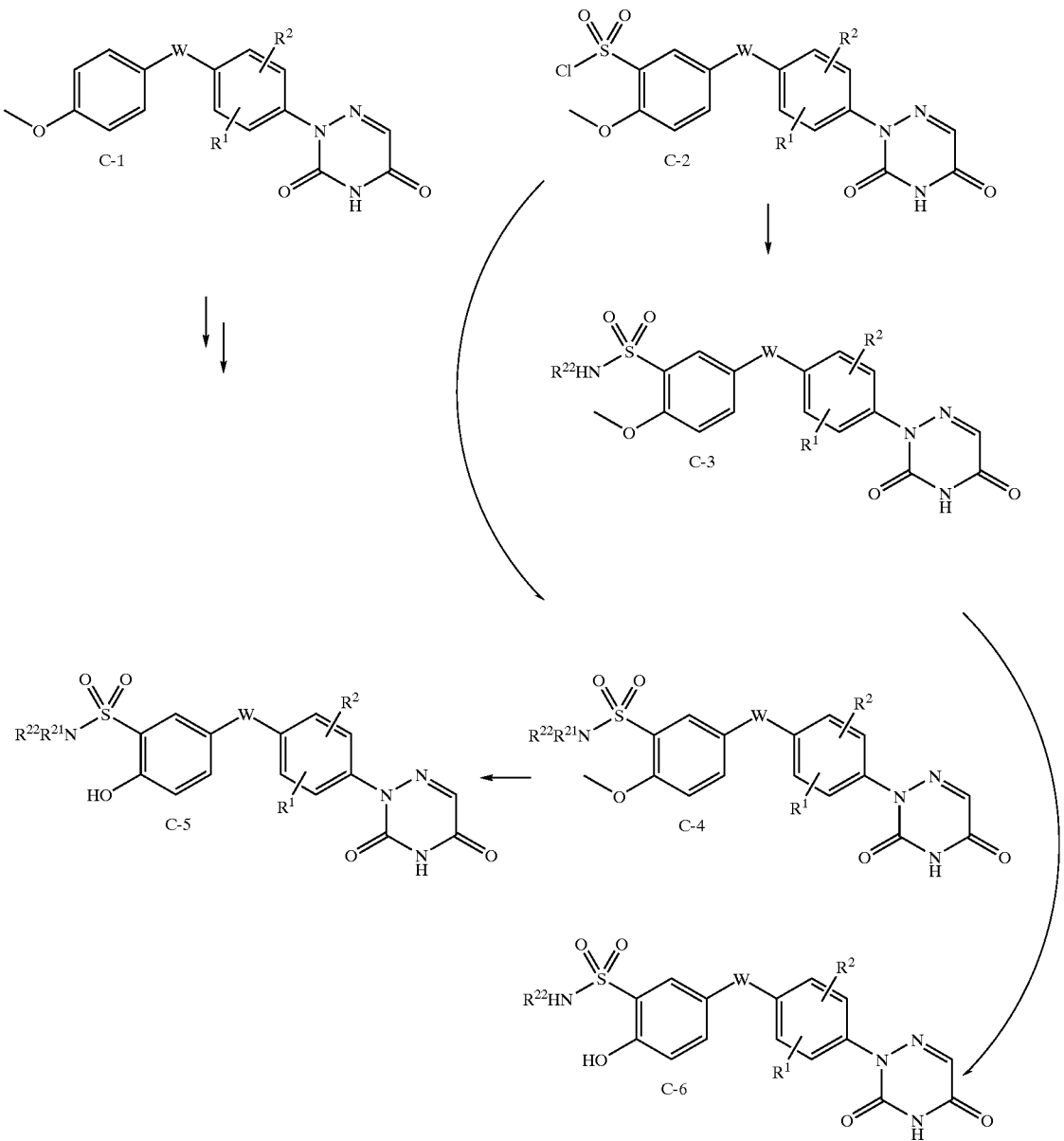

Scheme C dichloroethane or dichloromethane, to give the compound of Formula C-6. Likewise, the compound of Formula C-4 is demethylated using similar conditions to give the compound of Formula C-5.

Alternatively, the compound of Formula C-1 is converted directly to the compound of Formula C-5 by demethylating it and then reacting it with chlorosulfonic acid and a secondary amine, as described above.

Scheme D

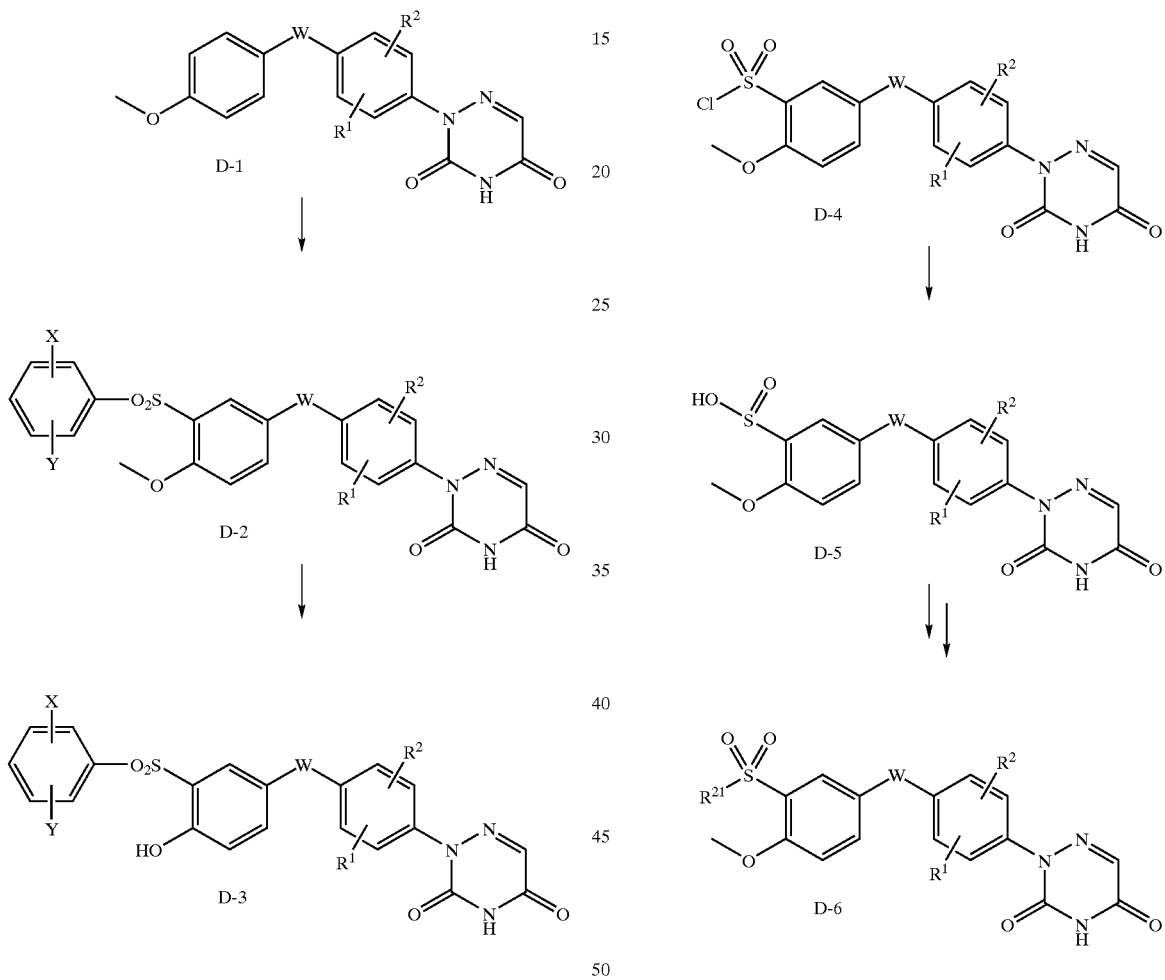

Scheme D

The compound of Formula D-1 is reacted with arylsulfonic acid, wherein the aryl is optionally substituted with X and Y, which are groups independently selected from the Group Z, as defined above, in the presence of a dehydrating agent, preferably $P_2O_5$ in methanesulfonic acid or polyphosphoric acid, at an elevated temperature to give the compound of Formula D-2. This compound of Formula D-2 is demethylated using a suitable boron trihalide, such as boron trichloride or boron tribromide, in a suitable organic solvent such as 1,2-dichloroethane or dichloromethane, to give the compound of Formula D-3.

Scheme D-1

Scheme D-1

The compound of Formula D-1 is reacted with chlorosulfonic acid to give the chlorosulfonated compound of Formula D-4. The compound of Formula D-4 is reduced to the sulfinic acid of Formula D-5 using a suitable reducing agent, such as sodium sulfite in the presence of a base such as sodium bicarbonate or sodium hydroxide. Treatment of the sulfinic acid of Formula D-5 with an alkyl halide in the presence of a base such as, for example, NaOH, KOH, potassium t-butoxide, sodium hydride or sodium methoxide, and then demethylation using standard methods known in the art and as described above, provides the sulfone of Formula D-6 wherein $R^{21}$ is, for example, alkyl.

Scheme E

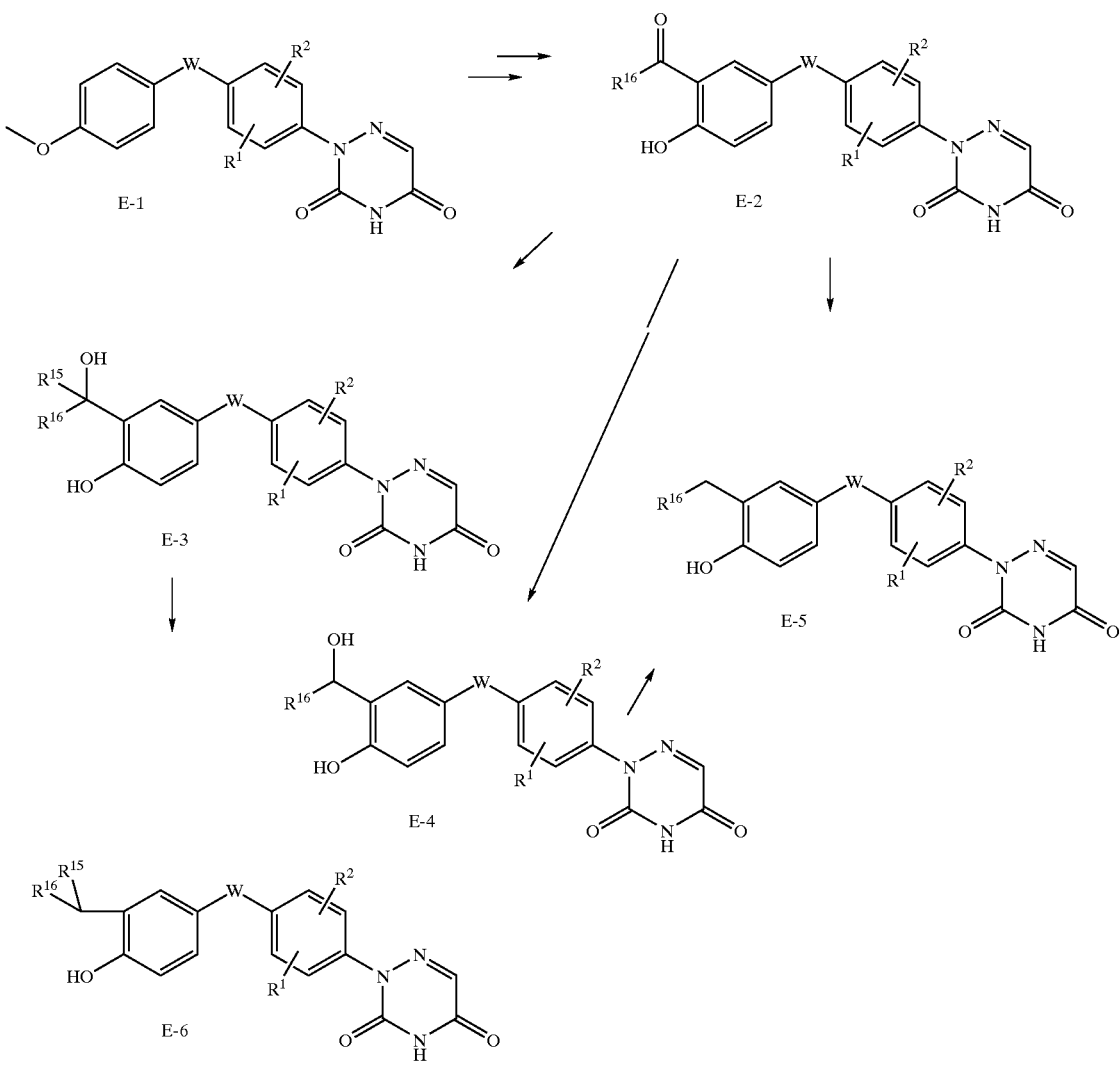

Scheme E

The compound of Formula E-1 is reacted with a carboxylic acid in conjunction with phosphorus pentoxide and methanesulfonic acid or polyphosphoric acid at elevated temperatures. It is then demethylated using standards methods known in the art and as described above to provide the compound of Formula E-2.

The compound of Formula E-2 is reacted with $R^{15}MgX$, wherein X is halo, or $R^{15}Li$ in an aprotic solvent, such as dichloromethane or THF, to afford the alcohol of Formula E-3. The alcohol of Formula E-3 is reacted with a reducing agent, for example, triethylsilane in the presence of an acid, for example, trifluoroacetic acid at 0° C. to 25° C. to give the compound of Formula E-6.

The compound of Formula E-2 is reacted with sodium borohydride in methanol to give the alcohol of Formula E-4. The compound of Formula E-2 is reacted with triethylsilane in trifluoroacetic acid to give the compound of Formula E-5. Likewise, the compound of Formula E-4 is converted to the compound of Formula E-5 using similar conditions.

Schemes F and G describe the preparation of a compound of Formula I wherein $R^4$ is located at the 3' position and $R^3$ is located at the 2' position, and $R^4$ and $R^3$ are taken together with the phenyl ring to form, for example, an indanyl or tetrahydronaphthalyl. Further, Scheme H describes the preparation of a compound of Formula I wherein $R^4$ is located at the 3' position and $R^5$ is located at the 4' position and $R^4$ and $R^5$ are taken together to form, for example, a pyrrolyl. The pyrrolyl ring taken together with the phenyl ring forms an indolyl.

Scheme F

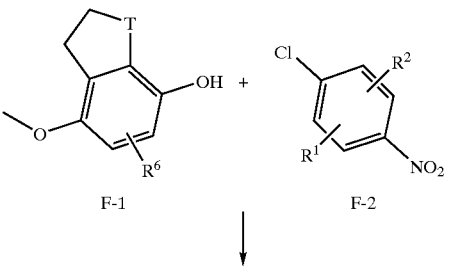

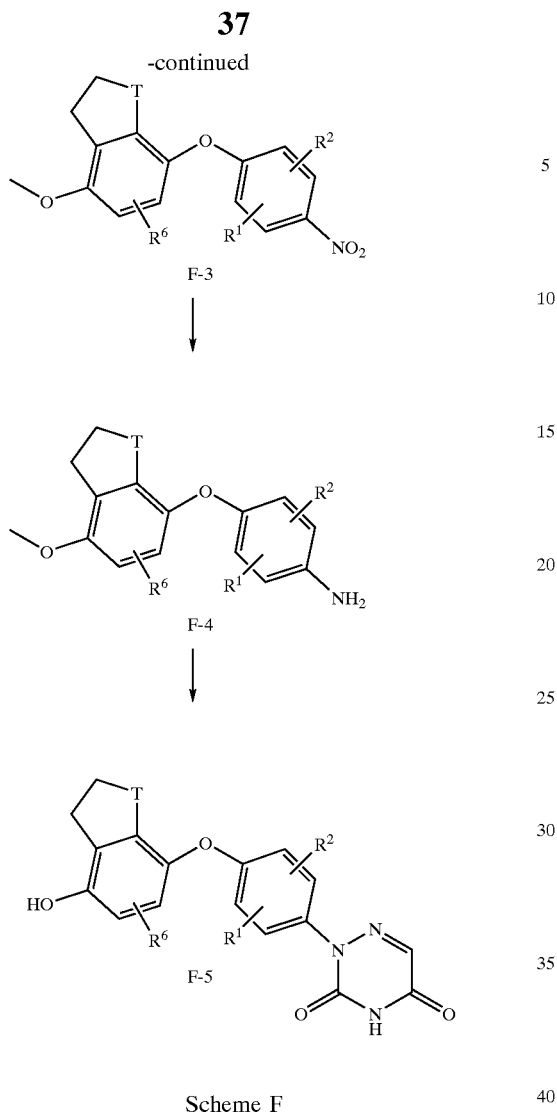

F-3

F-4

F-5

Scheme F

The compounds of Formula F-1 through F-4 are prepared according to procedures analogous to those described above in accordance with well known methods in the art. For example, the compound of Formula F-1, which is prepared according to literature procedures, is coupled to the compound of Formula F-2 using potassium t-butoxide in DMSO at 60–80° C. to give the compound of Formula F-3. Alternatively, this coupling is achieved using potassium carbonate and methyethylketone at refluxing temperature.

The compound of Formula F-3 is reduced to the corresponding aniline compound of Formula F-4 using, for example, catalytic hydrogenation (palladium/carbon catalyst in ethyl acetate). The aniline of Formula F-4 is converted to the corresponding 6-aza-uracil compound of Formula F-5 using literature procedures, such as in M. W. Miller et al., *J. Med. Chem.* 1981, 24, 1337–1342, as described above.

In Scheme F, T completes, as discussed above where $R^3$ and $R^4$ are taken together, a carbocyclic ring A of the Formula —$(CH_2)_b$— or a heterocyclic ring A selected from the group consisting of -Q-$(CH_2)_c$— and —$(CH_2)_j$-Q-$(CH_2)_k$— wherein b, Q, c, j and k are as described above, and wherein said carbocyclic ring A and said heterocyclic ring A are each independently optionally substituted with one or more substituents independently selected from, for example, —$(C_1-C_4)$alkyl, halogen or oxo, as also described above.

Scheme G

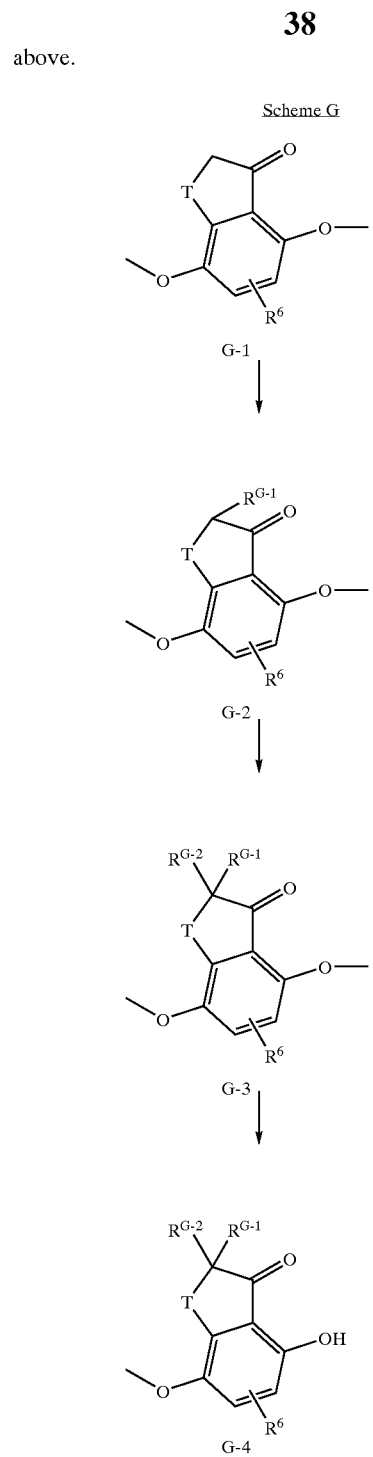

G-1

G-2

G-3

G-4

Scheme G

Treatment of the compounds of Formula G-1 and G-2 with a strong base such as, for example, lithium hexamethyldisilizane, lithium diisopropylamide or potassium t-butoxide and a suitable alkyl halide in an aprotic solvent, for example, THF, affords the bis-alkylated intermediate of Formula G-3. This process is carried out in a stepwise manner where $R^{G-1}$ and $R^{G-2}$ are different, and in a single reaction flask where $R^{G-1}$ and $R^{G-2}$ are the same.

One of the methyl ethers present in the compound of Formula G-3 is selectively deprotected by utilizing boron trichloride or aluminum chloride in an aprotic solvent, for example, dichloromethane or toluene, to give the major product of Formula G-4.

Reduction of the ketone functionality present in the compound of Formula G-4 is accomplished by treatment with a hydrosilane, preferably, triethylsilane, in the presence of an acid, for example, methanesulfonic acid or TFA, with or without a solvent present. Solvents are either protic or aprotic, with dichloromethane being preferred. Those skilled in the art will understand from the present disclosure how to convert the resultant reduced compounds to the target 6-aza-uracil derivatives of the present invention, as described above. In Scheme G, T is as described above for Scheme F.

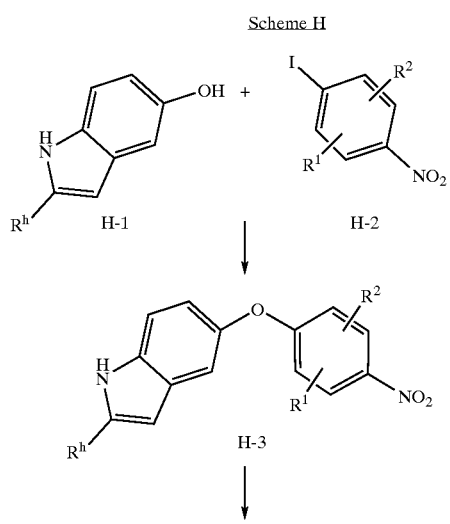

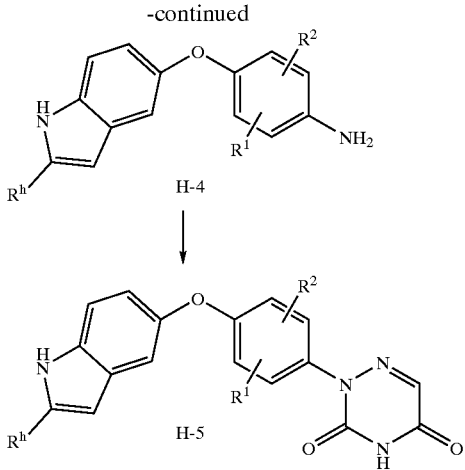

Scheme H

The indole of Formula H-3, wherein $R^h$ is, for example, hydrogen or alkyl, is prepared by coupling the 5-hydroxy indole of Formula H-1, which is commercially available or which can be prepared by methods known in the art, with the 4-iodonitrobenzene of Formula H-2 at about 125° C. in the presence of potassium carbonate for about 3 h. The compound of Formula H-3 is reduced to the corresponding aniline compound of Formula H-4 using, for example, catalytic hydrogenation (palladium/carbon catalyst in ethanol). The aniline of Formula H-4 is converted to the corresponding 6-aza-uracil compound of Formula H-5 using literature procedures, as described above.

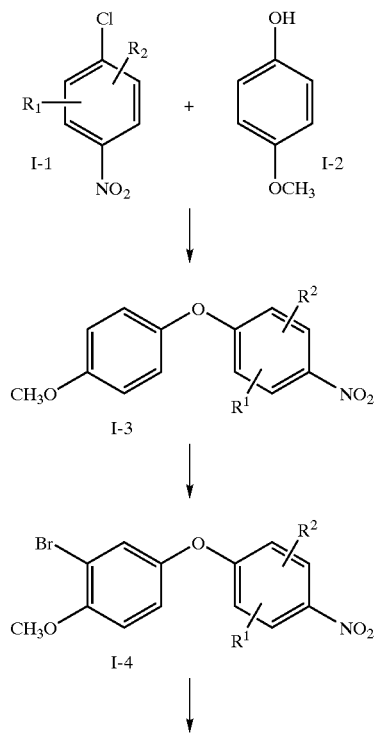

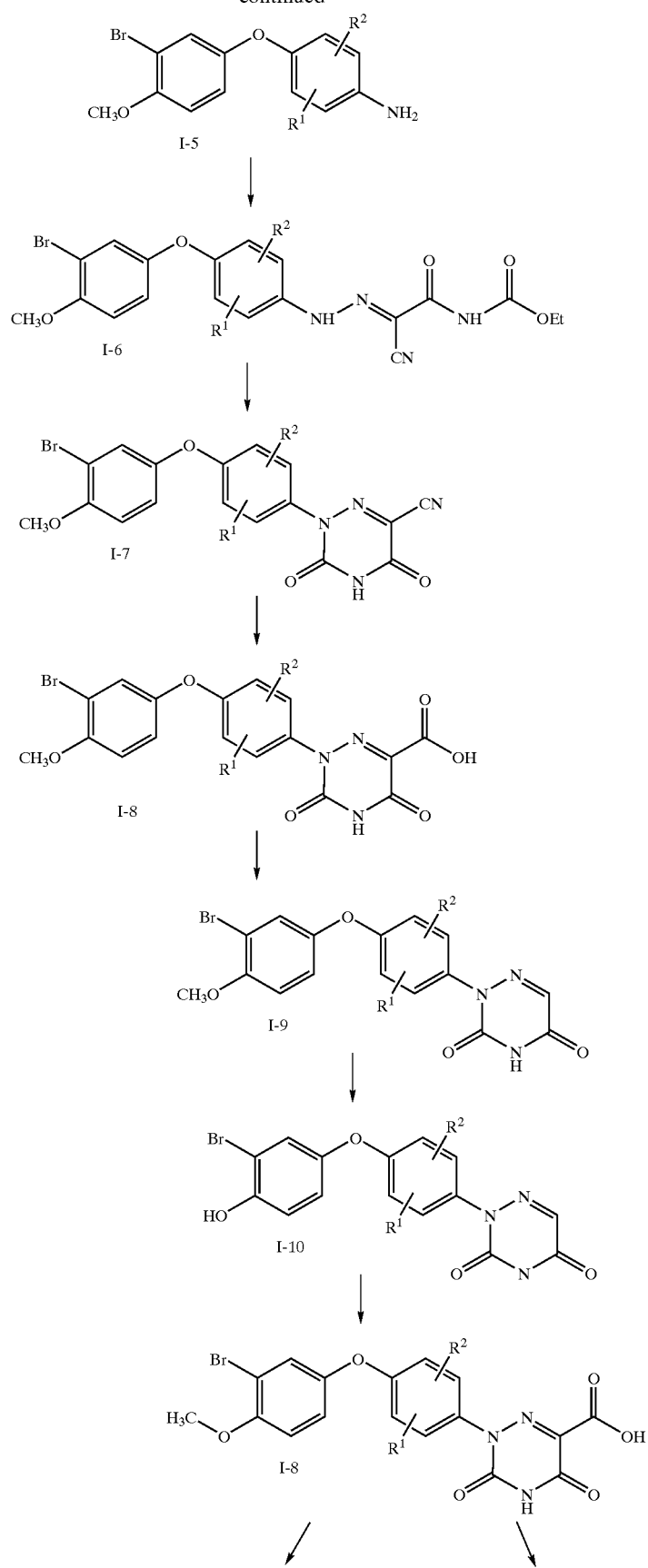

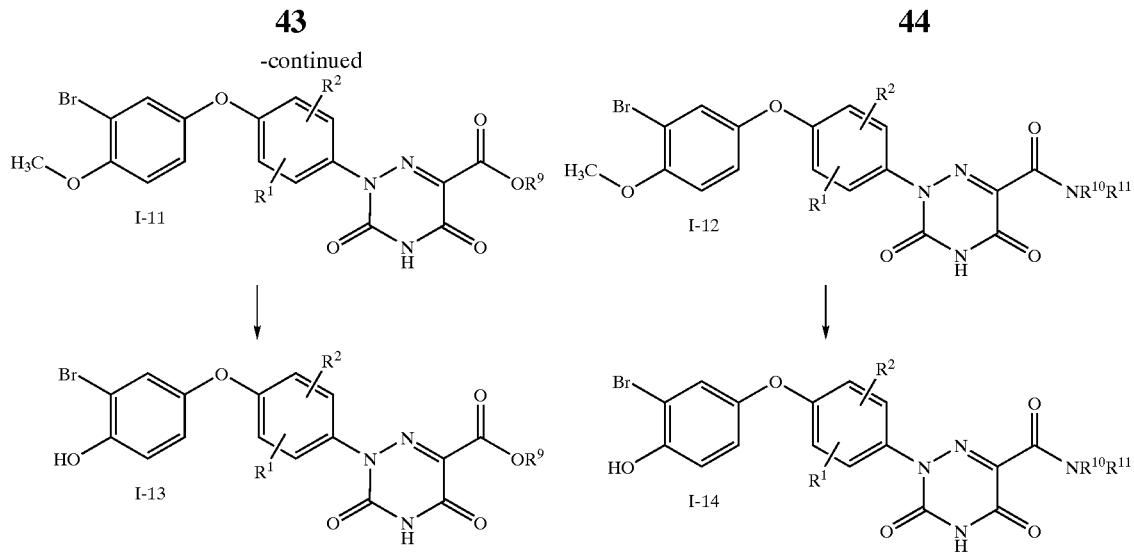

Scheme I

The compounds of Scheme I are prepared according to procedures analogous to those described above in accordance with well known methods in the art. For example, 4-methoxyphenol of Formula I-2 is coupled to the compound of Formula I-1 using potassium t-butoxide in DMSO at 80–100° C. to give the compound of Formula I-3.

The compound of Formula I-3 is brominated to give the compound of Formula I-4 using, for example, N-bromosuccinimide and trifluoroacetic acid in chloroform at reflux. The compound of Formula I-4 is reduced to the corresponding aniline compound of Formula I-5 using, for example, catalytic hydrogenation (palladium/carbon catalyst in ethyl acetate). The aniline of Formula I-5 is diazotized using, for example, sodium nitrite in hydrochloric acid at 0° C., and the resulting diazonium salt is treated with ethylcyanoacetylurethane in pyridine to afford the compound of Formula I-6.

The compound of Formula I-6 is cyclized to give the compound of Formula I-7 using potassium acetate/acetic acid at elevated temperature. The resulting cyano compound of Formula I-7 is converted to the carboxy compound of Formula I-8 using hydrochloric acid/acetic acid at elevated temperature. The carboxy compound of Formula I-8 is decarboxylated using, for example, thioacetic acid at elevated temperature to give the compound of Formula I-9. The compound of Formula I-9 is demethylated using a suitable boron trihalide, such as boron trichloride or boron tribromide, in a suitable organic solvent such as 1,2-dichloroethane or dichloromethane, to give the compound Formula I-10.

To each alcohol of Formula $R^9OH$ in a suitable solvent is added sequentially solutions of the compound of Formula I-8, 1,3-diisopropylcarbodiimide (DIC), and 4-dimethylaminopyridine (DMAP), to give the esters of Formula I-11, wherein $R^9$ is as defined above. A suitable solvent is, for example, DMF.

To each amine of Formula $HNR^{10}R^{11}$ in a suitable solvent is added sequentially solutions of the compound of Formula I-8, N-methylmorpholine (NMM) and O-benzotriazol-1-yl-N,N,N',N'-tetramethyluronium hexafluorophosphate (HBTU) to give the amides of Formula I-12 wherein $R^{10}$ and $R^{11}$ are as defined above. A suitable solvent is, for example, 10% DMF/DCE.

The compounds of Formula I-11 and I-12 are demethylated using a suitable boron trihalide, such as boron trichloride or boron tribromide, in a suitable organic solvent such as 1,2-dichloroethane or dichloromethane, to give the corresponding compounds of Formula I-13 and I-14, respectively.

Scheme J

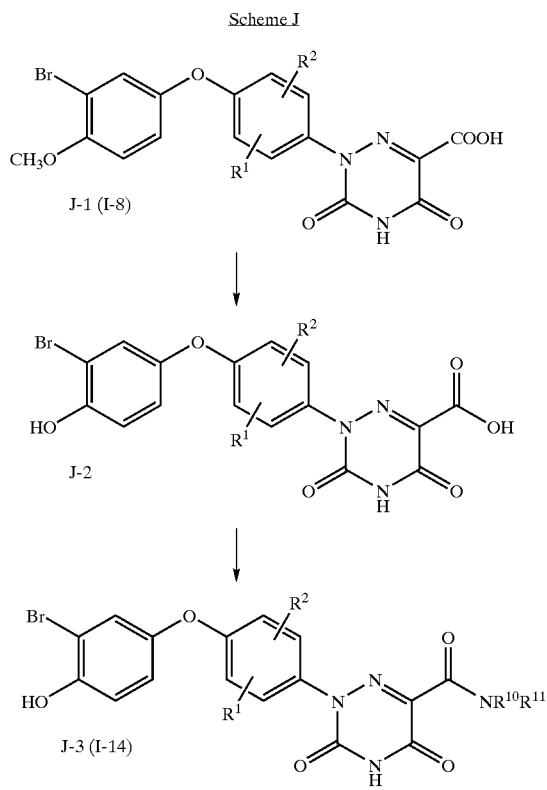

Scheme J

Scheme J shows an alternative scheme for making the demethylated amides of Formula I-14 in Scheme I. The compound of Formula J-1, which is prepared as the compound of Formula I-8 in Scheme I, is demethylated using a suitable boron trihalide, such as boron trichloride or boron tribromide, in a suitable organic solvent such as 1,2-dichloroethane or dichloromethane, to give the compound of Formula J-2.

To each amine of Formula HNR[10]R[11] in a suitable solvent is added sequentially solutions of the compound of Formula J-2, HBTU and Hunigs base (N,N-diisopropylethylamine) to give the amides of Formula J-3. A suitable solvent is, for example, DMF.

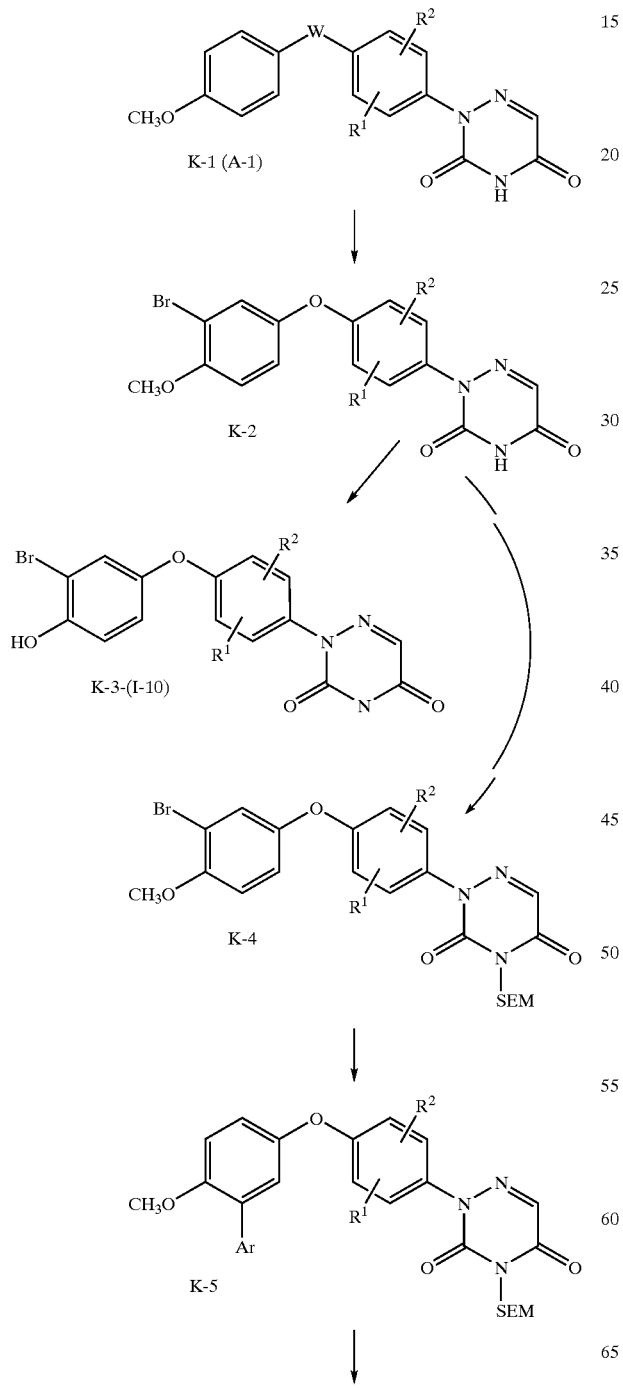

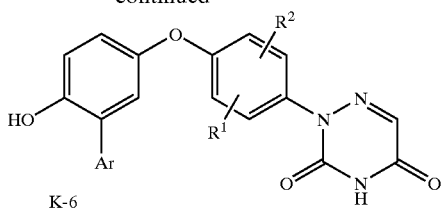

Scheme K

Scheme K shows an alternative method for making the compounds of formula I-10 in Scheme I. The compound of Formula K-1, which is the compound of Formula A-1 in Scheme A, is brominated using conditions known in the art, such as N-bromosuccinimide and trifluoroacetic acid, in a suitable organic solvent, such as chloroform, to obtain the compound of Formula K-2.

The compound of Formula K-2 is demethylated using a suitable boron trihalide, such as boron trichloride or boron tribromide, in a suitable organic solvent such as 1,2-dichloroethane or dichloromethane, to give the compound of Formula K-3 (I-10). The compound of Formula K-2 is protected by reacting it with, for example, sodium hydride, SEM chloride, and tetra-n-butylammonium iodide in DMF to afford the compound of Formula K-4. This compound is coupled to an organoboronic acid, such as phenylboronic acid, in the presence of a palladium catalyst, such as tetrakis(triphenylphosphine)palladium(0) and a base, such as aqueous sodium carbonate, in a suitable organic solvent such as DMF or 1,2-dichloroethane, to afford the compound of Formula K-5, wherein Ar represents an aryl group.

The compound of Formula K-5 is demethylated and deprotected using a suitable boron trihalide, such as boron trichloride or boron tribromide, in a suitable organic solvent such as 1,2-dichloroethane or dichloromethane, to give the compound of Formula K-6, wherein Ar represents an aryl group.

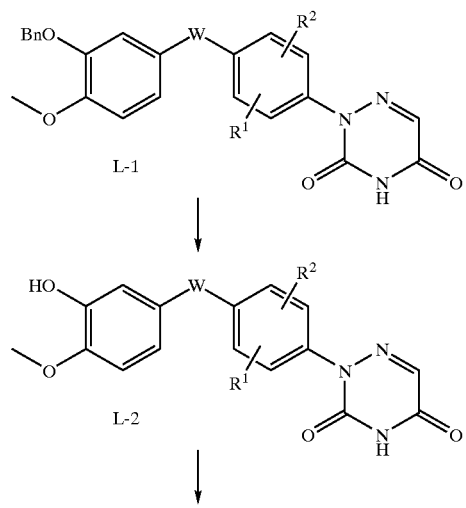

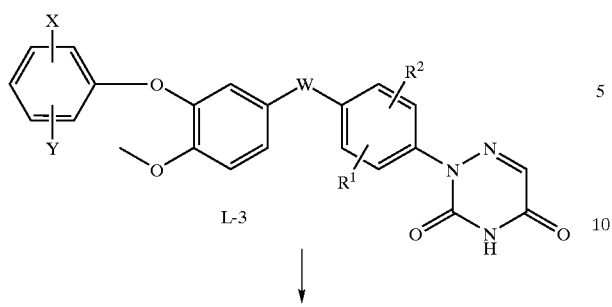

L-3

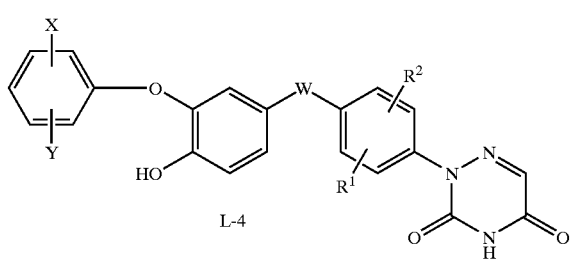

L-4

Scheme L

The benzyl ether of Formula L-1 is converted to the phenol of Formula L-2 by debenzylation. Treatment of the benzyl ether of Formula L-1 with thioanisole in TFA at ambient temperature affords the phenol of Formula L-2. Conversion of the phenol of Formula L-2 to the phenyl ether of Formula L-3 is accomplished by coupling the phenol of Formula L-2 with aryliodonium tetrafluoroborate and copper bronze in the presence of triethyl amine in dichloromethane or coupling the phenol of Formula L-2 with arylboronic acid and copper (II) acetate in the presence of a suitable base such as, for example, TEA, pyridine, or a mixture of TEA and pyridine. Conversion of the phenyl ether of Formula L-3 to the compound of Formula L-4 is accomplished by demethylation according to procedures analogous to those described above. The moieties X and Y are groups independently selected from the Group Z, which is as defined above.

Scheme M

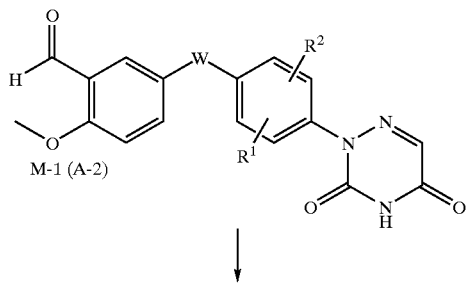

M-1 (A-2)

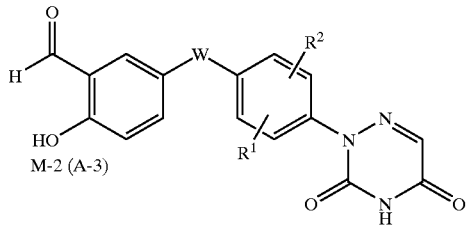

M-2 (A-3)

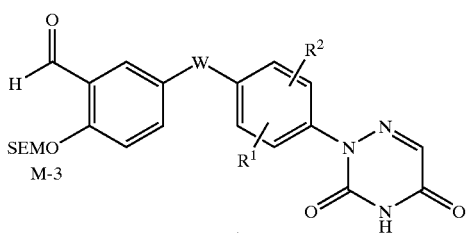

M-3

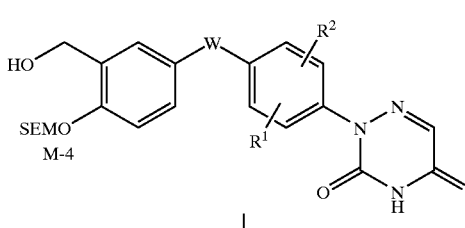

M-4

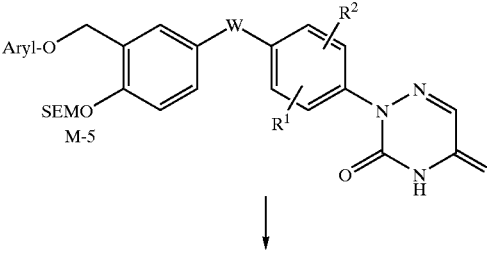

M-5

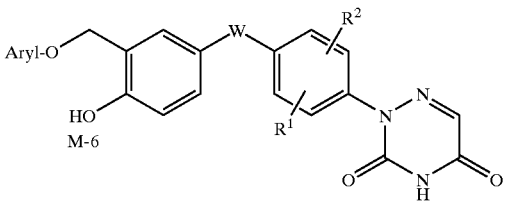

M-6

Scheme M

The methyl ether of Formula M-1 and the phenol of Formula M-2 are prepared as described in Scheme A, specifically, they are prepared as the compounds of Formula A-2 and A-3, respectively, in Scheme A. The phenol of Formula M-2 is protected as the trimethylsilylethoxymethyl ether of Formula M-3 by treatment with a strong base such as, for example, sodium hydride or potassium t-butoxide in an aprotic solvent, e.g., THF, followed by treatment with trimethylsilylethoxymethyl chloride ("SEMCl").

Treatment of the aldehyde of Formula M-3 with a reducing agent such as, for example, diisobutylaluminum hydride ("DIBALH") in an aprotic solvent, e.g., dichloromethane or THF affords the alcohol of Formula M-4. Reaction of the alcohol of Formula M-4 with a suitable phenol utilizing an azodicarbonyl compound, e.g., 1,1'-(azodicarbonyl) dipiperidine or diethylazo-dicarboxylate, and a phosphine such as, for example, triphenyl- or tributylphosphine, in an aprotic solvent, e.g., THF or toluene, provides the ether of Formula M-5. Removal of the "SEM" protecting group present in the compound of Formula M-5 under acidic conditions such as, for example, sulfuric or mineral acid in an alcoholic solvent, e.g., MeOH or EtOH, or alternatively, fluoride-mediated conditions (tetrabutylammonium fluoride/THF, hydrogen fluoride/acetonitrile) affords the phenol of Formula M-6.

In the preparation of the compounds of Formula I it is noted that, as would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991. Suitable protecting groups for any particular functionality would include those which are not substantially chemically reactive under the reaction conditions described and which are removed without substantially chemically altering other functionalities of any given intermediate of the compound of Formula I, or of the compound of Formula I itself. The protecting group can be removed as so desired in any given preparation method, e.g., in a subsequent step.

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

The characteristics of patients at risk of having atherosclerosis are well known to those in the art and include patients who have a family history of cardiovascular disease, including hypertension and atherosclerosis, obese patients, patients who exercise infrequently, patients with hypercholesterolemia, hyperlipidemia and/or hypertriglyceridemia, patients having high levels of LDL or Lp(a), patients having low levels of HDL, and the like.

Patients at risk of developing diabetes include patients who have a family history of diabetes, obese patients, patients who exercise infrequently, patients who have polycystic ovary syndrome, impaired glucose tolerance or exhibit insulin resistance, and patients who have or have had gestational diabetes. The preferred type of diabetes to be treated by the compounds of the present invention is non-insulin dependent diabetes mellitus, also known as Type II diabetes or NIDDM. It is also noted that the complications associated with diabetes can be treated or prevented through the methods disclosed herein.

In one aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the diabetic complications, such as neuropathy, nephropathy, retinopathy or cataracts.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention along with other agents that can be used to treat diabetes.

Representative agents that can be used to treat diabetes in combination with a compound of the present invention include insulin and insulin analogs (e.g. LysPro insulin); GLP-1 (7-37) (insulinotropin) and GLP-1 (7-36)—NH$_2$; sulfonylureas and analogs: chlorpropamide, glibenclamide, tolbutamide, tolazamide, acetohexamide, Glypizide®, glimepiride, repaglinide, meglitinide; biguanides: mefformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, BRL49653; fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex; antiobesity agents: fenfluramine; vanadate and vanadium complexes (e.g. Naglivan®) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with a compound of the present invention are pramlintide (symlin™), AC 2993 and nateglinide. Any combination of agents can be administered as described above.

In addition, the compounds of the present invention can be used in combination with aldose reductase inhbitiors, glycogen phosphorylase inhibitors, sorbitol dehydrogenase inhibitors, NHE-1 inhibitors and glucocorticoid receptor antagonists.

The compounds of the present invention can be used in combination with aldose reductase inhibitors. Aldose reductase inhibitors constitute a class of compounds that have become widely known for their utility in preventing and treating conditions arising from complications of diabetes, such as diabetic neuropathy and nephropathy. Such compounds are well known to those skilled in the art and are readily identified by standard biological tests. For example, the aldose reductase inhibitors, zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S.

Pat. No. 4,492,706 to Kallai-Sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is 1-phthalazineacetic acid, 3,4-dihydro-4-oxo-3-[[5-trifluoromethyl)-2-benzothiazolyl]methyl]-, also known as zopolrestat.

The term aldose reductase inhibitor refers to compounds that inhibit the bioconversion of glucose to sorbitol, which is catalyzed by the enzyme aldose reductase. Any aldose reductase inhibitor may be used in a combination with a compound of the present invention. Aldose reductase inhibition is readily determined by those skilled in the art according to standard assays (J. Malone, *Diabetes*, 29:861–864 (1980). "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, additional examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl}-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);
4. 3-(4-bromo-2-fluorobenzyl)-7-chloro-3,4-dihydro-2,4-dioxo-1 (2H)-quinazolineacetic acid (zenarestat, U.S. Pat. No. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. No. 4,436,745, U.S. Pat. No. 4,438,272);
14. 2,7-di-fluoro-5-methoxy-spiro(9H-fluorene-9,4'-imidazolidine)2',5'-dione (U.S. Pat. No. 4,436,745, U.S. Pat. No. 4,438,272);
15. 7-fluoro-spiro(5H-indenol[1,2-b]pyridine-5,3'-pyrrolidine)2,5'-dione (U.S. Pat. No. 4,436,745, U.S. Pat. No. 4,438,272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis)(U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below

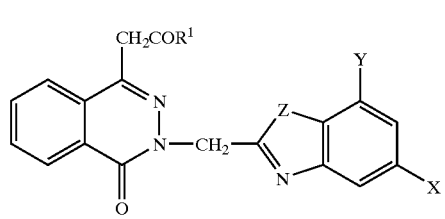

Ia and pharmaceutically acceptable salts and prodrugs thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5-chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF$_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred. Procedures for making the aldose reducatase inhibitors of formula Ia can be found in PCT publication number WO 99/26659.

The compounds of the present invention can also be used in combination with glucocorticoid receptor modulators. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR modulators can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples of GR modulators that can be used in combination with a compound of the present invention include compounds disclosed in commonly assigned U.S. patent application No. 60/132,130, which is hereby incorporated by reference herein.

The compounds of the present invention can also be used in combination with sorbitol dehydrogenase inhibitors. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

Moreover, the compounds of the present invention can be administered in combination with other pharmaceutical agents such as cholesterol biosynthesis inhibitors and cholesterol absorption inhibitors, especially HMG-CoA reductase inhibitors and HMG-CoA synthase inhibitors, HMG-CoA reductase and synthase gene expression inhibitors, CETP inhibitors, biles acid sequesterants, fibrates, ACAT inhibitors, squalene synthetase inhibitors, anti-oxidants and niacin. The compounds of the present invention may also be administered in combination with naturally occurring compounds that act to lower plasma cholesterol levels. These naturally occurring compounds are commonly called nutraceuticals and include, for example, garlic extract and niacin.

Specific cholesterol absorption inhibitors and cholesterol biosynthesis inhibitors are described in detail below. Additional cholesterol absorption inhibitors are known to those skilled in the art and are described, for example, in PCT WO 94/00480.

Any HMG-CoA reductase inhibitor may be employed as an additional compound in the combination therapy aspect of the present invention. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455–509 (1981); and the references cited therein). A variety of these compounds are described and referenced below. U.S. Pat. No. 4,231,938 discloses certain compounds isolated after cultivation of a microorganism belonging to the genus *Aspergillus*, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyidihydroxyheptenoic acids, such as rivastatin. Also, U.S. Pat. No. 4,647,576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors include Baycol®, Lescol®, Lipitor®, Mevacor®, Pravachol® and Zocor®.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology*, 35: 155–160 (1975); and *Methods of Enzymology*, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors useful in the methods, compositions and kits of the present invention will be known to those skilled in the art.

Any compound that decreases HMG-CoA reductase gene expression may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9–19 1985). Several such compounds are described and referenced below; however, other inhibitors of HMG-CoA reductase gene expression will be known to those skilled in the art, for example, U.S. Pat. No. 5,041,432 discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.*, 32:357–416 1993).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively.

Any ACAT inhibitor can serve as the second compound in the combination therapy aspect of this invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the present invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology*, 15:393–454 (1969); and *Methods of Enzymology*, 110: 359–373 (1985); and references cited therein). A summary of squalene synthetase inhibitors has been complied in *Curr. Op. Ther. Patents*, 861–4, (1993). European patent application publication Number 0 567 026 A1 discloses certain 4,1-benzoxazepine derivatives as squalene synthetase inhibitors and their use in the treatment of hypercholesterolemia and as fungicides. European patent application publication Number 0 645 378 A1 discloses certain seven- or eight-membered heterocycles as squalene synthetase inhibitors and their use in the treatment and prevention hypercholesterolemia and fungal infections. European patent application publication Number 0 645 377 A1 discloses certain benzoxazepine derivatives as squalene synthetase inhibitors useful for the treatment of hypercholesterolemia or coronary sclerosis. European patent application publication Number 0 611 749 A1 discloses certain substituted amic acid derivatives useful for the treatment of arteriosclerosis. European patent application publication Number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication Number 0 701 725 A1 discloses a process for preparing certain optically-active compounds, including benzoxazepine derivatives, having plasma cholesterol and triglyceride lowering activities.

Other compounds that are marketed for hyperlipidemia, including hypercholesterolemia and which are intended to help prevent or treat atherosclerosis include bile acid sequestrants, such as Colestid®, LoCholest® and Questran®; and fibric acid derivatives, such as Atromid®, Lopid® and Tricor®. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of the methods, pharmaceutical compositions, and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267, stereoisomers thereof, and pharmaceutically acceptable salts of said compounds and stereoisomers. The compound tetrahydrolipstatin is especially preferred.

The pancreatic lipase inhibitors lipstatin, 2S,3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874.

The pancreatic lipase inhibitor, FL-386, 1-[4-(2-methylpropyl)cyclohexyl]-2-[(phenylsulfonyl)oxy]-ethanone, and the variously substituted sulfone derivatives related thereto, are disclosed in U.S. Pat. No. 4,452,813.

The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor, Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor, valilactone, and a process for the preparation thereof by the microbial cultivation of *Actinomycetes* strain MG147-CF2, are disclosed in Kitahara, et al., *J. Antibiotics*, 40 (11), 1647–1650 (1987).

The lipase inhibitor, esteracin, and certain processes for the preparation thereof by the microbial cultivation of *Streptomyces* strain ATCC 31336, are disclosed in U.S. Pat. Nos. 4,189,438 and 4,242,453.

The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics*, 33, 1594–1596 (1980). The use of ebelactones A and B in the suppression of monoglyceride formation is disclosed in Japanese Kokai 08-143457, published Jun. 4, 1996.

The lipase inhibitor, RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

Any suitable dosage of a lipase inhibitor is used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of the lipase inhibitor which will be most suitable for an individual patient and it will vary with, e.g., age, weight and response of the particular patient. The above dosages of lipase inhibitors are exemplary, but there can be, of course, individual instances where higher or lower dosage ranges of such lipase inhibitors are merited, and all such dosages are within the scope of the present invention.

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed, however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods, pharmaceutical compositions and kits of the instant invention, generally preferred glucosidase inhibitors are those inhibitors that are selected from the group consisting of acarbose, adiposine, voglibose, miglitol, emiglitate, MDL-25637, camiglibose, tendamistate, Al-3688, trestatin, pradimicin-Q and salbostatin.

The glucosidase inhibitor, acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1→4)-O-α-D-glucopyranosyl-(1→4)-D-glucose, the various amino sugar derivatives related thereto and a process for the preparation thereof by the microbial cultivation of *Actinoplanes* strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor, adiposine, consisting of adiposine forms 1 and 2, is disclosed in U.S. Pat. No. 4,254,256. Additionally, a process for the preparation and purification of adiposine is disclosed in Namiki et al., *J. Antiobiotics*, 35, 1234–1236 (1982).

The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559.

The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772.

The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor, camiglibose, methyl 6-deoxy-6-[(2R,3R,4R,5S)-3,4,5-trihydroxy-2-(hydroxymethyl)piperidino]-α-D-glucopyranoside sesquihydrate, the deoxynojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor, tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor, Al-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor, trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273,765.

The glucosidase inhibitor, pradimicin-Q and a process for the preparation thereof by the microbial cultivation of *Actinomadura verrucospora* strains R103-3 or A10102, are disclosed in U.S. Pat. Nos. 5,091,418 and 5,217,877 respectively.

The glycosidase inhibitor, salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091,524.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, Al-3688 and trestatin.

In another aspect of the present invention, the compounds of Formula I can be used in combination with other anti-obesity agents. The additional anti-obesity agent is preferably selected from the group consisting of phenylpropanolamine, ephedrine, pseudoephedrine, phentermine, a neuropeptide Y antagonist, a $β_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, and a ciliary neurotrophic factor.

Especially preferred anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl}acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

Suitable anorectic agents for the compositions, methods and kits of the present invention can be prepared using methods known to those skilled in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Any suitable dosage of an anorectic agent is used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 10 mg/kg body weight of the subject per day. In practice, the physician will determine the actual dosage of the anorectic agent which will be most suitable for an individual patient and it will vary with, e.g., age, weight and response of the particular patient. The above dosages of anorectic agents are exemplary, but there can be, of course, individual instances where higher or lower dosage ranges of such anorectic agents are merited, and all such dosages are within the scope of the present invention.

The compounds of the present invention can also be used in combination with other antihypertensive agents. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®. In addition, diuretics and combinations of the above antihypertensive agents have been employed and are contemplated to be used in combination with compounds of the present invention.

The compounds of the present invention can also be used in combination with antidepressants. Examples of marketed antidepressants that can be used in combination with compounds of the present invention include monoamine oxidase inhibitors such as Nardil®, and Parnate®; selective seratonin reuptake inhibitors, such as Paxil®, Prozac®, and Zoloft®; triclyclics, such as Asendin®, Elavil®, Etrafon®, Limbitrol®, Norpramin® Pamelor®, Sinequan®, Surmontil®, Tofranil®, Triavil®, and Vivactil®. Additional compounds that are used to treat deprression and that can be used in combination with compounds of the present invention include Desyrel®, Effexor®, Remeron®, Serzone®, and Wellbutrin®.

The compounds of the present invention can also be used in combination with compounds used to treat osteoporosis. Examples of marketed products containing active agents that can be used in combination with compounds of the present invention include biphosphonates such as Fosamax® and hormonal agents such as calcitonin and estrogens. In addition, Evista® may be used in combination with compounds of the present invention.

The compounds of the present invention are administered to a patient in a therapeutically effective amount. The compounds can be administered alone or as part of a pharmaceutically acceptable composition. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially. In addition, it should be recognized that the compositions may be different forms. For example, one or more compounds may be delivered via a tablet, while another is administered via injection or orally as a syrup. All combinations, delivery methods and administration sequences are contemplated. For sequential administration, a compound, a prodrug, an isomer or a pharmaceutically acceptable salt of the present invention and another active compound, as the case may be, can be administered in any order. It is generally preferred that such administration be oral. It is even more preferred that the administration be oral and simultaneous. However, for example, if the subject being treated is unable to swallow, or oral absorption is otherwise impaired or undesirable, parenteral or transdermal administration will be appropriate. Where the administration is sequential, the administration of a compound, prodrug, isomer or pharmaceutically acceptable salt of the present invention and another active compound, as the case may be, can be by the same method or by different methods.

The dose of a compound, prodrug, isomer or pharmaceutically acceptable salt of the present invention to be administered to a human or animal is rather widely variable and subject to the judgment of the attending physician or veterinarian. As would be understood by those skilled in the art, it may be necessary to adjust the dose of a compound, prodrug or isomer of this invention when it is administered in the form of a salt, e.g., where the salt forming moiety of which has an appreciable molecular weight. The general range of therapeutically effective amounts of the compounds, prodrugs, isomers or pharmaceutically acceptable salts of the present invention is from about 0.001 mg/kg body weight to about 100 mg/kg body weight of the subject per day. A preferred range of effective administration rates of the compounds, prodrugs, isomers or pharmaceutically acceptable salts of the present invention is from about 0.01 mg/kg body weight to about 50 mg/kg body weight of the subject per day. While it may be practical to administer the daily dose of a compound, prodrug, isomer or pharmaceutically acceptable salt of this invention, in portions, at various hours of the day, in any given case, the amount of compound, prodrug, isomer or pharmaceutically acceptable salt administered will depend on such factors as the solubility of the compound, prodrug, isomer or pharmaceutically acceptable salt of this invention, the formulation used and the route of administration (e.g., oral, transdermal, parenteral or topical).

Dosages of the compounds, prodrugs, isomers and pharmaceutically acceptable salts of the present invention are administered to humans by any suitable route, with oral administration being preferable. Individual tablets or capsules should generally contain from about 0.1 mg to about 100 mg of compound, prodrug, isomer or pharmaceutically acceptable salt of the present invention, in a suitable pharmaceutically acceptable vehicle, diluent or carrier. Dosages for intravenous administration are generally within the range of from about 0.1 mg to about 10 mg per single dose as required. For intranasal or inhaler administration, the dosage is generally formulated as a solution of about 0.1% to about 1% (w/v). In practice, the physician will determine the actual dosage which will be most suitable for an individual patient and it will vary with, e.g., age, weight and response of the particular patient. The above dosages are exemplary of the average case but there can, of course, be individual instances where higher or lower dosage ranges are merited, and all such dosages of compounds of Formula I, prodrugs, isomers and pharmaceutically acceptable salts of the present invention, are within the scope of the present invention.

Any suitable route of administration may be used for the compounds of Formula I, isomers, prodrugs and pharmaceutically acceptable salts thereof, in the present invention. It is usually preferred to administer the compounds, prodrugs, isomers and pharmaceutically acceptable salts of the present invention orally for reasons of convenience; however, they may be administered, for example, percutaneously, or as suppositories for absorption by the rectum, as desired in a given instance. As described above, the administration may be carried out in single or multiple doses, as appropriate.

The compounds, prodrugs, isomers and pharmaceutically acceptable salts of the present invention can be administered as pharmaceutical compositions comprising a pharmaceutically acceptable vehicle, carrier or diluent. The pharmaceutical compositions of the present invention comprise a suitable amount of a compound, prodrug, isomer or pharmaceutically acceptable salt of this invention, i.e., an amount sufficient to provide the desired dosage.

The compounds, prodrugs, isomers and pharmaceutically acceptable salts of this invention are administered in a wide variety of different dosage forms, i.e., they may be combined with various pharmaceutically acceptable inert vehicles, carriers or diluents in any suitable form. Such carriers include solid diluents or fillers, sterile aqueous media and various non-toxic organic solvents. The pharmaceutical compositions are formulated to contain a daily dose, or a convenient fraction of a daily dose, in a dosage unit, which may be a single tablet or a capsule or a convenient volume of a liquid.

All of the usual types of pharmaceutical compositions are used in the present invention, including tablets, lozenges, hard candies, chewable tablets, granules, powders, sprays, capsules, pills, microcapsules, solutions, parenteral solutions, troches, injections (e.g., intravenous, intraperitoneal, intramuscular or subcutaneous), suppositories, elixirs, syrups and suspensions.

For parenteral administration, the compounds, prodrugs, isomers and pharmaceutically acceptable salts of the present invention are used as solutions in sesame or peanut oil, or as aqueous solutions (e.g., aqueous propyleneglycol), as the case may be, and they are best used in the form of a sterile aqueous solution which may contain other substances, such as enough salts or glucose to make the solution isotonic (the pH of the solution being suitably adjusted and buffered, where necessary) and surfactants, for example, hydroxypropylcellulose. Such oily solutions are suitable for intra-articular, intramuscular and subcutaneous injection purposes. Such aqueous solutions are suitable for intravenous injection purposes.

The compounds, prodrugs, isomers and pharmaceutically acceptable salts of the present invention may also be administered topically and this may be done by way of, e.g., creams, jellies, salves, lotions, gels, pastes, ointments, and the like, in accordance with standard pharmaceutical practice. The compounds, prodrugs, isomers and pharmaceutically acceptable salts of this invention of the present invention may also be administered transdermally (e.g., through the use of a patch). Any suitable formulation for transdermal application comprising a compound of the present invention may be employed and such formulations would generally also contain a suitable transdermal carrier, e.g., an absorbable pharmacologically acceptable solvent to promote and assist passage of the compounds through the subject's skin. For example, suitable transdermal devices may comprise the form of a bandage or patch having a backing member and a reservoir containing the subject compound. Such bandage-type transdermal devices may further include suitable carriers, rate-controlling barriers, and means for securing the transdermal device to the subject's skin.

As will be described in detail hereinbelow, the pharmaceutical compositions of the present invention are prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate, or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone, or aluminum stearate), a dispersing agent (e.g., hydroxypropylmethylcellulose), a diluent (e.g., water), a coloring agent, an emulsifying agent, and a base wax (e.g., cocoa butter, white petrolatum or polyethylene glycol).

Any of the compounds, prodrugs, isomers or pharmaceutically acceptable salts of the present invention may be readily formulated as tablets, capsules, and the like. It is preferable to prepare solutions from water-soluble salts of these compounds.

In general, all of the pharmaceutical compositions of the present invention are prepared according to methods usual in pharmaceutical chemistry.

Capsules are prepared by mixing a compound, prodrug, isomer or pharmaceutically acceptable salt of the invention with a suitable diluent and filling the proper amount of the mixture in capsules. The usual diluents include inert powdered substances such as starch of many different kinds, powdered cellulose, especially crystalline and microcrystalline cellulose, sugars, such as fructose, mannitol and sucrose, grain flours and similar edible powders.

Tablets are prepared by direct compression, by wet granulation, or by dry granulation. These formulations usually incorporate diluents, binders, lubricants and disintegrators as well as a compound, prodrug, isomer or pharmaceutically acceptable salt of the present invention. Common diluents include, for example, various types of starch, lactose, mannitol, kaolin, calcium phosphate or sulfate, inorganic salts such as sodium chloride and powdered sugar. Powdered cellulose derivatives may also be used. Common tablet binders include substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is generally necessary in a tablet formulation to prevent the tablet and punches from sticking in the die. The lubricant is chosen from such slippery solids such as talc, magnesium and calcium stearate, stearic acid and hydrogenated vegetable oils.

Tablet disintegrators include substances which swell when wetted to break up the tablet and release a compound, prodrug, isomer or pharmaceutically acceptable salt of the present invention. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds, prodrugs, isomers and pharmaceutically acceptable salts of the present invention may also be formulated as chewable tablets, by using large amounts of pleasant-tasting substances such as mannitol in the formulation, as is now well-established in the art.

Where it is desired to administer a compound, prodrug, isomer or pharmaceutically acceptable salt of the present invention as a suppository, any suitable base can be used. Cocoa butter is a traditional suppository base, which may be modified by the addition of waxes to raise its melting point. Water-miscible suppository bases comprising, particularly, polyethylene glycols of various molecular weights are in wide use.

As discussed above, the effect of a compound, prodrug, isomer or pharmaceutically acceptable salt of the present invention may be delayed or prolonged by proper formulation. For example, a slowly soluble pellet of a compound, prodrug, isomer or pharmaceutically acceptable salt of the present invention may be prepared and incorporated in a tablet or capsule. The technique may be improved by making pellets of several different dissolution rates and filling capsules with a mixture of the pellets. Tablets or capsules may be coated with a film which resists dissolution for a predictable period of time. The parenteral preparations may also be made long-acting by dissolving or suspending a compound, prodrug, isomer or pharmaceutically acceptable salt of the present invention, as the case may be, in oily or emulsified vehicles which allow it to disperse only slowly in the serum.

The compounds, prodrugs, isomers and pharmaceutically acceptable salts of this invention are also administered to a mammal other than a human. The method of administration and the dosage to be administered to such a mammal will depend, for example, on the animal species and the disease or disorder being treated. The compounds, prodrugs, isomers and pharmaceutically acceptable salts of the present invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of the present invention with a suitable diluent such as carbowax or carnuba wax together with a lubricant, liquid drench or paste, e.g., prepared by dispersing a compound, prodrug, isomer or pharmaceutically acceptable salt of the present invention in a pharmaceutically acceptable oil such as peanut oil, sesame oil or corn oil. The compounds, prodrugs, isomers and pharmaceutically acceptable salts of the present invention may also be administered to animals as an implant. Such formulations are prepared in a conventional manner in accordance with standard veterinary practice. As an alternative, the compounds, prodrugs, isomers and pharmaceutically acceptable salts of the present invention may be administered with the water supply, e.g., in the form of a liquid or water-soluble concentrate. In addition, the compounds, prodrugs, isomers and pharmaceutically acceptable salts of this invention may be administered in the animal feedstuff, e.g., a concentrated feed additive or premix may be prepared for mixing with the normal animal feed, commonly along with a suitable carrier therefor. The carrier facilitates uniform distribution of a compound, prodrug, isomer or pharmaceutically acceptable salt of the present invention, e.g., in the finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

The present invention has an aspect that relates to the treatment of the disease/conditions described herein with a combination of active ingredients. In combination therapy treatment, both the compounds of this invention and the other drug therapies are administered to mammals (e.g., humans, male or female) by conventional formulations and methods, as described above. As recognized by those skilled in the art, the therapeutically effective amounts of the compounds of this invention and the other drug therapies to be administered to a patient in combination therapy treatment will depend upon a number of factors, including, without limitation, the biological activity desired, the condition of the patient, and tolerance for the drug.

Since the active ingredients in combination therapy treatment may be administered separately, the present invention also relates to combining separate pharmaceutical compositions in kit form. The kit comprises two separate pharmaceutical compositions: a compound of Formula I, or a prodrug thereof, or a geometric or optical isomer thereof, or a pharmaceutically acceptable salt of such compound, prodrug, or isomer, and a second compound as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), or are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day. Also, a daily dose of a compound of Formula I, or a prodrug thereof, or an isomer thereof, or a pharmaceutically acceptable salt of such compound, prodrug or isomer, can consist of one tablet or capsule, while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Utility of the compounds of Formula I, isomers thereof, prodrugs of said compounds or isomers, or pharmaceutically acceptable salts of said compounds, isomers or prodrugs, are demonstrated by activity in one or more of the assays described below:

Assay 1

Oxygen Consumption

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of the compounds, isomers, prodrugs, and pharmaceutically acceptable salts thereof of the present invention to generate a thermogenic response may be demonstrated according to the following protocol:

A. Experimental Summary

This in vivo screen is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats.

Male fatty Zucker rats having a body weight range of from about 400 g to about 500 g are housed for from about 3 to about 7 days in individual cages under standard laboratory conditions prior to the initiation of the study.

A compound of Formula I, an isomer, prodrug or pharmaceutically acceptable salt thereof, and a vehicle, or $T_3$ sodium salt, is administered by oral gavage as a single daily dose given between about 3 p.m. to about 6 p.m. for about 6 days. A compound of Formula I, an isomer, prodrug or pharmaceutically acceptable salt thereof, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption.

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min.

The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

Assay 2

Binding to Thyroid Hormone Receptors

The ability of a compound of Formula I, isomers thereof, prodrugs of said compounds or isomers, or pharmaceutically acceptable salts of said compounds, isomers or prodrugs, ("the test thyromimetic compound"), to bind to thyroid hormone receptors may be demonstrated in the following protocol:

A. Preparation of Insect Cell Nuclear Extracts

High Five cell pellets (BTI-TN-5B1-4, catalogue number B855-02, Invitrogen®, Carlsbad, Calif.) obtained about 48 h after infection with baculovirus (GibcoBRL®, Gaithersburg, Md.) expressing either human TRα or TRβ (Institute Pasteur de Lille, France) are suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 µg/mL leupeptin). After about 10 min incubation on ice, the suspension is homogenized by 20 strokes with a Dounce homogenizer (VWR® Scientific Products, West Chester, Pa.) and centrifuged at 800×g for about 15 min at 4° C. The pellet (nuclei) is suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension is centrifuged at 100,000×g for about 30 min at 4° C. The supernatant (nuclear extract) is stored in 0.5 mL aliquots at −80° C.

B. Binding Assay

Competition binding assays to measure the interaction of the test thyromimetic compounds with thyroid hormone receptor α1 and β1 (TRα and TRβ) are carried out according to the following protocol:

Solutions of test thyromimetic compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT, "assay buffer") containing 0.4 nM $^{125}$I-T$_3$ (commercially available) (specific activity of about 220 Ci/mmol) to yield solutions that varied in compound concentration from about 10 μM to about 0.1 nM.

High Five insect cell nuclear extract containing either TRα or TRβ is diluted to a total protein concentration of 0.0075 mg/mL using the assay buffer as diluent.

One volume (100 μL) of each thyromimetic compound dilution (containing 0.4 nM $^{125}$I-T3) is combined with an equal volume (100 μL) of diluted nuclear extract containing TRα1 or TRβ1, and incubated at RT for about 90 min. A 150 μL sample of the binding reaction is removed and placed into a 96-well filter plate (Millipore®, Bedford, Mass.) that has been pre-washed with ice-cold assay buffer. The plate is subjected to vacuum filtration using a filtration manifold (Millipore®). Each well is washed five times by the addition of 200 μL of ice-cold assay buffer and subsequent vacuum filtration. The plate is removed from the vacuum filtration manifold, the bottom of the plate is briefly dried on paper towels, then 25 μL of Wallac® (EG&G Wallac®, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter.

The following compounds of the present invention are preferred:

8-[[5-[2,6-dichloro-4-(4,5-dihydro-3,5-dioxo-1,2,4-triazine-2(3H)-yl)phenoxy]-2-hydroxyphenyl]sulfonyl]-spiro[8-azabicyclo[3.2.1]octane-3,2'-(3'H)-dihydro-furan];

2-{3,5-dichloro-4-[3-(3,3-dimethyl-piperidine-1-sulfonyl)-4-hydroxy-phenoxy]-phenyl}-2H-[1,2,4]triazine-3,5-dione;

2-{3,5-dichloro-4-[4-hydroxy-3-(3-methyl-3-phenyl-piperidine-1-sulfonyl)-phenoxy]-phenyl}-2H-[1,2,4]triazine-3,5-dione;

N-cyclohexyl-5-[2,6-dichloro-4-(3,5-dioxo-4,5-dihydro-3H-[1,2,4]triazin-2-yl)-phenoxy]-2-hydroxy-benzenesulfonamide;

N-bicyclo[2.2.1]hept-2-yl-5-[2,6-dichloro-4-(3,5-dioxo-4,5-dihydro-3H-[1,2,4]triazin-2-yl)-phenoxy]-2-hydroxy-benzamide;

2-{3,5-dichloro-4-[3-(3,3-dimethyl-piperidine-1-carbonyl)-4-hydroxy-phenoxy]-phenyl}-2H-[1,2,4]triazine-3,5-dione;

N-bicyclo[2.2.1]hept-2-yl-5-[2,6-dichloro-4-(3,5-dioxo-4,5-dihydro-3H-[1,2,4]triazin-2-yl)-phenoxy]-2-hydroxy-benzamide;

2-{3,5-dichloro-4-[4-hydroxy-3-(3-methyl-3-phenyl-piperidine-1-carbonyl)-phenoxy]-phenyl}-2H-[1,2,4]triazine-3,5-dione;

5-[2,6-dichloro-4-(3,5-dioxo-4,5-dihydro-3H-[1,2,4]triazin-2-yl)-phenoxy]-N-(6,6-dimethyl-bicyclo[3.1.1]hept-2-yl)-2-hydroxy-benzamide;

2-{3,5-dichloro-4-[3-(3,5-dimethyl-piperidine-1-carbonyl)-4-hydroxy-phenoxy]-phenyl}-2H-[1,2,4]triazine-3,5-dione; and 2-{3,5-dichloro-4-[4-hydroxy-3-(piperidine-1-carbonyl)-phenoxy]-phenyl}-2H-[1,2,4]triazine-3,5-dione.

The following compounds of the present invention are also preferred:

2-[3-Chloro-4-(3-cyclobutylmethanesulfonyl-4-hydroxy-phenoxy)-5-methyl-phenyl]-2H-[1,2,4]triazine-3,5-dione;

2-[3,5-Dichloro-4-(3-cyclobutylmethanesulfonyl-4-hydroxy-phenoxy)-phenyl]-2H-[1,2,4]triazine-3,5-dione;

2-[3,5-Dimethyl-4-(3-cyclobutylmethanesulfonyl-4-hydroxy-phenoxy)-phenyl]-2H-[1,2,4]triazine-3,5-dione;

2-[3-Chloro-4-(3-cyclopentylmethanesulfonyl-4-hydroxy-phenoxy)-5-methyl-phenyl]-2H-[1,2,4]triazine-3,5-dione;

2-[3,5-Dichloro-4-(3-cyclopentylmethanesulfonyl-4-hydroxy-phenoxy)-phenyl]-2H-[1,2,4]triazine-3,5-dione;

2-[3,5-Dimethyl-4-(3-cyclopentylmethanesulfonyl-4-hydroxy-phenoxy)-phenyl]-2H-[1,2,4]triazine-3,5-dione;

2-[3-Chloro-4-(3-cyclohexylmethanesulfonyl-4-hydroxy-phenoxy)-5-methyl-phenyl]-2H-[1,2,4]triazine-3,5-dione;

2-[3,5-Dichloro-4-(3-cyclohexylmethanesulfonyl-4-hydroxy-phenoxy)-phenyl]-2H-[1,2,4]triazine-3,5-dione; and 2-[3,5-Dimethyl-4-(3-cyclohexylmethanesulfonyl-4-hydroxy-phenoxy)-phenyl]-2H-[1,2,4]triazine-3,5-dione.

The following Preparations and Examples are provided solely for the purpose of illustration and do not limit the invention which is defined by the claims.

Preparation 1

4-(3-Bromo-4-methoxyphenoxy)-3,5-dimethylnitrobenzene

To a solution of 3,5-dimethyl-4-(4'-methoxyphenoxy) nitrobenzene (4.0 g) (J. Med. Chem. 1995, 38, 703) in chloroform (150 ml) were added N-bromosuccinimide (2.6 g) and trifluoroacetic acid (1.1 ml), and the resulting mixture was heated under reflux for 90 min. Additional portions of N-bromosuccinimide (2.6 g) and trifluoroacetic acid (1.1 ml) were added, followed by further heating for 18 h. The reaction was washed with sodium bicarbonate, dried (Na$_2$SO$_4$) and concentrated to afford the title compound as an orange solid (5.0 g). MS Calc: 351; Found: 352 (M+1).

Preparation 2

4-(3-Bromo-4-methoxy-phenoxy)-3,5-dimethyl-phenylamine

A mixture of the compound (5.0 g) of PREPARATION 1 and 10% palladium on carbon (0.6 g) in ethyl acetate (100 ml) was hydrogenated at 50 psi (about 3.4 atm) for 3 h. The reaction was filtered through Celite® and concentrated to afford the title compound as a yellow solid (4.3 g). MS Calc: 321; Found 322 (M+1).

Preparation 3

({[4-(3-Bromo-4-methoxy-phenoxy)-3,5-dimethyl-phenyl]-hydrazono}-cyano-acetyl)-carbamic acid ethyl ester To a suspension of 4-(3-bromo-4-methoxy-phenoxy)-3,5-dimethyl-phenylamine (2.0 g) of PREPARATION 2 in 6N hydrochloric acid (45 ml) at 0° C. was added dropwise a solution of sodium nitrite (560 mg) in water (1.25 ml). After stirring 30 min at 0° C., this solution was added in portions to a mixture of ethylcyanoacetylurethane (2.4 g) and pyridine (12 ml) in water (150 ml) at room temperature. The resulting solids were collected, washed with water, and dried to afford the title compound as an orange solid (1.5 g) which was used directly.

EXAMPLE 1

2-[4-(3-Bromo-4-methoxy-phenoxy)-3,5-dimethyl-phenyl]-3,5-dioxo-2,3,4,5-tetrahydro-[1,2,4]triazine-6-carbonitrile A solution of ({[4-(3-bromo-4-methoxy-phenoxy)-3,5-dimethyl-phenyl]-hydrazono}-cyano-acetyl)-carbamic acid ethyl ester (1.0 g) of PREPARATION 3, potassium acetate (200 mg) and acetic acid (11 ml) were heated to 120° C. for 5 h. The reaction was concentrated, water was added, and the resulting solids were collected and dried to afford the title compound as a yellow solid (895 mg). Calc.: 442.0; Found: 441.0 (M−1).

EXAMPLE 2

2-[4-(3-Bromo-4-methoxy-phenoxy)-3,5-dimethyl-phenyl]-3,5-dioxo-2,3,4,5-tetrahydro-[1,2,4]triazine-6-carboxylic acid A solution of 2-[4-(3-bromo-4-methoxy-phenoxy)-3,5-dimethyl-phenyl]-3,5-dioxo-2,3,4,5-tetrahydro-[1,2,4]triazine-6-carbonitrile (700 mg) of EXAMPLE 1, hydrochloric acid (5 ml) and acetic acid (5 ml) was heated to 120° C. for 3 h. The resulting solids were filtered, rinsed and dried to afford the title compound as a brown solid (593 mg). MS Calc.: 461.0; Found: 459.7 (M−1).

EXAMPLE 3

2-[4-(3-Bromo-4-methoxy-phenoxy)-3,5-dimethyl-phenyl]-2H-[1,2,4]triazine-3,5-dione A mixture of 2-[4-(3-bromo-4-methoxy-phenoxy)-3,5-dimethyl-phenyl]-3,5-dioxo-2,3,4,5-tetrahydro-[1,2,4]triazine-6-carboxylic acid (0.3 g) of EXAMPLE 2 and thioacetic acid (0.6 ml) was heated at 170° C. for 4 h. The mixture was diluted with ethyl acetate, washed with saturated sodium bicarbonate, and dried with sodium sulfate to afford a crude brown oil (0.6 g). Chromatography on silica gel, eluting with ethyl acetate and hexanes, gave the title compound (160 mg) as a yellow foam.

MS Calc.: 417.0; Found: 416.1 (M−1).

EXAMPLE 4

2-[4-(3-Bromo-4-hydroxy-phenoxy)-3,5-dimethyl-phenyl]-2H-[1,2,4]triazine-3,5-dione Prepared from 2-[4-(3-bromo-4-methoxy-phenoxy)-3,5-dimethyl-phenyl]-2H-[1,2,4]triazine-3,5-dione (25 mg) of EXAMPLE 3 in an analogous manner to that described in EXAMPLE 9 below to give the title product (12 mg). MS Calc.: 403.0; Found: 401.9 (M−1).

EXAMPLE 5

2-[4-(3-Bromo-4-hydroxy-phenoxy)-3,5-dimethyl-phenyl]-3,5-dioxo-2,3,4,5-tetrahydro-[1,2,4]triazine-6-carboxylic acid To a solution (40 ml) of 2-[4-(3-bromo-4-methoxy-phenoxy)-3,5-dimethyl-phenyl]-3,5-dioxo-2,3,4,5-tetrahydro-[1,2,4]triazine-6-carboxylic acid (800 mg) in methylene chloride (40 ml) was added boron tribromide (5.2 ml of a 1.0 M solution). After stirring for 18 h, the reaction mixture was poured over ice and stirred at room temperature for 3 h. The reaction was extracted three times with 1N potassium hydroxide, and the aqueous layers were combined, acidified to pH 2 with hydrochloric acid, and extracted three times with ethyl acetate. The organic phases were combined, washed with brine, dried and concentrated to give fluffy yellow solid (408 mg) of the title compound. MS Calc.447; Found: 446 (M−1).

EXAMPLE 6

2-[4-(3-Bromo-4-methoxy-phenoxy)-3,5-dimethyl-phenyl]-4-(2-trimethylsilanyl-ethoxymethyl)-2H-[1,2,4]triazine-3,5-dione Prepared from 2-[4-(3-bromo-4-methoxy-phenoxy)-3,5-dimethyl-phenyl]-2H-[1,2,4]triazine-3,5-dione (40 mg) of EXAMPLE 3 in a manner analogous to that described in EXAMPLE 10, Step A below to give the title product (36 mg). MS Calc.:547; Found: 546 (M−1).

EXAMPLE 7

2-[4-(6-Methoxy-biphenyl-3-yloxy)-3,5-dimethyl-phenyl]-4-(2-trimethylsilanyl-ethoxymethyl)-2H-[1,2,4]triazine-3,5-dione To a solution of 2-[4-(3-bromo-4-methoxy-phenoxy)-3,5-dimethyl-phenyl]-4-(2-trimethylsilanyl-ethoxymethyl)-2H-[1,2,4]triazine-3,5-dione (36 mg) of EXAMPLE 6 in degassed DMF (1.1 ml) were added sequentially tetrakis(triphenylphosphine)-palladium(0) (7.5 mg), phenylboronic acid (24 mg) and 2M aqueous sodium carbonate (0.13 ml). The resulting mixture was heated at 80° C. under nitrogen for 45 h, then additional portions of tetrakis(triphenylphosphine)palladium(0) (7.5 mg), phenylboronic acid (24 mg) and 2M aqueous sodium carbonate (0.13 ml) were added followed by further heating for 18 h. The reaction was diluted with water (4 ml) and extracted with ethyl acetate, then chloroform. The organic layers were washed with brine, dried and concentrated to afford the crude product (43 mg). Purification using silica gel chromatography gave the title compound (30 mg). MS Calc. 546:; Found 545 (M−1).

EXAMPLE 8

2-[4-(6-Hydroxy-biphenyl-3-yloxy)-3,5-dimethyl-phenyl]-2H-[1,2,4]triazine-3,5-dione Prepared from 2-[4-(6-methoxy-biphenyl-3-yloxy)-3,5-dimethyl-phenyl]-4-(2-trimethylsilanyl-ethoxymethyl)-2H-[1,2,4]triazine-3,5-dione (30 mg) of EXAMPLE 7 in a manner analogous to that described in EXAMPLE 10, Step D below to give the title product (3.4 mg). MS Calc.: 401; Found 402 (M+1).

EXAMPLE 9

N-{5-[2,6-Dichloro-4-(3,5-dioxo-4,5-dihydro-3H-[1,2,4]triazin-2-yl)-phenoxy]-2-hydroxy-phenyl}-acetamide.

Step A

2-[3,5-Dichloro-4-(4-methoxy-3-nitro-phenoxy)-phenyl]-2H-[1,2,4]triazine-3,5-dione To a cooled (0° C.), stirred solution of nitric acid (20 mL) in acetic acid (65 mL) was added 2-[3,5-dichloro-4-(4- methoxy-phenoxy)-phenyl]-2H-[1,2,4]triazine-3,5-dione (5.0 g) and the resulting mixture was allowed to stir at ambient temperature for 1.5 h. The resulting solution was poured into 400 mL of water, the resulting solids filtered and dried to afford the title compound of Step A as a yellow solid, 5.1 g. MS Calc.:425.2; Found: 422.9.

Step B

2-[3,5-Dichloro-4-(4-methoxy-3-nitro-phenoxy)-phenyl]-2H-4-[(2-(trimethylsilyl)ethoxymethyl]-[1,2,4]triazine-3,5-dione To a cooled (0° C.) solution of 2-[3,5-dichloro-4-(4-methoxy-3-nitro-phenoxy)-phenyl]-2H-[1,2,4]triazine-3,5-dione (5.2 g) in DMF (50 mL) was added sodium hydride (580 mg, 60% in oil) and the resulting mixture was allowed to stir at ambient temperature for 30 min. 2-(Trimethylsilyl)ethoxymethyl chloride (2.6 mL) was added dropwise and the resulting solution was allowed to stir at room temperature for 3 h. The reaction was quenched into 1:1 water:sat. ammonium chloride and extracted (2×) with ethyl acetate. The combined organic layers were washed with brine, dried ($Na_2SO_4$), concentrated and purified by flash chromatography on silica gel (20% acetone/hexanes) to afford the title compound of Step B as a yellow solid, 5.3 g.

Step C

2-[3,5-Dichloro-4-(3-amino-4-methoxy-phenoxy)-phenyl]-2H-4-[(2-(trimethylsilyl)ethoxymethyl]-[1,2,4]triazine-3,5-dione A solution of 2-[3,5-dichloro-4-(4-methoxy-3-nitro-phenoxy)-phenyl]-2H-4-[(2-(trimethylsilyl)ethoxymethyl]-[1,2,4]triazine-3,5-dione (5.3 g) in ethyl acetate (100 mL) was hydrogenated (50 psi $H_2$, which is about 3.4 atm) over 10% palladium-on-carbon (1.6 g) for 6 h. Filtration through Celite® and concentration in vacuo afforded the title compound of Step C as a yellow foam, 4.9 g.

Step D

N-{5-[2,6-Dichloro-4-(3,5-dioxo-4,5-dihydro-4-[(2-(trimethylsilyl)ethoxymethyl]-3H-[1,2,4]triazin-2-yl)-phenoxy]-2-methoxy-phenyl}-acetamide To a solution of 2-[3,5-dichloro-4-(3-amino-4-methoxy-phenoxy)-phenyl]-2H-4-[(2-(trimethylsilyl)ethoxymethyl]-[1,2,4]triazine-3,5-dione (200 mg) in dichloromethane (0.4 mL) was added triethylamine (80 µL) and acetyl chloride (30 µL). After 20 h, the reaction was poured into water, extracted with ethyl acetate, the organic phase washed with brine, dried ($Na_2SO_4$), concentrated in vacuo and flash chromatographed on silica gel (30% acetone/hexanes) to afford the title compound of Step D as an off-white foam, 218 mg.

Step E

N-{5-[2,6-Dichloro-4-(3,5-dioxo-4,5-dihydro-3H-[1,2,4]triazin-2-yl)-phenoxy]-2-hydroxy-phenyl}-acetamide To a cooled (0° C.), stirred solution of N-{5-[2,6-dichloro-4-(3,5-dioxo-4,5-dihydro-4-[(2-(trimethylsilyl)ethoxymethyl]-3H-[1,2,4]triazin-2-yl)-phenoxy]-2-methoxy-phenyl}-acetamide (215 mg) in dichloromethane (4 mL) was added boron tribromide (18 µL) and the resulting solution was allowed to stir at ambient temperature for 20 h.

The reaction mixture was poured over ice, stirred for 0.5 h and extracted with ethyl acetate. The organic phase was dried ($Na_2SO_4$), concentrated in vacuo and flash chromatographed on silica gel (30–50% acetone/hexanes) to afford the title compound of this EXAMPLE as a colorless foam, 101 mg. m.p.=101–109° C. MS Calc.:423.2; Found:423.0.

Using the appropriate starting materials, EXAMPLES 9–1 to 9–11 were prepared in an analogous manner to that described in EXAMPLE 9.

EXAMPLE 9-1

N-{5-[2,6-Dichloro-4-(3,5-dioxo-4,5-dihydro-3H-[1,2,4]triazin-2-yl)-phenoxy]-2-hydroxy-phenyl}-benzamide MS Calc.:485.3; Found:485.0.

EXAMPLE 9-2

N-{5-[2,6-Dichloro-4-(3,5-dioxo-4,5-dihydro-3H-[1,2,4]triazin-2-yl)-phenoxy]-2-hydroxy-phenyl}-isobutyramide MS Calc.:451.3; Found:451.0.

EXAMPLE 9-3

Cyclohexanecarboxylic acid {5-[2,6-dichloro-4-(3,5-dioxo-4,5-dihydro-3H-[1,2,4]triazin-2-yl)-phenoxy]-2-hydroxy-phenyl}-amide MS Calc.:491.3; Found:491.0.

EXAMPLE 9-4

N-{5-[2,6-Dichloro-4-(3,5-dioxo-4,5-dihydro-3H-[1,2,4]triazin-2-yl)-phenoxy]-2-hydroxy-phenyl}-nicotinamide MS Calc.:486.3; Found:486.0.

EXAMPLE 9-5

5-Methyl-isoxazole-3-carboxylic acid {5-[4-(3,5-dioxo-4,5-dihydro-3H-[1,2,4]triazin-2-yl)-2,6-dimethyl-phenoxy]-2-hydroxy-phenyl}-methyl-amide MS Calc.: 463.5; Found: 462.2 (M−1).

EXAMPLE 9-6

5-Methyl-isoxazole-3-carboxylic acid {5-[4-(3,5-dioxo-4,5-dihydro-3H-[1,2,4]triazin-2-yl)-2,6-dimethyl-phenoxy]-2-hydroxy-phenyl}-amide MS Calc.: 449.4; Found: 448.2 (M−1).

EXAMPLE 9-7

N-{5-[4-(3,5-Dioxo-4,5-dihydro-3H-[1,2,4]triazin-2-yl)-2,6-dimethyl-phenoxy]-2-hydroxy-phenyl}-4-trifluoromethoxy-benzamide MS Calc.: 528.5; Found:527.1 (M−1).

EXAMPLE 9-8

N-{5-[2,6-Dichloro-4-(3,5-dioxo-4,5-dihydro-3H-[1,2,4]triazin-2-yl)-phenoxy]-2-hydroxy-phenyl}-4-trifluoromethoxy-benzamide MS Calc.: 569.3; Found: 567.1(M−1).

EXAMPLE 9-9

N-{5-[2,6-Dichloro-4-(3,5-dioxo-4,5-dihydro-3H-[1,2,4]triazin-2-yl)-phenoxy]-2-hydroxy-phenyl}-4-fluoro-benzamide MS Calc.: 503.3; Found:501.1 (M−1).

EXAMPLE 9-10

N-{5-[2,6-Dichloro-4-(3,5-dioxo-4,5-dihydro-3H-[1,2,4]triazin-2-yl)-phenoxy]-2-hydroxy-phenyl}-4-trifluoromethyl-benzamide MS Calc.: 553.3; Found: 551.1 (M−1).

EXAMPLE 9-11

5-Methyl-isoxazole-3-carboxylic acid {5-[2,6-dichloro-4-(3,5-dioxo-4,5-dihydro-3H-[1,2,4]triazin-2-yl)-phenoxy]-2-hydroxy-phenyl}-amide MS Calc.:490.3; Found: 488.2 (M−1).

EXAMPLE 10

1-{5-[2,6-Dichloro-4-(3,5-dioxo-4,5-dihydro-3H-[1,2,4]triazin-2-yl)-phenoxy]-2-hydroxy-phenyl}-3-(4-trifluoromethoxy-phenyl)-urea

Step A

2-[3,5-Dichloro-4-(4-methoxy-3-nitro-phenoxy)-phenyl]-4-(2-trimethylsilanylethoxymethyl)-2H-[1,2,4]triazine-3,5-dione To a solution of 2-[3,5-dichloro-4-(4-methoxy-3-nitro-phenoxy)-phenyl]-2H-[1,2,4]-triazin-3,5-dione (1.32 g, 3.1 mmol) in 12 mL of DMF at 0° C. was added sodium hydride (60% dispersion in mineral oil, 0.15 g, 3.7 mmol). After stirring at 0° C. for 5 min, the mixture was stirred at room temperature for 30 min as a clear reddish brown solution. To the solution at room temperature was added SEMCI (0.63 g, 3.74 mmol). After stirring at room temperature for 20 h, the solution was diluted with $H_2O$ (30 mL) and extracted with EtOAc (2×50 mL). The combined EtOAc extracts were washed with 1N HCl (100 mL), $H_2O$ (3×50 mL), brine (100 mL), dried and concentrated. The residue was dissolved in $CH_2Cl_2$ followed by addition of ether to give the title compound (0.83 g) of Step A as light brown crystals. NMR (400 Mhz, $CD_3OD$) d 0.02 (m, 9H), 1.01 (m, 2H), 3.75 (m, 2H), 5.45 (s, 2H).

Step B

2-[3,5-Dichloro-4-(4-methoxy-3-amino-phenoxy)-phenyl]-4-(2-trimethylsilanyl-ethoxymethyl)-2H-[1,2,4]triazine-3,5-dione To a solution of 2-[3,5-dichloro-4-(4-methoxy-3-nitro-phenoxy)-phenyl]-4-(2-trimethyl-silanyl-ethoxymethyl)-2H-[1,2,4]triazine-3,5-dione (0.83 g, 1.6 mmol) in a mixture of EtOH/EtOAc (75 mL/50 mL) was added 10% Pd/C (0.25 g). The mixture was hydrogenated at room temperature under 40 psi (about 2.7 atm) hydrogen pressure for 20 h and filtered through Celite®. The filtrate was concentrated to give the title compound (0.73 g) of Step B as a brown solid which was used in the next step without purification. MS Calc.: 525.5; Found: 524.1 (M−1).

Step C

1-{5-[2,6-Dichloro-4-(3,5-dioxo-4-(2-trimethylsilanyl-ethoxy-methyl) 4,5-dihydro-3H-[1,2,4]triazin-2-yl)-phenoxy]-2-methoxy-phenyl}-3-(4-trifluoro-methoxy-phenyl)-urea To a solution of 2-[3,5-dichloro-4-(4-methoxy-3-amino-phenoxy)-phenyl]-4-(2-trimethyl-silanyl-ethoxymethyl)-2H-[1,2,4]triazine-3,5-dione (100 mg, 0.19 mmol) in 3 mL of $CH_2Cl_2$ was added diisopropylethylamine (29.5 mg, 0.23 mmol) and 4-trifluoro-methoxyphenyl isocyanate (60 mg, 0.29 mmol). The resulting mixture was stirred at room temperature for 20 h, quenched with $H_2O$ (5 mL), and extracted with $CH_2Cl_2$ (3×10 mL). The combined extracts were washed with sat'd $NaHCO_3$, 1N HCl, water, dried and concentrated. The residue was purified by preparative TLC (40% EtOAC in hexanes) to give the title compound (75.9 mg) of Step C as a off-white solid. MS Calc.: 728.6; Found: 729.7 (M+1).

Step D

1-{5-[2,6-Dichloro-4-(3,5-dioxo-4,5-dihydro-3H-[1,2,4]triazin-2-yl)-phenoxy]-2-hydroxy-phenyl}-3-(4-trifluoromethoxy-phenyl)-urea To a solution of 1-{5-[2,6-dichloro-4-(3,5-dioxo-4-(2-trimethylsilanyl-ethoxy-methyl)4,5-dihydro-3H-[1,2,4]triazin-2-yl)-phenoxy]-2-methoxy-phenyl}-3-(4-trifluoromethoxy-phenyl)-urea (72 mg, 0.1 mmol) in $CH_2Cl_2$ was added dropwise $BBr_3$ (1M in $CH_2Cl_2$, 4.0 mL, 0.4 mmol). The mixture was stirred at room temperature for 18 h and quenched with water (10 mL). After stirring at room temperature for 1 h, the quenched mixture was extracted with $CH_2Cl_2$ (3×10 mL). The combined $CH_2Cl_2$ extracts were dried and concentrated. The residue was purified by preparative TLC (10% MeOH in $CH_2Cl_2$) to afford the title compound (25.4 mg) of this EXAMPLE. MS Calc.:584.3 Found:581.8 (M−1).

Using the appropriate starting materials, EXAMPLES 10-1 to 10-4 were prepared in an analogous manner to that described in EXAMPLE 10.

EXAMPLE 10-1

1-(2,4-Difluoro-phenyl)-3-{5-[4-(3,5-dioxo-4,5-dihydro-3H-[1,2,4]triazin-2-yl)-2,6-dimethyl-phenoxy]-2-hydroxy-phenyl}-urea MS Calc.:495.5; Found:494.2 (M−1).

EXAMPLE 10-2

1-(3,4-Dichloro-phenyl)-3-{5-[4-(3,5-dioxo-4,5-dihydro-3H-[1,2,4]triazin-2-yl)-2,6-dimethyl-phenoxy]-2-hydroxy-phenyl}-urea MS Calc.:528.4; Found:528.1 (M−1).

EXAMPLE 10-3

1-{5-[4-(3,5-Dioxo-4,5-dihydro-3H-[1,2,4]triazin-2-yl)-2,6-dimethyl-phenoxy]-2-hydroxy-phenyl}-3-(4-trifluoromethoxy-phenyl)-urea MS Calc.:543.1; Found:542.2 (M−1).

EXAMPLE 10-4

1-{5-[2,6-Dichloro-4-(3,5-dioxo-4,5-dihydro-3H-[1,2,4]triazin-2-yl)-phenoxy]-2-hydroxy-phenyl}-3-(3,4-dichloro-phenyl)-urea MS Calc.:569.1; Found:567.8 (M−1).

EXAMPLE 11

2-[4-(4-Hydroxy-3-isopropyl-phenoxy)-3,5-dimethyl-phenyl]-2H-[1,2,4]-triazine-3,5-dione According to the procedure described for 2-[3,5-dichloro-4-(4-hydroxy-phenoxy)-phenyl]-2H-[1,2,4]triazine-3,5- dione, the title compound of this EXAMPLE was prepared. MS Calc.: 367.4; Found: 366.0 (M−1).

EXAMPLE 12

N-{5-[2,6-Dichloro-4-(3,5-dioxo-4,5-dihydro-3H-[1,2,4]triazin-2-yl)-phenoxy]-2-hydroxy-phenyl}-4-fluoro-benzenesulfonamide

Step A

2-[3,5-Dichloro-4-(3-amino-4-methoxy-phenoxy)-phenyl]-2H-[1,2,4]triazine-3,5-dione A solution of 2-[3,5-dichloro-4-(4-methoxy-3-nitro-phenoxy)-phenyl]-2H-[1,2,4]triazine-3,5-dione (1.1 g) in ethanol (40 mL) and ethyl acetate (4 mL) was hydrogenated (45 psi which is about 3.1 atm) over 10% palladium-on-carbon (300 mg) for 4 h. The reaction was filtered and concentrated in vacuo to afford the title compound of Step A as a dark foam, 1.0 g.

Step B

N-{5-[2,6-Dichloro-4-(3,5-dioxo-4,5-dihydro-3H-[1,2,4]triazin-2-yl)-phenoxy]-2-methoxy-phenyl}-4-fluoro-benzenesulfonamide To a stirred solution of 2-[3,5-dichloro-4-(3-amino-4-methoxy-phenoxy)-phenyl]-2H-[1,2,4]triazine-3,5-dione (100 mg) in pyridine (1 mL) was added 4-fluorobenzenesulfonyl chloride (59 mg) and the resulting solution was allowed to stir at room temperature for 1 h. The reaction solution was poured over water, extracted with ethyl acetate, the organic layer washed with 1N hydrochloric acid, water, brine, dried ($Na_2SO_4$), concentrated in vacuo and flash chromatographed on silica gel (40% acetone/hexanes) to afford the title compound of Step B as a light-yellow colored solid, 115 mg. m.p. 90–96° C., MS Calc.:553.4; Found:550.9.

Step C

N-{5-[2,6-Dichloro-4-(3,5-dioxo-4,5-dihydro-3H-[1,2,4]triazin-2-yl)-phenoxy]-2-hydroxy-phenyl}-4-fluoro-benzenesulfonamide To a cooled (0° C.), stirred solution of N-{5-[2,6-dichloro-4-(3,5-dioxo-4,5-dihydro-3H-[1,2,4]triazin-2-yl)-phenoxy]-2-methoxy-phenyl}-4-fluoro-benzenesulfonamide (96 mg) in dichloromethane (5 mL) was added boron tribromide (64 µL) and the resulting solution was allowed to stir at ambient temperature for 4 h. The reaction mixture was poured over ice, stirred for 0.5 h and extracted with ethyl acetate. The organic phase was dried ($Na_2SO_4$), concentrated in vacuo and flash chromatographed on silica gel (40% acetone/hexanes) to afford the title compound of this EXAMPLE as a colorless foam, 68 mg. m.p. 222–225° C. (dec), MS Calc.:539.2 Found:536.8.

Using the appropriate starting materials, EXAMPLES 12-1 to 12-30 were prepared in an analogous manner to that described in EXAMPLE 12.

EXAMPLE 12-1

N-{5-[2,6-Dichloro-4-(3,5-dioxo-4,5-dihydro-3H-[1,2,4]triazin-2-yl)-phenoxy]-2-methoxy-phenyl}-C-phenyl-methanesulfonamide MS Calc.:549.4; Found:546.9.

EXAMPLE 12-2

N-{5-[2,6-Dichloro-4-(3,5-dioxo-4,5-dihydro-3H-[1,2,4]triazin-2-yl)-phenoxy]-2-hydroxy-phenyl}-C-phenyl-methanesulfonamide MS Calc.:535.4; Found:533.0.

EXAMPLE 12-3

N-(4-{5-[2,6-Dichloro-4-(3,5-dioxo-4,5-dihydro-3H-[1,2,4]triazin-2-yl)-phenoxy]-2-hydroxy-phenylsulfamoyl}-phenyl)-acetamide MS Calc.:578.4; Found:575.9.

EXAMPLE 12-4

Benzo[1,2,5]oxadiazole-4-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:563.4; Found:560.9.

EXAMPLE 12-5

1-Methyl-1H-imidazole-4-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:525.3; Found:522.9.

EXAMPLE 12-6

5-Chloro-1,3-dimethyl-1H-pyrazole-4-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:573.8; Found:570.9.

EXAMPLE 12-7

3,5-Dimethyl-isoxazole-4-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:540.3; Found:538.0.

EXAMPLE 12-8

2,4-Dimethyl-thiazole-5-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.556.4; Found:553.9.

EXAMPLE 12-9

5-Isoxazol-3-yl-thiophene-2-sulfonic acid {5-[2,6-dichloro-4-(3,5-dioxo-4,5-dihydro-3H-[1,2,4]triazin-2-yl)-phenoxy]-2-methoxy-phenyl}-amide MS Calc.; 608.4 Found:605.9.

EXAMPLE 12-10

5-(1-Methyl-5-trifluoromethyl-1H-pyrazol-3-yl)-thiophene-2-sulfonic acid {5-[2,6-dichloro-4-(3,5-dioxo-4,5-dihydro-3H-[1,2,4]triazin-2-yl)-phenoxy]-2-methoxy-phenyl}-amide MS Calc.:689.4; Found:687.0.

EXAMPLE 12-11

5-Benzenesulfonyl-thiophene-2-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:667.5; Found:664.9.

EXAMPLE 12-12

5-(1-Methyl-5-trifluoromethyl-1H-pyrazol-3-yl)-thiophene-2-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:675.4; Found:672.9.

EXAMPLE 12-13

5-Isoxazol-3-yl-thiophene-2-sulfonic acid {5-[2,6-dichloro-4-(3,5-dioxo-4,5-dihydro-3H-[1,2,4]triazin-2-yl)-phenoxy]-2-hydroxy-phenyl}-amide MS Calc.:594.4; Found:591.9.

EXAMPLE 12-14

N-{5-[2-Chloro-4-(3,5-dioxo-4,5-dihydro-3H-[1,2,4]triazin-2-yl)-6-methyl-phenoxy]-2-hydroxy-phenyl}-benzenesulfonamide MS Calc.:500.9; Found:499.1 (M−1).

EXAMPLE 12-15

N-{5-[2-Chloro-4-(3,5-dioxo-4,5-dihydro-3H-[1,2,4]triazin-2-yl)-6-methyl-phenoxy]-2-hydroxy-phenyl}-4-fluoro-benzenesulfonamide MS Calc.:518.9; Found:517.1.

EXAMPLE 12-16

4-Chloro-N-{5-[2-chloro-4-(3,5-dioxo-4,5-dihydro-3H-[1,2,4]triazin-2-yl)-6-methyl-phenoxy]-2-hydroxy-phenyl}-benzenesulfonamide MS Calc.:535.4; Found:533.0.

EXAMPLE 12-17

N-{5-[2-Chloro-4-(3,5-dioxo-4,5-dihydro-3H-[1,2,4]triazin-2-yl)-6-methyl-phenoxy]-2-hydroxy-phenyl}-3-trifluoromethyl-benzenesulfonamide MS Calc.:568.9; Found:567.0.

EXAMPLE 12-18

N-{5-[2-Chloro-4-(3,5-dioxo-4,5-dihydro-3H-[1,2,4]triazin-2-yl)-6-methyl-phenoxy]-2-hydroxy-phenyl}-4-cyano-benzenesulfonamide MS Calc.:525.9; Found:524.1.

EXAMPLE 12-19

N-{5-[2-Chloro-4-(3,5-dioxo-4,5-dihydro-3H-[1,2,4]triazin-2-yl)-6-methyl-phenoxy]-2-hydroxy-phenyl}-C-phenyl-methanesulfonamide MS Calc.:515.0; Found:513.1.

EXAMPLE 12-20

2-Chloro-N-{5-[2-chloro-4-(3,5-dioxo-4,5-dihydro-3H-[1,2,4]triazin-2-yl)-6-methyl-phenoxy]-2-hydroxy-phenyl}-benzenesulfonamide MS Calc.:535.4; Found:533.0.

EXAMPLE 12-21

N-{5-[2-Chloro-4-(3,5-dioxo-4,5-dihydro-3H-[1,2,4]triazin-2-yl)-6-methyl-phenoxy]-2-hydroxy-phenyl}-4-trifluoromethyl-benzenesulfonamide MS Calc.:568.9; Found:567.1.

EXAMPLE 12-22

N-{5-[2,6-Dibromo-4-(3,5-dioxo-4,5-dihydro-3H-[1,2,4]triazin-2-yl)-phenoxy]-2-hydroxy-phenyl}-4-fluoro-benzenesulfonamide MS Calc.:628.2; Found:626.9 (M−1).

EXAMPLE 12-23

N-{5-[2,6-Dibromo-4-(3,5-dioxo-4,5-dihydro-3H-[1,2,4]triazin-2-yl)-phenoxy]-2-hydroxy-phenyl}-benzenesulfonamide MS Calc.:610.2; Found:608.8.

EXAMPLE 12-24

N-{5-[2,6-Dibromo-4-(3,5-dioxo-4,5-dihydro-3H-[1,2,4]triazin-2-yl)-phenoxy]-2-hydroxy-phenyl}-phenylmethanesulfonamide MS Calc.:624.3; Found:622.9 (M−1).

EXAMPLE 12-25

N-{5-[2-Chloro-4-(3,5-dioxo-4,5-dihydro-3H-[1,2,4]triazin-2-yl)-6-methyl-phenoxy]-2-hydroxy-phenyl}-C-(4-fluoro-phenyl)-methanesulfonamide MS Calc.:532.9; Found:531.1.

EXAMPLE 12-26

N-{5-[2-Chloro-4-(3,5-dioxo-4,5-dihydro-3H-[1,2,4]triazin-2-yl)-6-methyl-phenoxy]-2-hydroxy-phenyl}-C-p-tolyl-methanesulfonamide MS Calc.:529.0; Found:527.1.

EXAMPLE 12-27

N-{5-[2-Chloro-4-(3,5-dioxo-4,5-dihydro-3H-[1,2,4]triazin-2-yl)-6-methyl-phenoxy]-2-hydroxy-phenyl}-C-(3-trifluoromethyl-phenyl)-methanesulfonamide MS Calc.:583.0; Found:581.1.

EXAMPLE 12-28

N-{5-[2-Chloro-4-(3,5-dioxo-4,5-dihydro-3H-[1,2,4]triazin-2-yl)-6-methyl-phenoxy]-2-hydroxy-phenyl}-C-o-tolyl-methanesulfonamide MS Calc.:529.0; Found:527.1.

EXAMPLE 12-29

N-{5-[2-Chloro-4-(3,5-dioxo-4,5-dihydro-3H-[1,2,4]triazin-2-yl)-6-methyl-phenoxy]-2-hydroxy-phenyl}-C-(2,3,4,5,6-pentafluoro-phenyl)-methanesulfonamide MS Calc.:604.9; Found:603.0.

EXAMPLE 12-30

N-{5-[2-Chloro-4-(3,5-dioxo-4,5-dihydro-3H-[1,2,4]triazin-2-yl)-6-methyl-phenoxy]-2-hydroxy-phenyl}-C-indan-5-yl-methanesulfonamide MS Calc.:555.0; Found:553.2.

EXAMPLE 13

2-{3-Chloro-4-[3-(benzenesulfonyl)-4-hydroxy-phenoxy]-5-methyl-phenyl}-2H-[1,2,4]triazine-3,5-dione Step A 2-{3-Chloro-4-[3-(benzenesulfonyl)-4-methoxy-phenoxy]-5-methyl-phenyl}-2H-[1,2,4]triazine-3,5-dione A mixture of 2-{3-chloro-4-[4-methoxy-phenoxy]-5-methyl-phenyl}-2H-[1,2,4]triazine-3,5-dione (1.0 g) and benzenesulfonic acid (0.9 g) in Eaton's reagent (5 mL) was heated at 80° C. for 8 h. The reaction was poured over ice, stirred for 30 min, solids filtered, dried and flash chromatographed on silica gel (30–100% THF/hexanes) to afford the title compound of Step A, 0.66 g.

Step B

2-{3-Chloro-4-[3-(benzenesulfonyl)-4-hydroxy-phenoxy]-5-methyl-phenyl}-2H-[1,2,4]triazine-3,5-dione To a stirred solution of 2-{3-chloro-4-[3-(benzenesulfonyl)-4-methoxy-phenoxy]-5-methyl-phenyl}-2H-[1,2,4]triazine-3,5-dione (0.66 g) in dichloromethane (12 mL) was added boron trichloride (8 mL, 1M in dichloromethane) and the resulting solution was stirred for 4 h. The reaction solution was poured onto ice, allowed to stir for 1 h, the phases separated and the aqueous layer washed with dichloromethane. The combined organic layers were dried ($Na_2SO_4$) and concentrated to afford the title compound of this EXAMPLE as a tan foam, 0.52 g. m.p. 78–81° C.

Using the appropriate starting materials, EXAMPLES 13-1 to 13-8 were prepared in an analogous manner to that described in EXAMPLE 13.

EXAMPLE 13-1

2-{3-Chloro-4-[3-(4-chloro-benzenesulfonyl)-4-hydroxy-phenoxy]-5-methyl-phenyl}-2H-[1,2,4]triazine-3,5-dione MS Calc.:520.4; Found:518.1.

EXAMPLE 13-2

2-{3-Chloro-4-[4-hydroxy-3-(indane-5-sulfonyl)-phenoxy]-5-methyl-phenyl}-2H-[1,2,4]triazine-3,5-dione MS Calc.:526.0; Found:524.2.

EXAMPLE 13-3

2-{3,5-Dichloro-4-[3-(4-chloro-benzenesulfonyl)-4-hydroxy-phenoxy]-phenyl}-2H-[1,2,4]triazine-3,5-dione MS Calc.:540.8; Found:539.9.

EXAMPLE 13-4

2-{3,5-Dichloro-4-[4-hydroxy-3-(indane-5-sulfonyl)-phenoxy]-phenyl}-2H-[1,2,4]triazine-3,5-dione MS Calc.:546.4; Found:544.1.

EXAMPLE 13-5

2-{3,5-Dichloro-4-[4-hydroxy-3-(naphthalene-2-sulfonyl)-phenoxy]-phenyl}-2H-[1,2,4]triazine-3,5-dione MS Calc.:556.4; Found:554.1.

EXAMPLE 13-6

2-{3,5-Dichloro-4-[3-(4-ethyl-benzenesulfonyl)-4-hydroxy-phenoxy]-phenyl}-2H-[1,2,4]triazine-3,5-dione MS Calc.:534.4; Found:532.0.

EXAMPLE 13-7

2-{3,5-Dichloro-4-[4-hydroxy-3-(4-octyl-benzenesulfonyl)-phenoxy]-phenyl}-2H-[1,2,4]triazine-3,5-dione MS Calc.:618.5; Found:616.1.

EXAMPLE 13-8

2-{3,5-Dichloro-4-[3-(hexane-1-sulfonyl)-4-hydroxy-phenoxy]-phenyl}-2H-[1,2,4]triazine-3,5-dione MS Calc.:514.4; Found:512.1.

EXAMPLE 14

2-[3-Chloro-4-[3-(4-fluoro-benzyl)-4-hydroxy-phenoxy]-5-methyl-phenyl]-2H-[1,2,4]triazine-3,5-dione

Step A

2-{3-Chloro-4-[3-(4-fluoro-benzoyl)-4-methoxy-phenoxy]-5-methyl-phenyl}-2H-[1,2,4]triazine-3,5-dione A solution of 2-{3-chloro-4-[4-methoxy-phenoxy]-5-methyl-phenyl}-2H-[1,2,4]triazine-3,5-dione (1.2 g) and p-fluorobenzoic acid (0.8 g) in Eaton's acid (5 mL) was heated at 60° C. for 4 h. The resulting red solution was cooled to 0° C., water (30 mL) added and the suspension stirred at room temperature for 30 min. The mixture was extracted with ethyl acetate (2×), the combined organic layers washed with saturated aqueous sodium bicarbonate, dried ($Na_2SO_4$), concentrated in vacuo and flashed chromatographed on silica gel (25–40% THF/hexanes) to afford the title compound of Step A as a off-white foam, 1.1 g. MS Calc.:481.9; Found:481.8.

Step B

2-{(3-Chloro-4-[3-(4-fluoro-benzoyl)-4-hydroxy-phenoxy]-5-methyl-phenyl}-2H-[1,2,4]triazine-3,5-dione To a stirred solution of 2-{3-chloro-4-[3-(4-fluoro-benzoyl)-4-methoxy-phenoxy]-5-methyl-phenyl}-2H-[1,2,4]triazine-3,5-dione (1.1 g) in dichloromethane (30 mL) was added a solution of 1M boron trichloride in dichloromethane (11 mL) and the resulting suspension was stirred at ambient temperature for 4 h. Ice was added to the reaction and the resulting mixture was stirred for 30 min, extracted with ethyl acetate, the organic phase dried ($Na_2SO_4$), concentrated in vacuo and flash chromatographed on silica gel (30% THF/hexanes) to afford the title compound of Step B, 0.94 g. MS Calc.:467.8 Found:467.8.

Step C 2-(3-Chloro-4-{3-[(4-fluoro-phenyl)-hydroxy-methyl]-4-hydroxy-phenoxy}-5-methyl-phenyl)-2H-[1,2,4]triazine-3,5-dione To a cooled (0° C.), stirred solution of 2-{3-chloro-4-[3-(4-fluoro-benzoyl)-4-hydroxy-phenoxy]-5-methyl-phenyl}-2H-[1,2,4]triazine-3,5-dione (0.4 g) in methanol (10 mL) was added sodium borohydride (32 mg). After 30 min, the reaction solution was concentrated in vacuo, partitioned between 1N hydrochloric acid and ethyl acetate, the organic phase dried (Na$_2$SO$_4$), concentrated in vacuo and flash chromatographed on silica gel (5% ethanol/dichloromethane) to afford the title compound of Step C as a colorless foam, 72 mg. MS Calc.:469.8; Found:467.9.

Step D

2-{(3-Chloro-4-[3-(4-fluoro-benzyl)-4-hydroxy-phenoxy]-5-methyl-phenyl}-2H-[1,2,4]triazine-3,5-dione To a stirred solution of 2-(3-chloro-4-{3-[(4-fluoro-phenyl)-hydroxy-methyl]-4-hydroxy-phenoxy}-5-methyl-phenyl)-2H-[1,2,4]triazine-3,5-dione (0.4 g) in dichloromethane (25 mL) were added methanesulfonic acid (0.7 mL) and triethylsilane (1.5 mL) portionwise over 1 h. After a total of 1.5 h, water was added, the layers separated and the aqueous layer extracted with dichloromethane. The combined organic layers were washed with saturated sodium bicarbonate, dried (Na$_2$SO$_4$), concentrated in vacuo and flash chromatographed on silica gel (10–50% THF/hexanes) to afford the title compound of this EXAMPLE as a colorless foam, 56 mg. MS Calc.:453.9; Found:452.

Using the appropriate starting materials, EXAMPLES 14-1 to 14-29 were prepared in an analogous manner to that described in EXAMPLE 14.

EXAMPLE 14-1

2-{4-[3-(4-Fluoro-benzoyl)-4-methoxy-phenoxy]-3,5-dimethyl-phenyl}-2H-[1,2,4]triazine-3,5-dione MS Calc.: 461.4; Found: 462.2.

EXAMPLE 14-2

2-{4-[3-(4-Fluoro-benzyl)-4-methoxy-phenoxy]-3,5-dimethyl-phenyl}-2H-[1,2,4]triazine-3,5-dione m.p. 57–60° C. (dec).

EXAMPLE 14-3

2-{4-[3-(4-Fluoro-benzoyl)-4-hydroxy-phenoxy]-3,5-dimethyl-phenyl}-2H-[1,2,4]triazine-3,5-dione m.p. 68–72° C.

EXAMPLE 14-4

2-(4-{3-[(4-Fluoro-phenyl)-hydroxy-methyl]-4-hydroxy-phenoxy}-3,5-dimethyl-phenyl-2H-[1,2,4]triazine-3,5-dione m.p. 95–110° C. (dec).

EXAMPLE 14-5

2-{4-[3-(4-Fluoro-benzyl)-4-hydroxy-phenoxy]-3,5-dimethyl-phenyl}-2H-[1,2,4]triazine-3,5-dione m.p. 72–75° C. (dec).

EXAMPLE 14-6

2-{4-[3-(4-Fluoro-benzoyl)-4-methoxy-phenoxy]-3,5-dimethyl-phenyl}-4-methyl-2H-[1,2,4]triazine-3,5-dione MS Calc.:475.5; Found:476.2.

EXAMPLE 14-7

2-{3,5-Dichloro-4-[3-(4-fluoro-benzoyl)-4-hydroxy-phenoxy]-phenyl}-2H-[1,2,4]triazine-3,5-dione MS Calc.:488.3; Found:487.9.

EXAMPLE 14-8

4-{5-[4-(3,5-Dioxo-4,5-dihydro-3H-[1,2,4]triazin-2-yl)-2,6-dimethyl-phenoxy]-2-methoxy-benzoyl}-benzamide MS Calc.:486.5; Found:486.9.

EXAMPLE 14-9

2-(3,5-Dichloro-4-{3-[(4-fluoro-phenyl)-(R,S)-hydroxy-methyl]-4-hydroxy-phenoxy}-phenyl)-2H-[1,2,4]triazine-3,5-dione m.p. 85–89° C. (dec).

EXAMPLE 14-10

2-{3,5-Dichloro-4-[3-(4-fluoro-benzyl)-4-hydroxy-phenoxy]-phenyl}-2H-[1,2,4]triazine-3,5-dione m.p. 85–91° C. (dec).

EXAMPLE 14-11

2-{4-[3-(4-Dimethylamino-benzoyl)-4-methoxy-phenoxy]-3,5-dimethyl-phenyl}-2H-[1,2,4]triazine-3,5-dione MS Calc.:486.5; Found:486.9.

EXAMPLE 14-12

4-{5-[2,6-Dichloro-4-(3,5-dioxo-4,5-dihydro-3H-[1,2,4]triazin-2-yl)-phenoxy]-2-methoxy-benzoyl}-benzamide MS Calc.:527.3; Found:527.0.

EXAMPLE 14-13

4-{5-[4-(3,5-Dioxo-4,5-dihydro-3H-[1,2,4]triazin-2-yl)-2,6-dimethyl-phenoxy]-2-hydroxy-benzoyl}-benzamide MS Calc.:472.5; Found:472.9.

EXAMPLE 14-14

2-{4-[3-(4-Dimethylamino-benzoyl)-4-hydroxy-phenoxy]-3,5-dimethyl-phenyl}-2H-[1,2,4]triazine-3,5-dione MS Calc.:472.5; Found:472.9.

EXAMPLE 14-15

2-{3,5-Dichloro-4-[3-(4-dimethylamino-benzoyl)-4-methoxy-phenoxy]-phenyl}-2H-[1,2,4]triazine-3,5-dione m.p. 222–230° C.

EXAMPLE 14-16

4-{5-[2,6-Dichloro-4-(3,5-dioxo-4,5-dihydro-3H-[1,2,4]triazin-2-yl)-phenoxy]-2-hydroxy-benzoyl}-benzamide m.p. 140–145° C.

EXAMPLE 14-17

4-{5-[2,6-Dichloro-4-(3,5-dioxo-4,5-dihydro-3H-[1,2,4]triazin-2-yl)-phenoxy]-2-hydroxy-phenyl}-hydroxy-methyl)-benzamide MS Calc.:515.3; Found:515.0.

EXAMPLE 14-18

2-[3,5-Dichloro-4-(4-hydroxy-3-isobutyryl-phenoxy)-phenyl]-2H-[1,2,4]triazine-3,5-dione MS Calc.:436.3; Found:435.9.

EXAMPLE 14-19

4-({5-[4-(3,5-Dioxo-4,5-dihydro-3H-[1,2,4]triazin-2-yl)-2,6-dimethyl-phenoxy]-2-hydroxy-phenyl}-hydroxy-methyl)-benzamide MS Calc.:474.5; Found:473 (M−1).

EXAMPLE 14-20

2-{4-[3-(4-Dimethylamino-benzyl)-4-hydroxy-phenoxy]-3,5-dimethyl-phenyl}-2H-[1,2,4]triazine-3,5-dione MS Calc.:458.5; Found:459.

EXAMPLE 14-21

2-{3,5-Dichloro-4-[3-(4-dimethylamino-benzoyl)-4-hydroxy-phenoxy]-phenyl}-2H-[1,2,4]triazine-3,5-dione MS Calc.:513.3; Found:513.

EXAMPLE 14-22

2-{3,5-Dichloro-4-[4-hydroxy-3-(1-hydroxy-2-methyl-propyl)-phenoxy]-phenyl}-2H-[1,2,4]triazine-3,5-dione m.p. 192–195° C.

EXAMPLE 14-23

2-(3,5-Dichloro-4-{3-[(4-dimethylamino-phenyl)-hydroxy-methyl]-4-hydroxy-phenoxy}-phenyl)-2H-[1,2,4]triazine-3,5-dione MS Calc.:515.4; Found:515.0.

EXAMPLE 14-24

2-{3,5-Dichloro-4-[3-(4-dimethylamino-benzyl)-4-hydroxy-phenoxy]-phenyl}-2H-[1,2,4]triazine-3,5-dione MS Calc.:499.4; Found:499.0.

EXAMPLE 14-25

2-[3,5-Dichloro-4-(4-hydroxy-3-isobutyl-phenoxy)-phenyl]-2H-[1,2,4]triazine-3,5-dione MS Calc.:422.3; Found:420.0.

EXAMPLE 14-26

(2-{4-[3-(4-Fluoro-benzoyl)-4-hydroxy-phenoxy]-3,5-dimethyl-phenyl}-3,5-dioxo-2,5-dihydro-3H-[1,2,4]triazin-4-yl)-acetic acid m.p. 112–116° C.

EXAMPLE 14-27

2-{3,5-Dibromo-4-[3-(4-fluoro-benzoyl)-4-hydroxy-phenoxy]-phenyl}-2H-[1,2,4]triazine-3,5-dione MS Calc.:577.2; Found:575.8.

EXAMPLE 14-28

2-(3,5-Dibromo-4-{3-[(4-fluoro-phenyl)-hydroxy-methyl]-4-hydroxy-phenoxy}-phenyl)-2H-[1,2,4]triazine-3,5-dione MS Calc.:579.2; Found:578.0.

EXAMPLE 14-29

2-{3,5-Dibromo-4-[3-(4-fluoro-benzyl)-4-hydroxy-phenoxy]-phenyl}-2H-[1,2,4]triazine-3,5-dione MS Calc.:563.2; Found:562.0.

EXAMPLE 15

2-{3,5-Dichloro-4-[4-hydroxy-3-(piperidine-1-sulfonyl)-phenoxy]-phenyl}-2H-[1,2,4]triazine-3,5-dione

Step A

2-[3,5-Dichloro-4-(3-chlorosulfonyl-4-methoxy-phenoxy)-phenyl]-2H-[1,2,4]triazine-3,5-dione To a cooled (0° C.), stirred solution of chlorosulfonic acid (1 mL) was added 2-[3,5-dichloro-4-(4-methoxy-phenoxy)-phenyl]-2H-[1,2,4]triazine-3,5-dione (0.6 g). After 30 min, the resulting brown solution was poured over ice and the resulting mixture was allowed to stir at ambient temperature for 30 min, the solids filtered and dried in vacuo to afford the title compound of Step A as a colorless solid, 0.7 g.

Step B

2-{3,5-Dichloro-4-[4-methoxy-3-(piperidine-1-sulfonyl)-phenoxy]-phenyl}-2H-[1,2,4]triazine-3,5-dione To a stirred solution of 2-[3,5-dichloro-4-(3-chlorosulfonyl-4-methoxy-phenoxy)-phenyl]-2H-[1,2,4]triazine-3,5-dione (0.7 g) in dimethylformamide (8 mL) was added piperidine (0.4 mL). After 1 h, the reaction was diluted in diethyl ether, washed with 1N hydrochloric acid, brine, dried (Na$_2$SO$_4$) and concentrated in vacuo to a solid. Recrystallization from diethyl ether/petroleum ether afforded the title compound of Step B, 0.5 g. MS Calc.:527.4 Found:527.0.

Step C

2-{3,5-Dichloro-4-[4-hydroxy-3-(piperidine-1-sulfonyl)-phenoxy]-phenyl}-2H-[1,2,4]triazine-3,5-dione To a cooled (0° C.), stirred solution of 2-{3,5-dichloro-4-[4-methoxy-3-(piperidine-1-sulfonyl)-phenoxy]-phenyl}-2H-[1,2,4]triazine-3,5-dione (0.5 g) in dichloromethane (30 mL) was added boron tribromide (0.3 mL) and the resulting heterogeneous mixture was allowed to stir at room temperature for 6 h. Ice was added to the mixture and the resulting two-phase solution stirred for 1 h. Layers were separated and the organic phase was washed with water, brine, dried (Na$_2$SO$_4$) and concentrated in vacuo to afford an oil. Flash chromatography on silica gel (35% acetone/hexanes) afforded the title compound of this EXAMPLE as a colorless solid, 0.4 g. MS Calc.:513.4 Found:512.9.

Using the appropriate starting materials, EXAMPLES 15-1 to 15-87 were prepared in an analogous manner to that described in EXAMPLE 15.

EXAMPLE 15-1

2-{4-[4-Hydroxy-3-(piperidine-1-sulfonyl)-phenoxy]-3,5-dimethyl-phenyl}-2H-[1,2,4]triazine-3,5-dione MS Calc.:472.5; Found:473.1.

EXAMPLE 15-2

2-{3-Chloro-4-[4-hydroxy-3-(piperidine-1-sulfonyl)-phenoxy]-5-methyl-phenyl}-2H-[1,2,4]triazine-3,5-dione MS Calc.:492.9; Found:490.9 (M−1).

EXAMPLE 15-3

5-[4-(3,5-Dioxo-4,5-dihydro-3H-[1,2,4]triazin-2-yl)-2,6-dimethyl-phenoxy]-2-hydroxy-N-phenyl-benzenesulfonamide MS Calc.:480.5; Found:479.0.

EXAMPLE 15-4

5-[2-Chloro-4-(3,5-dioxo-4,5-dihydro-3H-[1,2,4]triazin-2-yl)-6-methyl-phenoxy]-2-hydroxy-N-phenyl-benzenesulfonamide MS Calc.:500.9; Found:498.9.

EXAMPLE 15-5

2-{4-[4-Hydroxy-3-(pyrrolidine-1-sulfonyl)-phenoxy]-3,5-dimethyl-phenyl}-2H-[1,2,4]triazine-3,5-dione MS Calc.:458.5; Found:458.9.

EXAMPLE 15-6

2-{3-Chloro-4-[4-hydroxy-3-(pyrrolidine-1-sulfonyl)-phenoxy]-5-methyl-phenyl}-2H-[1,2,4]triazine-3,5-dione MS Calc.:478.9; Found:478.9.

EXAMPLE 15-7

2-{3-Chloro-4-[4-hydroxy-3-(4-methyl-piperazine-1-sulfonyl)-phenoxy]-5-methyl-phenyl}-2H-[1,2,4]triazine-3,5-dione MS Calc.:507.9; Found:505.9.

EXAMPLE 15-8

2-{3-Chloro-4-[4-hydroxy-3-(morpholine-4-sulfonyl)-phenoxy]-5-methyl-phenyl}-2H-[1,2,4]triazine-3,5-dione MS Calc.:494.9; Found:494.9.

EXAMPLE 15-9

5-[2-Chloro-4-(3,5-dioxo-4,5-dihydro-3H-[1,2,4]triazin-2-yl)-6-methyl-phenoxy]-2-hydroxy-N-pyrimidin-4-yl-benzenesulfonamide MS Calc.:502.9; Found:502.9.

EXAMPLE 15-10

2-{3-Chloro-4-[3-(3,3-dioxo-1H-thiazolidine-sulfonyl)-4-hydroxy-phenoxy]-5-methyl-phenyl}-2H-[1,2,4]triazine-3,5-dione m.p. 53–55° C.

EXAMPLE 15-11

5-[2-Chloro-4-(3,5-dioxo-4,5-dihydro-3H-[1,2,4]triazin-2-yl)-6-methyl-phenoxy]-N-cyclohexyl-2-hydroxy-benzenesulfonamide MS Calc.:507.0; Found:506.8.

EXAMPLE 15-12

5-[2-Chloro-4-(3,5-dioxo-4,5-dihydro-3H-[1,2,4]triazin-2-yl)-6-methyl-phenoxy]-2-hydroxy-N-(1-methyl-1H-benzoimidazol-2-yl)-benzenesulfonamide MS Calc.:555.0; Found:555.0.

EXAMPLE 15-13

5-[2-Chloro-4-(3,5-dioxo-4,5-dihydro-3H-[1,2,4]triazin-2-yl)-6-methyl-phenoxy]-2-hydroxy-N-(2-methoxy-ethyl)-benzenesulfonamide MS Calc.:482.9; Found:482.8.

EXAMPLE 15-14

2-{3,5-Dibromo-4-[4-hydroxy-3-(piperidine-1-sulfonyl)-phenoxy]-phenyl}-2H-[1,2,4]triazine-3,5-dione m.p. 181-183° C.

EXAMPLE 15-15

5-[2,6-Dibromo-4-(3,5-dioxo-4,5-dihydro-3H-[1,2,4]triazin-2-yl)-phenoxy]-N,N-diethyl-2-hydroxy-benzenesulfonamide MS Calc.:590.2; Found:588.9.

EXAMPLE 15-16

2-{3,5-Dibromo-4-[4-hydroxy-3-(pyrrolidine-1-sulfonyl)-phenoxy]-phenyl}-2H-[1,2,4]triazine-3,5-dione MS Calc.:588.2; Found:588.8.

EXAMPLE 15-17

5-[2-Chloro-4-(3,5-dioxo-4,5-dihydro-3H-[1,2,4]triazin-2-yl)-6-methyl-phenoxy]-N-(4-fluoro-phenyl)-2-hydroxy-benzenesulfonamide MS Calc.:518.9; Found:516.8.

EXAMPLE 15-18

2-{3,5-Dichloro-4-[4-hydroxy-3-(1,3,3-trimethyl-6-aza-bicyclo[3.2.1]octane-6-sulfonyl)-phenoxy]-phenyl}-2H-[1,2,4]triazine-3,5-dione MS Calc.:581.5; Found:581.0.

EXAMPLE 15-19

5-[2,6-Dichloro-4-(3,5-dioxo-4,5-dihydro-3H-[1,2,4]triazin-2-yl)-phenoxy]-2-hydroxy-N-phenyl-benzenesulfonamide MS Calc.:521.3; Found:519.0.

EXAMPLE 15-20

5-[2,6-Dichloro-4-(3,5-dioxo-4,5-dihydro-3H-[1,2,4]triazin-2-yl)-phenoxy]-2-hydroxy-N-methyl-N-phenyl-benzenesulfonamide MS Calc.:535.4; Found:533.0.

EXAMPLE 15-21

N-Benzyl-5-[2,6-dichloro-4-(3,5-dioxo-4,5-dihydro-3H-[1,2,4]triazin-2-yl)-phenoxy]-2-hydroxy-N-methyl-benzenesulfonamide MS Calc.:549.4; Found:547.1.

EXAMPLE 15-22

2-{3,5-Dichloro-4-[3-(2,3-dihydro-indole-1-sulfonyl)-4-hydroxy-phenoxy]-phenyl}-2H-[1,2,4]triazine-3,5-dione MS Calc.:547.4; Found:545.1.

EXAMPLE 15-23

5-[2,6-Dichloro-4-(3,5-dioxo-4,5-dihydro-3H-[1,2,4]triazin-2-yl)-phenoxy]-2-hydroxy-N-indan-1-yl-benzenesulfonamide MS Calc.:561.4; Found:559.0.

EXAMPLE 15-24

5-[2,6-Dichloro-4-(3,5-dioxo-4,5-dihydro-3H-[1,2,4]triazin-2-yl)-phenoxy]-N-(4-fluoro-phenyl)-2-hydroxy-benzenesulfonamide MS Calc.:539.3; Found:537.0.

EXAMPLE 15-25

2-{3,5-Dichloro-4-[4-hydroxy-3-(pyrrolidine-1-sulfonyl)-phenoxy]-phenyl}-2H-[1,2,4]triazine-3,5-dione MS Calc.:499.3; Found:499.0.

EXAMPLE 15-26

5-[2,6-Dichloro-4-(3,5-dioxo-4,5-dihydro-3H-[1,2,4]triazin-2-yl)-phenoxy]-2-hydroxy-N-p-tolyl-benzenesulfonamide MS Calc.:535.4; Found:533.1.

EXAMPLE 15-27

N-Cyclohexyl-5-[2,6-dichloro-4-(3,5-dioxo-4,5-dihydro-3H-[1,2,4]triazin-2-yl)-phenoxy]-N-ethyl-2-hydroxy-benzenesulfonamide MS Calc.:555.4; Found:553.2.

EXAMPLE 15-28

N-Cyclopropyl-5-[2,6-dichloro-4-(3,5-dioxo-4,5-dihydro-3H-[1,2,4]triazin-2-yl)-phenoxy]-2-hydroxy-benzenesulfonamide MS Calc.:485.3; Found:483.1.

EXAMPLE 15-29

N-Cyclobutyl-5-[2,6-dichloro-4-(3,5-dioxo-4,5-dihydro-3H-[1,2,4]triazin-2-yl)-phenoxy]-2-hydroxy-benzenesulfonamide MS Calc.:499.3; Found:497.1.

EXAMPLE 15-30

5-[2,6-Dichloro-4-(3,5-dioxo-4,5-dihydro-3H-[1,2,4]triazin-2-yl)-phenoxy]-N-furan-2-ylmethyl-2-hydroxy-benzenesulfonamide MS Calc.:525.3; Found:523.0.

EXAMPLE 15-31

N-(2-Chloro-benzyl)-5-[2,6-dichloro-4-(3,5-dioxo-4,5-dihydro-3H-[1,2,4]triazin-2-yl)-phenoxy]-2-hydroxy-benzenesulfonamide MS Calc.:569.8; Found:567.0.

EXAMPLE 15-32

N-Cyclohexyl-5-[2,6-dichloro-4-(3,5-dioxo-4,5-dihydro-3H-[1,2,4]triazin-2-yl)-phenoxy]-2-hydroxy-N-methyl-benzenesulfonamide MS Calc.:541.4; Found:539.1.

EXAMPLE 15-33

5-[2,6-Dichloro-4-(3,5-dioxo-4,5-dihydro-3H-[1,2,4]triazin-2-yl)-phenoxy]-2-hydroxy-N-(1-methyl-2-phenoxy-ethyl)-benzenesulfonamide MS Calc.:579.4; Found:577.1.

EXAMPLE 15-34

2-{3,5-Dichloro-4-[4-hydroxy-3-(3,3,5-trimethyl-azepane-1-sulfonyl)-phenoxy]-phenyl}-2H-[1,2,4]triazine-3,5-dione MS Calc.:569.5; Found:567.2.

EXAMPLE 15-35

5-[2,6-Dichloro-4-(3,5-dioxo-4,5-dihydro-3H-[1,2,4]triazin-2-yl)-phenoxy]-2-hydroxy-N-thiophen-2-ylmethyl-benzenesulfonamide MS Calc.:541.4; Found:539.0.

EXAMPLE 15-36

N-Cyclohexyl-5-[2,6-dichloro-4-(3,5-dioxo-4,5-dihydro-3H-[1,2,4]triazin-2-yl)-phenoxy]-2-hydroxy-benzenesulfonamide MS Calc.:527.4; Found:525.0.

EXAMPLE 15-37

N-Benzyl-5-[2,6-dichloro-4-(3,5-dioxo-4,5-dihydro-3H-[1,2,4]triazin-2-yl)-phenoxy]-2-hydroxy-benzenesulfonamide MS Calc.:535.4; Found:533.0.

EXAMPLE 15-38

5-[2,6-Dichloro-4-(3,5-dioxo-4,5-dihydro-3H-[1,2,4]triazin-2-yl)-phenoxy]-2-hydroxy-N-o-tolyl-benzenesulfonamide MS Calc.:535.4 Found:533.1.

EXAMPLE 15-39

2-{3,5-Dichloro-4-[3-(3,4-dihydro-1H-isoquinoline-2-sulfonyl)-4-hydroxy-phenoxy]-phenyl}-2H-[1,2,4]triazine-3,5-dione MS Calc.:561.4; Found:559.0.

EXAMPLE 15-40

5-[2,6-Dichloro-4-(3,5-dioxo-4,5-dihydro-3H-[1,2,4]triazin-2-yl)-phenoxy]-N-(1,1-dimethyl-propyl)-2-hydroxy-benzenesulfonamide MS Calc.:515.4; Found:513.1.

EXAMPLE 15-41

5-[2,6-Dichloro-4-(3,5-dioxo-4,5-dihydro-3H-[1,2,4]triazin-2-yl)-phenoxy]-2-hydroxy-N-(4-methyl-cyclohexyl)-benzenesulfonamide MS Calc.:541.4; Found:539.0.

EXAMPLE 15-42

2-{3,5-Dichloro-4-[4-hydroxy-3-(3-methyl-3-phenyl-piperidine-1-sulfonyl)-phenoxy]-phenyl}-2H-[1,2,4]triazine-3,5-dione MS Calc.:603.5; Found:603.0.

EXAMPLE 15-43

N-(1-Cyclohexyl-ethyl)-5-[2,6-dichloro-4-(3,5-dioxo-4,5-dihydro-3H-[1,2,4]triazin-2-yl)-phenoxy]-2-hydroxy-benzenesulfonamide MS Calc.:555.4 Found:553.2.

EXAMPLE 15-44

N-Cyclohexylmethyl-5-[2,6-dichloro-4-(3,5-dioxo-4,5-dihydro-3H-[1,2,4]triazin-2-yl)-phenoxy]-2-hydroxy-benzenesulfonamide MS Calc.:541.4; Found:539.1.

EXAMPLE 15-45

5-[2,6-Dichloro-4-(3,5-dioxo-4,5-dihydro-3H-[1,2,4]triazin-2-yl)-phenoxy]-2-hydroxy-N-(2-phenyl-propyl)-benzenesulfonamide MS Calc.:563.4; Found:560.9.

EXAMPLE 15-46

5-[2,6-Dichloro-4-(3,5-dioxo-4,5-dihydro-3H-[1,2,4]triazin-2-yl)-phenoxy]-2-hydroxy-N-(2-phenyl-cyclopropyl)-benzenesulfonamide MS Calc.:561.4; Found:558.9.

EXAMPLE 15-47

2-{3,5-Dichloro-4-[4-hydroxy-3-(4-methyl-piperidine-1-sulfonyl)-phenoxy]-phenyl}-2H-[1,2,4]triazine-3,5-dione MS Calc.:527.4; Found:525.0.

EXAMPLE 15-48

2-{3,5-Dichloro-4-[4-hydroxy-3-(4-hydroxy-piperidine-1-sulfonyl)-phenoxy]-phenyl}-2H-[1,2,4]triazine-3,5-dione MS Calc.:529.4; Found:527.0.

EXAMPLE 15-49

N-(6-Chloro-pyridin-3-yl)-5-[2,6-dichloro-4-(3,5-dioxo-4,5-dihydro-3H-[1,2,4]triazin-2-yl)-phenoxy]-2-hydroxy-benzenesulfonamide MS Calc.:556.8; Found:555.8.

EXAMPLE 15-50

2-{3,5-Dichloro-4-[4-hydroxy-3-(3-cyclohexyl-piperidine-1-sulfonyl)-phenoxy]-phenyl}-2H-[1,2,4]triazine-3,5-dione MS Calc.:595.5; Found:594.9.

EXAMPLE 15-51

2-{3,5-Dichloro-4-[4-hydroxy-3-(3-phenyl-piperidine-1-sulfonyl)-phenoxy]-phenyl}-2H-[1,2,4]triazine-3,5-dione MS Calc.:589.5; Found:588.9.

EXAMPLE 15-52

2-{3,5-Dichloro-4-[4-hydroxy-3-(3-methyl-3-phenyl-pyrrolidine-1-sulfonyl)-phenoxy]-phenyl}-2H-[1,2,4]triazine-3,5-dione MS Calc.:589.5; Found:588.9.

EXAMPLE 15-53

2-{3,5-Dichloro-4-[4-hydroxy-3-(2-methyl-2,3-dihydro-indole-1-sulfonyl)-phenoxy]-phenyl}-2H-[1,2,4]triazine-3,5-dione MS Calc.:561.4; Found:560.9.

EXAMPLE 15-54

2-{3,5-Dichloro-4-[3-(2,3-dimethyl-2,3-dihydro-indole-1-sulfonyl)-4-hydroxy-phenoxy]-phenyl}-2H-[1,2,4]triazine-3,5-dione MS Calc.:575.4; Found:574.9.

EXAMPLE 15-55

5-[2,6-Dichloro-4-(3,5-dioxo-4,5-dihydro-3H-[1,2,4]triazin-2-yl)-phenoxy]-N-(2,2-diphenyl-ethyl)-2-hydroxy-benzenesulfonamide MS Calc.:625.5; Found:623.0.

EXAMPLE 15-56

5-[2,6-Dichloro-4-(3,5-dioxo-4,5-dihydro-3H-[1,2,4]triazin-2-yl)-phenoxy]-N-[2-(2,4-dichloro-phenyl)-ethyl]-2-hydroxy-benzenesulfonamide MS Calc.:618.3 Found:616.9.

EXAMPLE 15-57

N-[2-(4-Chloro-phenyl)-1-methyl-ethyl]-5-[2,6-dichloro-4-(3,5-dioxo-4,5-dihydro-3H-[1,2,4]triazin-2-yl)-phenoxy]-2-hydroxy-benzenesulfonamide MS Calc.:597.9; Found:596.9.

EXAMPLE 15-58

5-[2,6-Dichloro-4-(3,5-dioxo-4,5-dihydro-3H-[1,2,4]triazin-2-yl)-phenoxy]-2-hydroxy-N-(3-oxazol-5-yl-phenyl)-benzenesulfonamide MS Calc.:588.4; Found:587.8.

EXAMPLE 15-59

5-[2,6-Dichloro-4-(3,5-dioxo-4,5-dihydro-3H-[1,2,4]triazin-2-yl)-phenoxy]-N-[2-(4-fluoro-phenyl)-ethyl]-2-hydroxy-benzenesulfonamide MS Calc.:567.4; Found:564.9.

EXAMPLE 15-60

5-[2,6-Dichloro-4-(3,5-dioxo-4,5-dihydro-3H-[1,2,4]triazin-2-yl)-phenoxy]-2-hydroxy-N-methyl-N-phenethyl-benzenesulfonamide MS Calc.:563.4; Found:560.9.

EXAMPLE 15-61

N-[2-(4-Chloro-phenyl)-1-methyl-ethyl]-5-[2,6-dichloro-4-(3,5-dioxo-4,5-dihydro-3H-[1,2,4]triazin-2-yl)-phenoxy]-2-hydroxy-N-methyl-benzenesulfonamide MS Calc.:611.9; Found:610.9.

EXAMPLE 15-62

5-[2,6-Dichloro-4-(3,5-dioxo-4,5-dihydro-3H-[1,2,4]triazin-2-yl)-phenoxy]-2-hydroxy-N-phenethyl-benzenesulfonamide MS Calc.:549.4; Found:546.9.

EXAMPLE 15-63

2-{4-[3-(2-Benzyl-piperidine-1-sulfonyl)-4-hydroxy-phenoxy]-3,5-dichloro-phenyl}-2H-[1,2,4]triazine-3,5-dione MS Calc.:603.5; Found:602.9.

EXAMPLE 15-64

5-[2,6-Dichloro-4-(3,5-dioxo-4,5-dihydro-3H-[1,2,4]triazin-2-yl)-phenoxy]-2-hydroxy-N-(1,2,3,4-tetrahydro-naphthalen-2-yl)-benzenesulfonamide MS Calc.:575.4; Found:572.9.

EXAMPLE 15-65

N-[2-(4-Chloro-phenyl)-1,1-dimethyl-ethyl]-5-[2,6-dichloro-4-(3,5-dioxo-4,5-dihydro-3H-[1,2,4]triazin-2-yl)-phenoxy]-2-hydroxy-benzenesulfonamide MS Calc.:611.9; Found:608.9.

EXAMPLE 15-66

2-{3,5-Dichloro-4-[4-hydroxy-3-(4-phenyl-piperazine-1-sulfonyl)-phenoxy]-phenyl}-2H-[1,2,4]triazine-3,5-dione MS Calc.:590.4; Found:590.9.

EXAMPLE 15-67

2-{3,5-Dichloro-4-[3-(3,5-dimethyl-piperidine-1-sulfonyl)-4-hydroxy-phenoxy]-phenyl}-2H-[1,2,4]triazine-3,5-dione MS Calc.:541.4; Found:540.9.

EXAMPLE 15-68

5-[2,6-Dichloro-4-(3,5-dioxo-4,5-dihydro-3H-[1,2,4]triazin-2-yl)-phenoxy]-2-hydroxy-N-(1,2,3,4-tetrahydro-naphthalen-1-yl)-benzenesulfonamide MS Calc.:575.4; Found:573.2.

EXAMPLE 15-69

N-Bicyclo[2.2.1]hept-2-yl-5-[2,6-dichloro-4-(3,5-dioxo-4,5-dihydro-3H-[1,2,4]triazin-2-yl)-phenoxy]-2-hydroxy-benzenesulfonamide MS Calc.:539.4; Found:537.3.

EXAMPLE 15-70

5-[2,6-Dichloro-4-(3,5-dioxo-4,5-dihydro-3H-[1,2,4]triazin-2-yl)-phenoxy]-2-hydroxy-N-(1,7,7-trimethyl-bicyclo[2.2.1]hept-2-yl)-benzenesulfonamide MS Calc.:581.5; Found:579.3.

EXAMPLE 15-71

2-{3,5-Dichloro-4-[3-(3,3-dimethyl-piperidine-1-sulfonyl)-4-hydroxy-phenoxy]-phenyl}-2H-[1,2,4]triazine-3,5-dione MS Calc.:541.4; Found:539.3.

EXAMPLE 15-72

2-{3,5-Dichloro-4-[3-(3,3-dimethyl-piperidine-1-sulfonyl)-4-hydroxy-phenoxy]-phenyl}-2H-[1,2,4]triazine-3,5-dione MS Calc.:571.4; Found:569.2.

EXAMPLE 15-73

5-[2,6-Dichloro-4-(3,5-dioxo-4,5-dihydro-3H-[1,2,4]triazin-2-yl)-phenoxy]-2-hydroxy-N-(1(R)-phenyl-ethyl)-benzenesulfonamide MS Calc.:549.4; Found:547.2.

EXAMPLE 15-74

N-(4-Chloro-2-phenyl-2H-pyrazol-3-yl)-5-[2,6-dichloro-4-(3,5-dioxo-4,5-dihydro-3H-[1,2,4]triazin-2-yl)-phenoxy]-2-hydroxy-benzenesulfonamide MS Calc.:621.8; Found:621.1.

EXAMPLE 15-75

2-{3,5-Dichloro-4-[3-(2,3,4,4a,9,9a-hexahydro-indeno[2,1-b]pyridine-1-sulfonyl)-4-hydroxy-phenoxy]-phenyl}-2H-[1,2,4]triazine-3,5-dione MS Calc.:601.5; Found:601.1.

EXAMPLE 15-76

5-[2,6-Dichloro-4-(3,5-dioxo-4,5-dihydro-3H-[1,2,4]triazin-2-yl)-phenoxy]-2-hydroxy-N-(1-phenyl-ethyl)-benzenesulfonamide MS Calc.:549.4. Found:546.8.

EXAMPLE 15-77

2-{3,5-Dichloro-4-[4-hydroxy-3-(1,2,3,4-tetrahydro-1,4-epiazano-naphthalene-9-sulfonyl)-phenoxy]-phenyl}-2H-[1,2,4]triazine-3,5-dione MS Calc.:573.4; Found:570.9.

EXAMPLE 15-78

5-[2,6-Dichloro-4-(3,5-dioxo-4,5-dihydro-3H-[1,2,4]triazin-2-yl)-phenoxy]-N-(6,6-dimethyl-bicyclo[3.1.1]hept-2-yl)-2-hydroxy-benzenesulfonamide MS Calc.:567.4; Found:565.0.

EXAMPLE 15-79

5-[2,6-Dichloro-4-(3,5-dioxo-4,5-dihydro-3H-[1,2,4]triazin-2-yl)-phenoxy]-2-hydroxy-N-(3,3,5,5-tetramethyl-cyclohexyl)-benzenesulfonamide MS Calc.:583.5; Found:580.9.

EXAMPLE 15-80

5-[2,6-Dichloro-4-(3,5-dioxo-4,5-dihydro-3H-[1,2,4]triazin-2-yl)-phenoxy]-2-hydroxy-N-(1,1a,6,6a-tetrahydrocyclopropa[a]inden-1-yl)-benzenesulfonamide MS Calc.:573.4. Found:570.9.

EXAMPLE 15-81

N-Benzo[1,3]dioxol-5-ylmethyl-5-[2,6-dichloro-4-(3,5-dioxo-4,5-dihydro-3H-[1,2,4]triazin-2-yl)-phenoxy]-2-hydroxy-benzenesulfonamide MS Calc.:579.4; Found:576.9.

EXAMPLE 15-82

5-[2,6-Dichloro-4-(3,5-dioxo-4,5-dihydro-3H-[1,2,4]triazin-2-yl)-phenoxy]-2-hydroxy-N-(spiro(8-azabicyclo[3.2.1]octane-3,2'-[1,3]dioxolane))-benzenesulfonamide MS Calc.:597.4; Found:595.0.

EXAMPLE 15-83

N-Chroman-4-ylmethyl-5-[2,6-dichloro-4-(3,5-dioxo-4,5-dihydro-3H-[1,2,4]triazin-2-yl)-phenoxy]-2-hydroxy-N-methyl-benzenesulfonamide MS Calc.605.5; Found:602.9.

EXAMPLE 15-84

5-[2,6-Dichloro-4-(3,5-dioxo-4,5-dihydro-3H-[1,2,4]triazin-2-yl)-phenoxy]-2-hydroxy-N-(spiro(8-azabicyclo[3.2.1]octane3,2'(3'H)-furan))-benzenesulfonamide MS Calc.:595.5; Found:592.8.

EXAMPLE 15-85

2-{3,5-Dichloro-4-[4-hydroxy-3-(3-hydroxy-8-azabicyclo[3.2.1]octane-8-sulfonyl)-phenoxy]-phenyl}-2H-[1,2,4]triazine-3,5-dione MS Calc.:555.4; Found:552.9.

EXAMPLE 15-86

2-{3,5-Dichloro-4-[4-hydroxy-3-(3-oxo-8-azabicyclo[3.2.1]octane-8-sulfonyl)-phenoxy]-phenyl}-2H-[1,2,4]triazine-3,5-dione MS Calc.:553.4; Found:550.8.

EXAMPLE 15-87

2-[4-Chloro-7-hydroxy-6-(piperidine-1-sulfonyl)-9H-xanthen-2-yl]-2H-[1,2,4]triazine-3,5-dione MS Calc.:490.9; Found:490.9.

EXAMPLE 16

2-[3,5-Dichloro-4-(4-hydroxy-3-piperidin-1-ylmethyl-phenoxy)-phenyl]-2H-[1,2,4]triazine-3,5-dione

Step A

2-[3,5-Dichloro-4-(3-formyl-4-methoxy-phenoxy)-phenyl]-2H-[1,2,4]triazine-3,5-dione A solution of 2-[3,5-dichloro-4-(4-methoxy-phenoxy)-phenyl]-2H-[1,2,4]triazine-3,5-dione (1 g) and hexamethylenetetraamine (0.6 g) in trifluoroacetic acid (8 mL) was stirred at 70° C. for 18 h. The trifluoroacetic acid was removed in vacuo, water added and the resulting mixture was stirred for 30 min. The residue was extracted with ethyl acetate, the organic phase washed with water, brine, dried ($Na_2SO_4$), concentrated in vacuo and flash chromatographed on silica gel (35% acetone/hexanes) to afford the title compound of Step A as an off-white solid, 1.0 g (m.p. 184–187° C.).

Step B

2-[3,5-Dichloro-4-(3-formyl-4-hydroxy-phenoxy)-phenyl]-2H-[1,2,4]triazine-3,5-dione To a cooled (0° C.), stirred solution of 2-[3,5-dichloro-4-(3-formyl-4-methoxy-phenoxy)-phenyl]-2H-[1,2,4]triazine-3,5-dione (0.4 g) in dichloromethane (10 mL) was added 1M boron trichloride in dichloromethane (4 mL). The resulting orange slurry was stirred at ambient temperature for 5 h, ice added and the reaction stirred an additional 1 h. The two phase solution was diluted into ethyl acetate and washed with water, brine, dried ($Na_2SO_4$), concentrated in vacuo to afford the title compound of Step B as an off-white solid, 0.4 g (m.p. 146–150° C.).

Step C

2-[3,5-Dichloro-4-(4-hydroxy-3-piperidin-1-ylmethyl-phenoxy)-phenyl]-2H-[1,2,4]triazine-3,5-dione To a stirred solution of 2-[3,5-dichloro-4-(3-formyl-4-hydroxy-phenoxy)-phenyl]-2H-[1,2,4]triazine-3,5-dione (100 mg) in dichloromethane (3 mL) and dimethylformamide (0.5 mL) was added acetic acid (20 μL), piperidine (35 μL) and sodium triacetoxyborohydride (81 mg). After 6 h, the reaction was diluted into ethyl acetate, washed with saturated sodium bicarbonate, brine, dried ($Na_2SO_4$) and concentrated in vacuo to provide a solid mass. Trituration of the solids with ethyl acetate and methanol afforded the title compound of this EXAMPLE as a colorless solid, 73 mg (m.p. 15–217° C.). MS Calc.:463.3; Found:463.0.

Using the appropriate starting materials, EXAMPLES 16-1 to 16-35 were prepared in an analogous manner to that described in EXAMPLE 16.

EXAMPLE 16-1

2-{4-[3-(Benzylamino-methyl)-4-hydroxy-phenoxy]-3,5-dichloro-phenyl}-2H-[1,2,4]triazine-3,5-dione MS Calc.:485.3; Found:485.0.

EXAMPLE 16-2

2-[3,5-Dichloro-4-(4-hydroxy-3-phenylaminomethyl-phenoxy)-phenyl]-2H-[1,2,4]triazine-3,5-dione MS Calc.:471.3. Found:471.0.

EXAMPLE 16-3

N-{5-[2,6-Dichloro-4-(3,5-dioxo-4,5-dihydro-3H-[1,2,4]triazin-2-yl)-phenoxy]-2-hydroxy-benzyl}-N-phenyl-methanesulfonamide MS Calc.:549.4; Found:549.2.

EXAMPLE 16-4

2-[3,5-Dibromo-4-(4-hydroxy-3-phenylaminomethyl-phenoxy)-phenyl]-2H-[1,2,4]triazine-3,5-dione MS Calc.:560.2; Found:560.9.

EXAMPLE 16-5

2-(3,5-Dibromo-4-{3-[(4-fluoro-phenylamino)-methyl]-4-hydroxy-phenoxy}-phenyl)-2H-[1,2,4]triazine-3,5-dione MS Calc.:578.2; Found:578.9.

EXAMPLE 16-6

2-{3,5-Dichloro-4-[4-hydroxy-3-(o-tolylamino-methyl)-phenoxy]-phenyl}-2H-[1,2,4]triazine-3,5-dione MS Calc.:485.3; Found:484.9.

EXAMPLE 16-7

2-{4-[3-(Benzo[1,3]dioxol-5-ylaminomethyl)-4-hydroxy-phenoxy]-3,5-dichloro-phenyl}-2H-[1,2,4]triazine-3,5-dione MS Calc.:515.3; Found:514.9.

EXAMPLE 16-8

2-(3,5-Dichloro-4-{4-hydroxy-3-[(4-trifluoromethoxy-phenylamino)-methyl]-phenoxy}-phenyl)-2H-[1,2,4]triazine-3,5-dione MS Calc.:555.3; Found:554.9.

EXAMPLE 16-9

2-{3,5-Dichloro-4-[4-hydroxy-3-(p-tolylamino-methyl)-phenoxy]-phenyl}-2H-[1,2,4]triazine-3,5-dione MS Calc.:485.3; Found:485.0.

EXAMPLE 16-10

2-(3,5-Dichloro-4-{4-hydroxy-3-[(2-isopropyl-phenylamino)-methyl]-phenoxy}-phenyl)-2H-[1,2,4]triazine-3,5-dione MS Calc.:513.4; Found:513.1.

EXAMPLE 16-11

2-(4-{3-[(3-Bromo-phenylamino)-methyl]-4-hydroxy-phenoxy}-3,5-dichloro-phenyl)-2H-[1,2,4]triazine-3,5-dione MS Calc.:550.2; Found:548.9.

EXAMPLE 16-12

2-(3,5-Dichloro-4-{4-hydroxy-3-[(5,6,7,8-tetrahydro-naphthalen-1-ylamino)-methyl]-phenoxy}-phenyl)-2H-[1,2,4]triazine-3,5-dione MS Calc.:525.4; Found:523.1 (M−1).

EXAMPLE 16-13

2-{3,5-Dichloro-4-[4-hydroxy-3-(indan-5-ylaminomethyl)-phenoxy]-phenyl}-2H-[1,2,4]triazine-3,5-dione MS Calc.:511.4; Found:511.0.

EXAMPLE 16-14

2-(3,5-Dichloro-4-{3-[(4-fluoro-phenylamino)-methyl]-4-hydroxy-phenoxy}-phenyl)-2H-[1,2,4]triazine-3,5-dione MS Calc.:489.3; Found:489.0.

EXAMPLE 16-15

2-(3,5-Dichloro-4-{3-[(4-fluoro-2-methyl-phenylamino)-methyl]-4-hydroxy-phenoxy}-phenyl)-2H-[1,2,4]triazine-3,5-dione MS Calc.:503.3; Found:503.1.

EXAMPLE 16-16

2-(4-{3-[(3,5-Bis-trifluoromethyl-phenylamino)-methyl]-4-hydroxy-phenoxy}-3,5-dichloro-phenyl)-2H-[1,2,4]triazine-3,5-dione MS Calc.:607.3; Found:605.1.

EXAMPLE 16-17

2-(3,5-Dichloro-4-{4-hydroxy-3-[(1H-indazol-5-ylamino)-methyl]-phenoxy}-phenyl)-2H-[1,2,4]triazine-3,5-dione MS Calc.:511.3; Found:509.1.

EXAMPLE 16-18

2-(3,5-Dichloro-4-{4-hydroxy-3-[(1-methyl-1H-benzoimidazol-2-ylamino)-methyl]-phenoxy}-phenyl)-2H-[1,2,4]triazine-3,5-dione MS Calc.:525.4; Found:525.0.

EXAMPLE 16-19

2-(4-{3-[(5-tert-Butyl-2-methyl-2H-pyrazol-3-ylamino)-methyl]-4-hydroxy-phenoxy}-3,5-dichloro-phenyl)-2H-[1,2,4]triazine-3,5-dione MS Calc.:531.4; Found:529.1.

EXAMPLE 16-20

2-[3,5-Dichloro-4-(3-{[(4-chloro-phenyl)-methyl-amino]-methyl}-4-hydroxy-phenoxy)-phenyl]-2H-[1,2,4]triazine-3,5-dione MS Calc.:519.8; Found:519.0.

EXAMPLE 16-21

2-(3,5-Dichloro-4-{4-hydroxy-3-[(methyl-o-tolyl-amino)-methyl]-phenoxy}-phenyl)-2H-[1,2,4]triazine-3,5-dione MS Calc.:499.4; Found:499.1.

EXAMPLE 16-22

2-(3,5-Dichloro-4-{(4-hydroxy-3-[(methyl-phenyl-amino)-methyl]-phenoxy}-phenyl)-2H-[1,2,4]triazine-3,5-dione MS Calc.:485.3; Found:485.1.

EXAMPLE 16-23

2-[3,5-Dichloro-4-(4-hydroxy-3-{[(thiophen-2-ylmethyl)-amino]-methyl}-phenoxy)-phenyl]-2H-[1,2,4]triazine-3,5-dione MS Calc.:491.4; Found:490.8.

EXAMPLE 16-24

2-{3,5-Dichloro-4-[3-(3,3-dimethyl-piperidin-1-ylmethyl)-4-hydroxy-phenoxy]-phenyl}-2H-[1,2,4]triazine-3,5-dione MS Calc.:491.0; Found:491.2.

EXAMPLE 16-25

2-{3,5-Dichloro-4-[3-(3,4-dihydro-1H-isoquinolin-2-ylmethyl)-4-hydroxy-phenoxy]-phenyl}-2H-[1,2,4]triazine-3,5-dione MS Calc.:511; Found:511.

EXAMPLE 16-26

2-{3,5-Dichloro-4-[4-hydroxy-3-(3-methyl-3-phenyl-piperidin-1-ylmethyl)-phenoxy]-phenyl}-2H-[1,2,4]triazine-3,5-dione MS Calc.:555; Found:555.

EXAMPLE 16-27

2-{4-[3-(Bicyclo[2.2.1]hept-2-ylaminomethyl)-4-hydroxy-phenoxy]-3,5-dichloro-phenyl}-2H-[1,2,4]triazine-3,5-dione MS Calc.:489.4; Found:489.3.

EXAMPLE 16-28

2-[4-(3-Azepan-1-ylmethyl-4-hydroxy-phenoxy)-3,5-dichloro-phenyl]-2H-[1,2,4]triazine-3,5-dione MS Calc.:477.4; Found:477.3.

EXAMPLE 16-29

2-(3,5-Dichloro-4-{3-[(cyclohexylmethyl-amino)-methyl]-4-hydroxy-phenoxy}-phenyl)-2H-[1,2,4]triazine-3,5-dione MS Calc.:491.4; Found:491.3.

EXAMPLE 16-30

2-(3,5-Dichloro-4-{4-hydroxy-3-[(methyl-phenethyl-amino)-methyl]-phenoxy}-phenyl)-2H-[1,2,4]triazine-3,5-dione MS Calc.:513.4; Found:513.3.

EXAMPLE 16-31

2-(4-{3-[(Benzyl-methyl-amino)-methyl]-4-hydroxy-phenoxy}-3,5-dichloro-phenyl)-2H-[1,2,4]triazine-3,5-dione MS Calc.:499.4; Found:499.2.

EXAMPLE 16-32

2-{3,5-Dichloro-4-[3-(1,4-dioxa-8-aza-spiro[4.5]dec-8-ylmethyl)-4-hydroxy-phenoxy]-phenyl}-2H-[1,2,4]triazine-3,5-dione MS Calc.:521; Found:521.

EXAMPLE 16-33

2-(3,5-Dichloro-4-{4-hydroxy-3-[(1,7,7-trimethyl-bicyclo[2.2.1]hept-2-ylamino)-methyl]-phenoxy}-phenyl)-2H-[1,2,4]triazine-3,5-dione MS Calc.:531; Found:531.

EXAMPLE 16-34

2-{3,5-Dichloro-4-[3-(3,4-dihydro-2H-quinolin-1-ylmethyl)-4-hydroxy-phenoxy]-phenyl}-2H-[1,2,4]triazine-3,5-dione MS Calc.:511.4; Found:511.4.

EXAMPLE 16-35

2-{4-[3-(Bicyclo[2.2.1]hept-2-ylaminomethyl)-4-hydroxy-phenoxy]-3,5-dichloro-phenyl}-2H-[1,2,4]triazine-3,5-dione MS Calc.:489.4; Found:489.2.

EXAMPLE 17

2-{3,5-Dichloro-4-[3-(cis-3,5-dimethyl-piperidine-1-carbonyl)-4-hydroxy-phenoxy]-phenyl}-2H-[1,2,4]triazine-3,5-dione

Step A

2-[3,5-Dichloro-4-(3-carboxyl-4-methoxy-phenoxy)-phenyl]-2H-[1,2,4]triazine-3,5-dione A solution of 2-[3,5-dichloro-4-(3-formyl-4-methoxy-phenoxy)-phenyl]-2H-[1,2,4]triazine-3,5-dione (25 g) in THF (90 mL) was added to a solution of 2-methyl-2-butene (98 mL) in t-butanol (610 mL). Over a 10-min period, a solution of sodium chlorite (50 g) in 0.6 M aqueous potassium dihydrophosphate (715 mL) was added to produce a cloudy yellow solution. After 1 h, the reaction was diluted into ethyl acetate, layers separated and the aqueous layer extracted with ethyl acetate (2x). The combined organic layers were washed with brine, dried ($Na_2SO_4$), concentrated in vacuo and the resulting yellow oil flash chromatographed on silica gel (2-5% methanol/dichloromethane) to afford the title compound of Step A as an off-white foam, 21 g.

Step B

2-[3,5-Dichloro-4-(3-carboxyl-4-hydroxy-phenoxy)-phenyl]-2H-[1,2,4]triazine-3,5-dione To a cooled (−78° C.), stirred solution of 2-[3,5-dichloro-4-(3-carboxyl-4-methoxy-phenoxy)-phenyl]-2H-[1,2,4]triazine-3,5-dione (21 g) in dichloromethane (400 mL) was added a 1 M solution of boron trichloride in dichloromethane (150 mL). The reaction was allowed to stir at ambient temperature for 4 h, recooled (−78° C.), and quenched with 75% methanov/water. After 1 h at ambient temperature, the solvents were removed in vacuo, water azeotroped off with toluene and the resulting oil pumped under vacuum (~0.5 torr) for 24 h. The resulting foam was passed through a plug of silica gel (5–10% methanol/dichloromethane to afford the title compound of Step B as a tan foam, 16 g.

Step C

5-[2,6-Dichloro-4-(3,5-dioxo-4,5-dihydro-3H-[1,2,4]triazin-2-yl)-phenoxy]-2-hydroxy-benzoic acid 2,5-dioxo-pyrrolidin-1-yl ester To a cooled (0° C.), stirred solution of 2-[3,5-dichloro-4-(3-carboxyl-4-hydroxy-phenoxy)-phenyl]-2H-[1,2,4]triazine-3,5-dione (5 g) and N-hydroxysuccinimde (1.5 g) in dimethoxyethane (50 mL) was added dicyclohexylcarbodiimide (2.8 g). After 4 h, the reaction slurry was diluted with ethyl acetate, solids filtered and washed with additional portions of ethyl acetate and tetrahydrofuran. The residual filter cake (6.6 g) showed the title compound of Step C and ~0.4 equivalents of dicyclohexylurea. The material was utilized without further purification.

Step D

2-{3,5-Dichloro-4-[3-(cis-3,5-dimethyl-piperidine-1-carbonyl)-4-hydroxy-phenoxy]-phenyl}-2H-[1,2,4]triazine-3,5-dione To solution of 5-[2,6-dichloro-4-(3,5-dioxo-4,5-dihydro-3H-[1,2,4]triazin-2-yl)-phenoxy]-2-hydroxy-benzoic acid 2,5-dioxo-pyrrolidin-1-yl ester (320 mg) and triethylamine (265 μL) in dimethoxyethane (1.3 mL) was added 3,5-cis-dimethylpiperidine (189 mg). After 2 h, the reaction solution was concentrated in vacuo and flash chromatographed on silica gel (50% ethyl acetate/hexanes) to afford the title compound of this Example as a colorless solid, 130 mg. MS Calc.:505.3 Found:505.2.

Using the appropriate starting materials, EXAMPLES 17-1 to 17-113 were prepared in an analogous manner to that described in EXAMPLE 17.

EXAMPLE 17-1

2-{3,5-Dichloro-4-[4-hydroxy-3-(piperidine-1-carbonyl)-phenoxy]-phenyl}-2H-[1,2,4]triazine-3,5-dione MS Calc.:477.3; Found:477.0.

EXAMPLE 17-2

2-{3-Chloro-4-[4-hydroxy-3-(piperidine-1-carbonyl)-phenoxy]-5-methyl-phenyl}-2H-[1,2,4]triazine-3,5-dione MS Calc.:456.9; Found:457.2.

EXAMPLE 17-3

2-{3-Chloro-4-[4-hydroxy-3-(pyrrolidine-1-carbonyl)-phenoxy]-5-methyl-phenyl}-2H-[1,2,4]triazine-3,5-dione MS Calc.:443.8; Found:443.1.

EXAMPLE 17-4

5-[2-Chloro-4-(3,5-dioxo-4,5-dihydro-3H-[1,2,4]triazin-2-yl)-6-methyl-phenoxy]-N-cyclohexyl-2-hydroxy-benzamide MS Calc.:470.9; Found:471.2.

EXAMPLE 17-5

5-[2-Chloro-4-(3,5-dioxo-4,5-dihydro-3H-[1,2,4]triazin-2-yl)-6-methyl-phenoxy]-2-hydroxy-N-phenyl-benzamide MS Calc.:464.9; Found:465.1.

EXAMPLE 17-6

N-Cyclohexyl-5-[2,6-dichloro-4-(3,5-dioxo-4,5-dihydro-3H-[1,2,4]triazin-2-yl)-phenoxy]-N-ethyl-2-hydroxy-benzamide MS Calc.:519.4; Found:519.0.

EXAMPLE 17-7

2-{3,5-Dichloro-4-[4-hydroxy-3-(pyrrolidine-1-carbonyl)-phenoxy]-phenyl}-2H-[1,2,4]triazine-3,5-dione MS Calc.:463.3; Found:463.1.

EXAMPLE 17-8

2-{4-[3-(Azepane-1-carbonyl)-4-hydroxy-phenoxy]-3,5-dichloro-phenyl}-2H-[1,2,4]triazine-3,5-dione MS Calc.:491.3; Found:491.1.

EXAMPLE 17-9

2-{3,5-Dichloro-4-[4-hydroxy-3-(4-methyl-piperidine-1-carbonyl)-phenoxy]-phenyl}-2H-[1,2,4]triazine-3,5-dione MS Calc.:491.3; Found:491.1.

EXAMPLE 17-10

N-Cyclohexyl-5-[2,6-dichloro-4-(3,5-dioxo-4,5-dihydro-3H-[1,2,4]triazin-2-yl)-phenoxy]-2-hydroxy-benzamide MS Calc.:491.3; Found:491.1.

EXAMPLE 17-11

N-Cyclohexyl-5-[2,6-dibromo-4-(3,5-dioxo-4,5-dihydro-3H-[1,2,4]triazin-2-yl)-phenoxy]-2-hydroxy-benzamide MS Calc.:580.2; Found:579.0 (M−1).

EXAMPLE 17-12

2-{3,5-Dibromo-4-[4-hydroxy-3-(piperidine-1-carbonyl)-phenoxy]-phenyl}-2H-[1,2,4]triazine-3,5-dione MS Calc.:580.2; Found:581.1.

EXAMPLE 17-13

N-Benzyl-5-[2,6-dibromo-4-(3,5-dioxo-4,5-dihydro-3H-[1,2,4]triazin-2-yl)-phenoxy]-2-hydroxy-benzamide MS Calc.:588.2; Found:589.0.

EXAMPLE 17-14

5-[2,6-Dibromo-4-(3,5-dioxo-4,5-dihydro-3H-[1,2,4]triazin-2-yl)-phenoxy]-2-hydroxy-N-(1S-phenyl-ethyl)-benzamide MS Calc.:602.2; Found:603.0.

EXAMPLE 17-15

5-[2,6-Dibromo-4-(3,5-dioxo-4,5-dihydro-3H-[1,2,4]triazin-2-yl)-phenoxy]-2-hydroxy-N-(1R-phenyl-ethyl)-benzamide MS Calc.:602.2; Found:603.0.

EXAMPLE 17-16

5-[2,6-Dibromo-4-(3,5-dioxo-4,5-dihydro-3H-[1,2,4]triazin-2-yl)-phenoxy]-N-(1,2-dimethyl-propyl)-2-hydroxy-benzamide MS Calc.:568.2; Found:569.0.

EXAMPLE 17-17

5-[2,6-Dibromo-4-(3,5-dioxo-4,5-dihydro-3H-[1,2,4]triazin-2-yl)-phenoxy]-2-hydroxy-N-phenyl-benzamide MS Calc.:574.2; Found:575.0.

EXAMPLE 17-18

2-{3,5-Dichloro-4-[4-hydroxy-3-(1,3,3-trimethyl-6-aza-bicyclo[3.2.1]octane-6-carbonyl)-phenoxy]-phenyl}-2H-[1,2,4]triazine-3,5-dione MS Calc.:545.4; Found:545.2.

EXAMPLE 17-19

5-[2,6-Dibromo-4-(3,5-dioxo-4,5-dihydro-3H-[1,2,4]triazin-2-yl)-phenoxy]-N-(1,1-dimethyl-propyl)-2-hydroxy-benzamide MS Calc.:568.2; Found:569.0.

EXAMPLE 17-20

5-[2,6-Dichloro-4-(3,5-dioxo-4,5-dihydro-3H-[1,2,4]triazin-2-yl)-phenoxy]-N-furan-2-ylmethyl-2-hydroxy-benzamide MS Calc.:489.3; Found:487.1.

EXAMPLE 17-21

N-(2-Chloro-benzyl)-5-[2,6-dichloro-4-(3,5-dioxo-4,5-dihydro-3H-[1,2,4]triazin-2-yl)-phenoxy]-2-hydroxy-benzamide MS Calc.:533.8; Found:533.1.

EXAMPLE 17-22

N-Cyclobutyl-5-[2,6-dichloro-4-(3,5-dioxo-4,5-dihydro-3H-[1,2,4]triazin-2-yl)-phenoxy]-2-hydroxy-benzamide MS Calc.:463.2; Found:461.0.

EXAMPLE 17-23

5-[2,6-Dichloro-4-(3,5-dioxo-4,5-dihydro-3H-[1,2,4]triazin-2-yl)-phenoxy]-2-hydroxy-N-thiophen-2-ylmethyl-benzamide MS Calc.:505.4; Found:505.0.

EXAMPLE 17-24

N-Cyclohexylmethyl-5-[2,6-dichloro-4-(3,5-dioxo-4,5-dihydro-3H-[1,2,4]triazin-2-yl)-phenoxy]-2-hydroxy-benzamide MS Calc.:505.4; Found:505.1.

EXAMPLE 17-25

5-[2,6-Dichloro-4-(3,5-dioxo-4,5-dihydro-3H-[1,2,4]triazin-2-yl)-phenoxy]-2-hydroxy-N-(1-methyl-2-phenoxy-ethyl)-benzamide MS Calc.:543.4; Found:543.1.

EXAMPLE 17-26

5-[2,6-Dibromo-4-(3,5-dioxo-4,5-dihydro-3H-[1,2,4]triazin-2-yl)-phenoxy]-2-hydroxy-N-indan-1-yl-benzamide MS Calc.:614.3; Found:615.0.

EXAMPLE 17-27

N-Bicyclo[2.2.1]hept-2-yl-5-[2,6-dibromo-4-(3,5-dioxo-4,5-dihydro-3H-[1,2,4]triazin-2-yl)-phenoxy]-2-hydroxy-benzamide MS Calc.:592.3; Found:593.0.

EXAMPLE 17-28

N-Bicyclo[2.2.1]hept-2-yl-5-[2,6-dibromo-4-(3,5-dioxo-4,5-dihydro-3H-[1,2,4]triazin-2-yl)-phenoxy]-2-hydroxy-benzamide MS Calc.:592.3; Found:593.1.

EXAMPLE 17-29

5-[2,6-Dibromo-4-(3,5-dioxo-4,5-dihydro-3H-[1,2,4]triazin-2-yl)-phenoxy]-2-hydroxy-N-(2-methyl-cyclohexyl)-benzamide MS Calc.:594.3; Found:595.0.

EXAMPLE 17-30

N-Cyclopropyl-5-[2,6-dichloro-4-(3,5-dioxo-4,5-dihydro-3H-[1,2,4]triazin-2-yl)-phenoxy]-2-hydroxy-benzamide MS Calc.:449.3; Found:447.1.

EXAMPLE 17-31

5-[2,6-Dichloro-4-(3,5-dioxo-4,5-dihydro-3H-[1,2,4]triazin-2-yl)-phenoxy]-2-hydroxy-N-(4-methyl-cyclohexyl)-benzamide MS Calc.:505.4; Found:503.1.

EXAMPLE 17-32

N-Bicyclo[2.2.1]hept-2-yl-5-[2,6-dichloro-4-(3,5-dioxo-4,5-dihydro-3H-[1,2,4]triazin-2-yl)-phenoxy]-2-hydroxy-benzamide MS Calc.:503.4; Found:503.1.

EXAMPLE 17-33

2-{3,5-Dichloro-4-[4-hydroxy-3-(3,3,5-trimethyl-azepane-1-carbonyl)-phenoxy]-phenyl}-2H-[1,2,4]triazine-3,5-dione MS Calc.:533.5; Found:533.2.

EXAMPLE 17-34

5-[2,6-Dichloro-4-(3,5-dioxo-4,5-dihydro-3H-[1,2,4]triazin-2-yl)-phenoxy]-2-hydroxy-N-(1,2,3,4-tetrahydro-naphthalen-1-yl)-benzamide MS Calc.:539.4; Found:539.1.

EXAMPLE 17-35

N-(1-Cyclohexyl-ethyl)-5-[2,6-dichloro-4-(3,5-dioxo-4,5-dihydro-3H-[1,2,4]triazin-2-yl)-phenoxy]-2-hydroxy-benzamide MS Calc.:519.4; Found:519.1.

EXAMPLE 17-36

N-(1-Cyclohexyl-ethyl)-5-[2,6-dichloro-4-(3,5-dioxo-4,5-dihydro-3H-[1,2,4]triazin-2-yl)-phenoxy]-2-hydroxy-benzamide MS Calc.:519.4; Found:519.1.

EXAMPLE 17-37

2-{3,5-Dichloro-4-[3-(5-ethyl-2-methyl-piperidine-1-carbonyl)-4-hydroxy-phenoxy]-phenyl}-2H-[1,2,4]triazine-3,5-dione MS Calc.:519.4; Found:519.1.

EXAMPLE 17-38

2-{3,5-Dichloro-4-[4-hydroxy-3-(3-methyl-3-phenyl-piperidine-1-carbonyl)-phenoxy]-phenyl}-2H-[1,2,4]triazine-3,5-dione MS Calc.:567.4; Found:567.1.

EXAMPLE 17-39

2-{3,5-Dichloro-4-[3-(3,3-dimethyl-piperidine-1-carbonyl)-4-hydroxy-phenoxy]-phenyl}-2H-[1,2,4]triazine-3,5-dione MS Calc.:505.4; Found:505.1.

EXAMPLE 17-40

5-[2,6-Dichloro-4-(3,5-dioxo-4,5-dihydro-3H-[1,2,4]triazin-2-yl)-phenoxy]-2-hydroxy-N-(2-phenyl-propyl)-benzamide MS Calc.:527.4; Found:527.0.

EXAMPLE 17-41

5-[2,6-Dichloro-4-(3,5-dioxo-4,5-dihydro-3H-[1,2,4]triazin-2-yl)-phenoxy]-2-hydroxy-N-(2-phenyl-cyclopropyl)-benzamide MS Calc.:525.3; Found:525.0.

EXAMPLE 17-42

N-Chroman-4-ylmethyl-5-[2,6-dichloro-4-(3,5-dioxo-4,5-dihydro-3H-[1,2,4]triazin-2-yl)-phenoxy]-2-hydroxy-N-methyl-benzamide MS Calc.:569.4; Found:569.0.

EXAMPLE 17-43

5-[2,6-Dibromo-4-(3,5-dioxo-4,5-dihydro-3H-[1,2,4]triazin-2-yl)-phenoxy]-2-hydroxy-N-indan-2-yl-benzamide MS Calc.:614.3; Found:615.0.

EXAMPLE 17-44

N-Benzyl-5-[2,6-dichloro-4-(3,5-dioxo-4,5-dihydro-3H-[1,2,4]triazin-2-yl)-phenoxy]-2-hydroxy-N-methyl-benzamide MS Calc.:513.4; Found:513.1.

EXAMPLE 17-45

N-Bicyclo[2.2.1]hept-2-yl-5-[2,6-dichloro-4-(3,5-dioxo-4,5-dihydro-3H-[1,2,4]triazin-2-yl)-phenoxy]-2-hydroxy-benzamide MS Calc.:503.5; Found:503.0.

EXAMPLE 17-46

5-[2,6-Dichloro-4-(3,5-dioxo-4,5-dihydro-3H-[1,2,4]triazin-2-yl)-phenoxy]-2-hydroxy-N-(1,7,7-trimethyl-bicyclo[2.2.1]hept-2-yl)-benzamide MS Calc.:545.4; Found:545.2.

EXAMPLE 17-47

5-[2,6-Dichloro-4-(3,5-dioxo-4,5-dihydro-3H-[1,2,4]triazin-2-yl)-phenoxy]-2-hydroxy-N-(1H-indol-4-ylmethyl)-benzamide MS Calc.:538.4; Found:536.0.

EXAMPLE 17-48

2-{3,5-Dichloro-4-[4-hydroxy-3-(1,2,3,4-tetrahydro-1,4-epiazano-naphthalene-9-carbonyl)-phenoxy]-phenyl}-2H-[1,2,4]triazine-3,5-dione MS Calc.:537.4; Found:537.0.

EXAMPLE 17-49

5-[2,6-Dichloro-4-(3,5-dioxo-4,5-dihydro-3H-[1,2,4]triazin-2-yl)-phenoxy]-2-hydroxy-N-methyl-N-pyridin-3-ylmethyl-benzamide MS Calc.:514.4; Found:514.1.

EXAMPLE 17-50

2-{3,5-Dichloro-4-[4-hydroxy-3-(4-phenyl-piperidine-1-carbonyl)-phenoxy]-phenyl}-2H-[1,2,4]triazine-3,5-dione MS Calc.:553.4; Found:553.0.

EXAMPLE 17-51

5-[2,6-Dichloro-4-(3,5-dioxo-4,5-dihydro-3H-[1,2,4]triazin-2-yl)-phenoxy]-2-hydroxy-N-(2-hydroxy-1-phenyl-ethyl)-benzamide MS Calc.:529.4; Found:529.0.

EXAMPLE 17-52

N-(6-Chloro-pyridin-3-yl)-5-[2,6-dichloro-4-(3,5-dioxo-4,5-dihydro-3H-[1,2,4]triazin-2-yl)-phenoxy]-2-hydroxy-benzamide MS Calc.:520.8; Found:520.5.

EXAMPLE 17-53

2-{3,5-Dichloro-4-[3-(2,3-dimethyl-2,3-dihydro-indole-1-carbonyl)-4-hydroxy-phenoxy]-phenyl}-2H-[1,2,4]triazine-3,5-dione MS Calc.:539.4; Found:539.1.

EXAMPLE 17-54

5-[2,6-Dichloro-4-(3,5-dioxo-4,5-dihydro-3H-[1,2,4]triazin-2-yl)-phenoxy]-N-(1,2-diphenyl-ethyl)-2-hydroxy-benzamide MS Calc.:589.4; Found:589.1.

EXAMPLE 17-55

5-[2,6-Dichloro-4-(3,5-dioxo-4,5-dihydro-3H-[1,2,4]triazin-2-yl)-phenoxy]-2-hydroxy-N-phenethyl-benzamide MS Calc.:513.4; Found:513.1.

EXAMPLE 17-56

2-{3,5-Dichloro-4-[3-(2,3-dihydro-indole-1-carbonyl)-4-hydroxy-phenoxy]-phenyl}-2H-[1,2,4]triazine-3,5-dione MS Calc.:511.3; Found:511.0.

EXAMPLE 17-57

5-[2,6-Dichloro-4-(3,5-dioxo-4,5-dihydro-3H-[1,2,4]triazin-2-yl)-phenoxy]-N-(2,2-diphenyl-ethyl)-2-hydroxy-benzamide MS Calc.:589.4; Found:589.1.

EXAMPLE 17-58

2-{3,5-Dichloro-4-[4-hydroxy-3-(2-methyl-2,3-dihydro-indole-1-carbonyl)-phenoxy]-phenyl}-2H-[1,2,4]triazine-3,5-dione MS Calc.:525.4; Found:525.1.

EXAMPLE 17-59

5-[2,6-Dichloro-4-(3,5-dioxo-4,5-dihydro-3H-[1,2,4] triazin-2-yl)-phenoxy]-N-[2-(2,4-dichloro-phenyl)-ethyl]-2-hydroxy-benzamide MS Calc.:582.2; Found:583.0.

EXAMPLE 17-60

5-[2,6-Dichloro-4-(3,5-dioxo-4,5-dihydro-3H-[1,2,4] triazin-2-yl)-phenoxy]-N-[2-(4-fluoro-phenyl)-ethyl]-2-hydroxy-benzamide MS Calc.:531.3; Found:531.1.

EXAMPLE 17-61

N-[2-(4-Chloro-phenyl)-1-methyl-ethyl]-5-[2,6-dichloro-4-(3,5-dioxo-4,5-dihydro-3H-[1,2,4]triazin-2-yl)-phenoxy]-2-hydroxy-benzamide MS Calc.:561.8; Found:561.1.

EXAMPLE 17-62

2-{3,5-Dichloro-4-[4-hydroxy-3-(3-methyl-3-phenyl-pyrrolidine-1-carbonyl)-phenoxy]-phenyl}-2H-[1,2,4]triazine-3,5-dione MS Calc.:553.4; Found:551.2.

EXAMPLE 17-63

2-{3,5-Dichloro-4-[4-hydroxy-3-(3-phenyl-piperidine-1-carbonyl)-phenoxy]-phenyl}-2H-[1,2,4]triazine-3,5-dione MS Calc.:553.4; Found:553.0.

EXAMPLE 17-64

2-{3,5-Dichloro-4-[3-(3-cyclohexyl-piperidine-1-carbonyl)-4-hydroxy-phenoxy]-phenyl}-2H-[1,2,4]triazine-3,5-dione MS Calc.:559.4; Found:559.0.

EXAMPLE 17-65

2-{4-[3-(2-Benzyl-piperidine-1-carbonyl)-4-hydroxy-phenoxy]-3,5-dichloro-phenyl}-2H-[1,2,4]triazine-3,5-dione MS Calc.:567.4; Found:567.0.

EXAMPLE 17-66

2-{3,5-Dichloro-4-[3-(3,4-dihydro-1H-isoquinoline-2-carbonyl)-4-hydroxy-phenoxy]-phenyl}-2H-[1,2,4]triazine-3,5-dione MS Calc.:525.4; Found:525.0.

EXAMPLE 17-67

5-[2,6-Dichloro-4-(3,5-dioxo-4,5-dihydro-3H-[1,2,4] triazin-2-yl)-phenoxy]-2-hydroxy-N-methyl-N-phenethyl-benzamide MS Calc.:527.4; Found:526.9.

EXAMPLE 17-68

N-[2-(4-Chloro-phenyl)-1-methyl-ethyl]-5-[2,6-dichloro-4-(3,5-dioxo-4,5-dihydro-3H-[1,2,4]triazin-2-yl)-phenoxy]-2-hydroxy-N-methyl-benzamide MS Calc.:575.8; Found:574.9.

EXAMPLE 17-69

5-[2,6-Dichloro-4-(3,5-dioxo-4,5-dihydro-3H-[1,2,4] triazin-2-yl)-phenoxy]-2-hydroxy-N-(1,1a,6,6a-tetrahydro-cyclopropa[a]inden-1-yl)-benzamide MS Calc.:537.4; Found:535.1.

EXAMPLE 17-70

5-[2,6-Dichloro-4-(3,5-dioxo-4,5-dihydro-3H-[1,2,4] triazin-2-yl)-phenoxy]-2-hydroxy-N-(1,2,3,4-tetrahydro-naphthalen-2-yl)-benzamide MS Calc.:539.4; Found:538.9.

EXAMPLE 17-71

N-(1-Benzyl-cyclopentyl)-5-[2,6-dichloro-4-(3,5-dioxo-4,5-dihydro-3H-[1,2,4]triazin-2-yl)-phenoxy]-2-hydroxy-N-methyl-benzamide MS Calc.:581.5; Found:580.9.

EXAMPLE 17-72

N-(1-Benzyl-cyclohexyl)-5-[2,6-dichloro-4-(3,5-dioxo-4,5-dihydro-3H-[1,2,4]triazin-2-yl)-phenoxy]-2-hydroxy-N-methyl-benzamide MS Calc.:595.5; Found:594.9.

EXAMPLE 17-73

2-{3,5-Dichloro-4-[3-(3,4-dihydro-2H-quinoline-1-carbonyl)-4-hydroxy-phenoxy]-phenyl}-2H-[1,2,4] triazine-3,5-dione MS Calc.:525.4; Found:525.2.

EXAMPLE 17-74

2-{3,5-Dichloro-4-[4-hydroxy-3-(3R-methyl-3-phenyl-piperidine-1-carbonyl)-phenoxy]-phenyl}-2H-[1,2,4]triazine-3,5-dione MS Calc.:567.5; Found:567.3.

EXAMPLE 17-75

2-{3,5-Dichloro-4-[4-hydroxy-3-(3S-methyl-3-phenyl-piperidine-1-carbonyl)-phenoxy]-phenyl}-2H-[1,2,4]triazine-3,5-dione MS Calc.:567.5; Found:567.1.

EXAMPLE 17-76

2-{3,5-Dichloro-4-[4-hydroxy-3-(2,3-dihydro-spiro-[1H-indene-1,3'-piperidine]-1-carbonyl)-phenoxy]-phenyl}-2H-[1,2,4]triazine-3,5-dione MS Calc.:579.4; Found:579.1.

EXAMPLE 17-77

2-{3,5-Dichloro-4-[3-(2,3,4,4a,9,9a-hexahydro-indeno[2,1-b]pyridine-1-carbonyl)-4-hydroxy-phenoxy]-phenyl}-2H-[1,2,4]triazine-3,5-dione MS Calc.:565.4; Found:565.2.

EXAMPLE 17-78

2-{3,5-Dichloro-4-[3-(3-cyclohexyl-3-methyl-piperidine-1-carbonyl)-4-hydroxy-phenoxy]-phenyl}-2H-[1,2,4]triazine-3,5-dione MS Calc.:573.5; Found:573.1.

EXAMPLE 17-79

2-{3,5-Dichloro-4-[4-hydroxy-3-(1-p-tolyl-3-aza-bicyclo[3.1.0]hexane-3-carbonyl)-phenoxy]-phenyl}-2H-[1,2,4]triazine-3,5-dione MS Calc.:565.4; Found:565.1.

EXAMPLE 17-80

5-[2,6-Dichloro-4-(3,5-dioxo-4,5-dihydro-3H-[1,2,4]triazin-2-yl)-phenoxy]-2-hydroxy-N-methyl-N-(1,2,3,4-tetrahydro-naphthalen-1-ylmethyl)-benzamide MS Calc.:567.4; Found:567.3.

EXAMPLE 17-81

5-[2,6-Dichloro-4-(3,5-dioxo-4,5-dihydro-3H-[1,2,4]triazin-2-yl)-phenoxy]-2-hydroxy-N-methyl-N-[1-methyl-2-(6,7,8,9-tetrahydro-5H-benzocyclohepten-2-yl)-ethyl]-benzamide MS Calc.:609.6; Found:609.3.

EXAMPLE 17-82

5-[2,6-Dichloro-4-(3,5-dioxo-4,5-dihydro-3H-[1,2,4]triazin-2-yl)-phenoxy]-2-hydroxy-N-(1,7,7-trimethyl-bicyclo[2.2.1]hept-2-yl)-benzamide MS Calc.:545.5; Found:545.3.

EXAMPLE 17-83

2-{4-[3-(11-Aza-tricyclo[7.3.1.0$^{2,7}$]trideca-2(7),3,5-triene-11-carbonyl)-4-hydroxy-phenoxy]-3,5-dichloro-phenyl}-2H-[1,2,4]triazine-3,5-dione MS Calc.:565.4; Found:565.1.

EXAMPLE 17-84

2-{3,5-Dichloro-4-[3-(3,3-diphenyl-piperidine-1-carbonyl)-4-hydroxy-phenoxy]-phenyl}-2H-[1,2,4]triazine-3,5-dione MS Calc.:629.5; Found:629.1.

EXAMPLE 17-85

2-{3,5-Dichloro-4-[3-[1,3-dihydro-spiro(1H-indene-1,3'-piperidine)-1-carbonyl)-4-hydroxy-phenoxy]-phenyl}-2H-[1,2,4]triazine-3,5-dione MS Calc.:565.4; Found:565.1.

EXAMPLE 17-86

2-{3,5-Dichloro-4-[4-hydroxy-3-(3-methyl-3,4-dihydro-1H-isoquinoline-2-carbonyl)-phenoxy]-phenyl}-2H-[1,2,4]triazine-3,5-dione MS Calc.:539.4; Found:539.1.

EXAMPLE 17-87

2-{3,5-Dichloro-4-[3-(7,8-dimethoxy-3,4-dihydro-1H-isoquinoline-2-carbonyl)-4-hydroxy-phenoxy]-phenyl}-2H-[1,2,4]triazine-3,5-dione MS Calc.:585.4; Found:585.1.

EXAMPLE 17-88

2-{4-[3-(7-Bromo-3,4-dihydro-1H-isoquinoline-2-carbonyl)-4-hydroxy-phenoxy]-3,5-dichloro-phenyl}-2H-[1,2,4]triazine-3,5-dione MS Calc.:604.2; Found:605.2.

EXAMPLE 17-89

2-{3,5-Dichloro-4-[4-hydroxy-3-(8-methoxy-3,4-dihydro-1H-isoquinoline-2-carbonyl)-phenoxy]-phenyl}-2H-[1,2,4]triazine-3,5-dione MS Calc.:555.4; Found:555.3.

EXAMPLE 17-90

2-{3,5-Dichloro-4-[3-(6,7-dimethoxy-3,4-dihydro-1H-isoquinoline-2-carbonyl)-4-hydroxy-phenoxy]-phenyl}-2H-[1,2,4]triazine-3,5-dione MS Calc.:585.4; Found:585.3.

EXAMPLE 17-91

2-{3,5-Dichloro-4-[4-hydroxy-3-(3-hydroxymethyl-3,4-dihydro-1H-isoquinoline-2-carbonyl)-phenoxy]-phenyl}-2H-[1,2,4]triazine-3,5-dione MS Calc.:555.4; Found:555.3.

EXAMPLE 17-92

5-[2,6-Dichloro-4-(3,5-dioxo-4,5-dihydro-3H-[1,2,4]triazin-2-yl)-phenoxy]-2-hydroxy-N-(2,6,6-trimethyl-bicyclo[3.1.1]hept-3-yl)-benzamide MS Calc.:545.4; Found:544.9.

EXAMPLE 17-93

5-[2,6-Dichloro-4-(3,5-dioxo-4,5-dihydro-3H-[1,2,4]triazin-2-yl)-phenoxy]-2-hydroxy-N-(1-hydroxymethyl-cyclopentyl)-benzamide MS Calc.:507.3; Found:506.9.

EXAMPLE 17-94

2-{3,5-Dichloro-4-[3-(4,4-dimethyl-3,4-dihydro-1H-isoquinoline-2-carbonyl)-4-hydroxy-phenoxy]-phenyl}-2H-[1,2,4]triazine-3,5-dione MS Calc.:553.4; Found:552.9.

EXAMPLE 17-95

2-{3,5-Dichloro-4-[4-hydroxy-3-(4-methoxy-3,4-dihydro-1H-isoquinoline-2-carbonyl)-phenoxy]-phenyl}-2H-[1,2,4]triazine-3,5-dione MS Calc.:555.3; Found:554.9.

EXAMPLE 17-96

2-{3,5-Dichloro-4-[3-(8,8-dimethyl-9-oxa-2-aza-spiro[5.5]undecane-2-carbonyl)-4-hydroxy-phenoxy]-phenyl}-2H-[1,2,4]triazine-3,5-dione MS Calc.:575.4; Found:574.9.

EXAMPLE 17-97

2-{3,5-Dichloro-4-[3-(8-chloro-3,4-dihydro-1H-isoquinoline-2-carbonyl)-4-hydroxy-phenoxy]-phenyl}-2H-[1,2,4]triazine-3,5-dione MS Calc.:559.8; Found:558.8.

EXAMPLE 17-98

2-{3,5-Dichloro-4-[4-hydroxy-3-(4-methyl-3,4-dihydro-1H-isoquinoline-2-carbonyl)-phenoxy]-phenyl}-2H-[1,2,4]triazine-3,5-dione MS Calc.:539.4; Found:538.9.

EXAMPLE 17-99

5-[2,6-Dichloro-4-(3,5-dioxo-4,5-dihydro-3H-[1,2,4]
triazin-2-yl)-phenoxy]-2-hydroxy-N-(3,3,5,5-
tetramethyl-cyclohexyl)-benzamide MS Calc.:547.4; Found:546.9.

EXAMPLE 17-100

2-{3,5-Dichloro-4-[4-hydroxy-3-(2S-hydroxy-7-aza-
spiro[4.5]decane-7-carbonyl)-phenoxy]-phenyl}-2H-
[1,2,4]triazine-3,5-dione MS Calc.:547.4; Found:547.1.

EXAMPLE 17-101

2-{3,5-Dichloro-4-[4-hydroxy-3-(2R-hydroxy-7-aza-
spiro[4.5]decane-7-carbonyl)-phenoxy]-phenyl}-2H-
[1,2,4]triazine-3,5-dione MS Calc.:547.4; Found:547.1.

EXAMPLE 17-102

5-[2,6-Dichloro-4-(3,5-dioxo-4,5-dihydro-3H-[1,2,4]
triazin-2-yl)-phenoxy]-N-(6,6-dimethyl-bicyclo
[3.1.1]hept-2R-(1a,2b,5a)-yl)-2-hydroxy-benzamide MS Calc.:531.4; Found:531.1.

EXAMPLE 17-103

5-[2,6-Dichloro-4-(3,5-dioxo-4,5-dihydro-3H-[1,2,4]
triazin-2-yl)-phenoxy]-N-(spiro(8-azabicyclo[3.2.1]
octane-3,2'-1,3]dioxolane))-2-hydroxy-benzamide MS Calc.:561.4; Found:560.9.

EXAMPLE 17-104

2-{3,5-Dichloro-4-[4-hydroxy-3-(3-oxo-8-aza-
bicyclo[3.2.1]octane-8-carbonyl)-phenoxy]-phenyl}-
2H-[1,2,4]triazine-3,5-dione MS Calc.:517.3; Found:516.9.

EXAMPLE 17-105

2-{3,5-Dichloro-4-[4-hydroxy-3-(morpholine-4-
carbonyl)-phenoxy]-phenyl}-2H-[1,2,4]triazine-3,5-
dione MS Calc.:479.3; Found:478.8.

EXAMPLE 17-106

5-[2,6-Dichloro-4-(3,5-dioxo-4,5-dihydro-3H-[1,2,4]
triazin-2-yl)-phenoxy]-2-hydroxy-N-(2R-hydroxy-
(R)-cyclohexyl)-benzamide MS Calc.:507.8; Found:507.0.

EXAMPLE 17-107

5-[2,6-Dichloro-4-(3,5-dioxo-4,5-dihydro-3H-[1,2,4]
triazin-2-yl)-phenoxy]-2-hydroxy-N-(2R-hydroxy-
(S)-cyclopentyl)-benzamide MS Calc.:493.3; Found:493.0.

EXAMPLE 17-108

5-[2,6-Dichloro-4-(3,5-dioxo-4,5-dihydro-3H-[1,2,4]
triazin-2-yl)-phenoxy]-2-hydroxy-N-(spiro(8-
azabicyclo[3.2.1]octane-3-endo,2'(3'H)-furan))-
benzamide MS Calc.:559.4; Found:559.0.

EXAMPLE 17-109

2-{3,5-Dichloro-4-[3-(2S,6R-dimethyl-morpholine-
4-carbonyl)-4-hydroxy-phenoxy]-phenyl}-2H-[1,2,
4]triazine-3,5-dione MS Calc.:507.3; Found:505.1.

EXAMPLE 17-110

5-[2,6-Dichloro-4-(3,5-dioxo-4,5-dihydro-3H-[1,2,4]
triazin-2-yl)-phenoxy]-2-hydroxy-N-(2-hydroxy-1,1-
dimethyl-ethyl)-benzamide MS Calc.:481.3; Found:481.1.

EXAMPLE 17-111

5-[2,6-Dichloro-4-(3,5-dioxo-4,5-dihydro-3H-[1,2,4]
triazin-2-yl)-phenoxy]-2-hydroxy-N-(2-
hydroxymethyl-bicyclo[2.2.1]hept-2-yl)-benzamide MS Calc.:533.4; Found:533.1.

EXAMPLE 17-112

5-[2,6-Dichloro-4-(3,5-dioxo-4,5-dihydro-3H-[1,2,4]
triazin-2-yl)-phenoxy]-2-hydroxy-N-(1-
hydroxymethyl-cyclohexyl)-benzamide MS Calc.:521.4; Found:521.2.

EXAMPLE 17-113

2-{3,5-Dichloro-4-[4-hydroxy-3-(3-hydroxymethyl-
3-methyl-morpholine-4-carbonyl)-phenoxy]-
phenyl}-2H-[1,2,4]triazine-3,5-dione MS Calc.:523.3; Found:522.9.

EXAMPLE 18

2-[4-(3-Bromo-4-hydroxy-phenoxy)-3,5-dimethyl-
phenyl]-3,5-dioxo-2,3,4,5-tetrahydro-[1,2,4]triazine-
6-carboxylic acid benzylamide

Step A

2-[4-(3-Bromo-4-methoxy-phenoxy)-3,5-dimethyl-
phenyl]-3,5-dioxo-2,3,4,5-tetrahydro-[1,2,4]triazine-
6-carboxylic acid benzylamide To a solution of benzylamine (6 µmol) in 10% DMF/DCE were added sequentially 10% DMF/DCE solutions of 2-[4-(3-bromo-4-methoxy-phenoxy)-3,5-dimethyl-phenyl]-3,5-dioxo-2,3,4,5-tetrahydro-[1,2,4]triazine-6-carboxylic acid (5 µmol) and N-methylmorpholine (6 µmol). A DMF solution of O-benzotriazol-1-yl-N,N,N',N'-tetramethyluronium hexafluorophosphate (7.5 µmol) and the resulting solution was shaken for 4 h at room temperature. The reaction was concentrated at 60° C. in a vacuum oven overnight. HPLC and LCMS shows complete conversion to the title compound of Step A. MS Calc.: 550.1; Found: 549.0 (M−1).

Step B

2-[4-(3-Bromo-4-hydroxy-phenoxy)-3,5-dimethyl-
phenyl]-3,5-dioxo-2,3,4,5-tetrahydro-[1,2,4]triazine-
6-carboxylic acid benzylamide Cleavage of the methyl ether was accomplished using procedures analogous to those detailed above, such as Step C of EXAMPLE 12, to afford the title compound of this EXAMPLE. MS Calc.: 536.1; Found: 535.0 (M−1).

Using the appropriate starting materials, EXAMPLES 18-1 to 18-147 were prepared in an analogous manner to that described in EXAMPLE 18.

EXAMPLE 18-1

2-[4-(3-Bromo-4-methoxy-phenoxy)-3,5-dimethyl-phenyl]-3,5-dioxo-2,3,4,5-tetrahydro-[1,2,4]triazine-6-carboxylic acid sec-butylamide MS Calc.: 516.1; Found: 514.9 (M−1).

EXAMPLE 18-2

2-[4-(3-Bromo-4-methoxy-phenoxy)-3,5-dimethyl-phenyl]-3,5-dioxo-2,3,4,5-tetrahydro-[1,2,4]triazine-6-carboxylic acid (4-methyl-cyclohexyl)-amide MS Calc.: 556.1; Found: 555.1 (M−1).

EXAMPLE 18-3

2-[4-(3-Bromo-4-methoxy-phenoxy)-3,5-dimethyl-phenyl]-3,5-dioxo-2,3,4,5-tetrahydro-[1,2,4]triazine-6-carboxylic acid (4-phenyl-butyl)-amide MS Calc.: 592.1; Found: 591.1 (M−1).

EXAMPLE 18-4

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-hydroxy-propyl)-amide MS Calc.: 518.1; Found: 516.8 (M−1).

EXAMPLE 18-5

2-[4-(3-Bromo-4-methoxy-phenoxy)-3,5-dimethyl-phenyl]-3,5-dioxo-2,3,4,5-tetrahydro-[1,2,4]triazine-6-carboxylic acid cyclohexylamide MS Calc.: 542.1; Found: 541.0 (M−1).

EXAMPLE 18-6

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(2-hydroxy-ethoxy)-ethyl]-amide MS Calc.: 548.1; Found: 553.8 (M+1).

EXAMPLE 18-7

2-[4-(3-Bromo-4-methoxy-phenoxy)-3,5-dimethyl-phenyl]-3,5-dioxo-2,3,4,5-tetrahydro-[1,2,4]triazine-6-carboxylic acid (pyrimidin-2-ylmethyl)-amide MS Calc.: 552.1; Found: 549.9 (M−1).

EXAMPLE 18-8

-[4-(3-Bromo-4-methoxy-phenoxy)-3,5-dimethyl-phenyl]-3,5-dioxo-2,3,4,5-tetrahydro-[1,2,4]triazine-6-carboxylic acid (3-piperidin-1-yl-propyl)-amide MS Calc.: 585.2; Found: 584.1 (M−1).

EXAMPLE 18-9

2-[4-(3-Bromo-4-methoxy-phenoxy)-3,5-dimethyl-phenyl]-3,5-dioxo-2,3,4,5-tetrahydro-[1,2,4]triazine-6-carboxylic acid butylamide MS Calc.: 516.1; Found: 514.9 (M−1).

EXAMPLE 18-10

2-[4-(3-Bromo-4-methoxy-phenoxy)-3,5-dimethyl-phenyl]-3,5-dioxo-2,3,4,5-tetrahydro-[1,2,4]triazine-6-carboxylic acid undecylamide MS Calc.: 614.2; Found: 613.2 (M−1).

EXAMPLE 18-11

2-[4-(3-Bromo-4-methoxy-phenoxy)-3,5-dimethyl-phenyl]-3,5-dioxo-2,3,4,5-tetrahydro-[1,2,4]triazine-6-carboxylic acid (furan-2-ylmethyl)-amide MS Calc.: 540.1; Found: 538.9 (M−1).

EXAMPLE 18-12

2-[4-(3-Bromo-4-methoxy-phenoxy)-3,5-dimethyl-phenyl]-3,5-dioxo-2,3,4,5-tetrahydro-[1,2,4]triazine-6-carboxylic acid (4-cyano-cyclohexylmethyl)-amide MS Calc.: 581.1; Found: 580.1 (M−1).

EXAMPLE 18-13

2-[4-(3-Bromo-4-methoxy-phenoxy)-3,5-dimethyl-phenyl]-3,5-dioxo-2,3,4,5-tetrahydro-[1,2,4]triazine-6-carboxylic acid [3-(4-methyl-piperazin-1-yl)-propyl]-amide MS Calc.: 600.2; Found: 599.1 (M−1).

EXAMPLE 18-14

2-[4-(3-Bromo-4-methoxy-phenoxy)-3,5-dimethyl-phenyl]-3,5-dioxo-2,3,4,5-tetrahydro-[1,2,4]triazine-6-carboxylic acid (tetrahydro-furan-2-ylmethyl)-amide MS Calc.: 544.1; Found: 543.0 (M−1).

EXAMPLE 18-15

2-[4-(3-Bromo-4-methoxy-phenoxy)-3,5-dimethyl-phenyl]-3,5-dioxo-2,3,4,5-tetrahydro-[1,2,4]triazine-6-carboxylic acid allylamide MS Calc.: 500.1; Found: 498.9 (M−1).

EXAMPLE 18-16

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-morpholin-4-yl-ethyl)-amide MS Calc.: 573.1; Found: 571.9 (M−1).

EXAMPLE 18-17

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-cyclohex-1-enyl-ethyl)-amide MS Calc.: 568.1; Found: 566.9 (M−1).

EXAMPLE 18-18

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-hydroxy-2-(4-hydroxy-3-methoxy-phenyl)-ethyl]-amide MS Calc.: 626.1; Found: 624.9 (M−1).

EXAMPLE 18-19

2-[4-(3-Bromo-4-methoxy-phenoxy)-3,5-dimethyl-phenyl]-3,5-dioxo-2,3,4,5-tetrahydro-[1,2,4]triazine-6-carboxylic acid (3-oxo-isoxazolidin-4-yl)-amide MS Calc.: 545.1; Found: 543.9 (M−1).

EXAMPLE 18-20

2-[4-(3-Bromo-4-methoxy-phenoxy)-3,5-dimethyl-phenyl]-3,5-dioxo-2,3,4,5-tetrahydro-[1,2,4]triazine-6-carboxylic acid (3,3-diphenyl-propyl)-amide MS Calc.: 654.1; Found: 653.1 (M−1).

EXAMPLE 18-21

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-methoxy-1-methyl-ethyl)-amide MS Calc.: 532.1; Found: 530.8 (M−1).

EXAMPLE 18-22

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-oxo-2-phenyl-ethyl)-amide MS Calc.: 578.1; Found: 576.8 (M−1).

EXAMPLE 18-23

2-[4-(3-Bromo-4-methoxy-phenoxy)-3,5-dimethyl-phenyl]-3,5-dioxo-2,3,4,5-tetrahydro-[1,2,4]triazine-6-carboxylic acid (pyridin-2-ylmethyl)-amide MS Calc.: 551.1; Found: 549.9 (M−1).

EXAMPLE 18-24

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(1H-indol-3-yl)-ethyl]-amide MS Calc.: 603.1; Found: 602.1 (M−1).

EXAMPLE 18-25

2-[4-(3-Bromo-4-methoxy-phenoxy)-3,5-dimethyl-phenyl]-3,5-dioxo-2,3,4,5-tetrahydro-[1,2,4]triazine-6-carboxylic acid (1-aza-bicyclo[2.2.2]oct-3-yl)-amide MS Calc.: 569.1; Found: 568.1 (M−1).

EXAMPLE 18-26

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(2-isopropyl-5-methyl-phenoxy)-ethyl]-amide MS Calc.: 636.2; Found: 635.1 (M−1).

EXAMPLE 18-27

2-[4-(3-Bromo-4-methoxy-phenoxy)-3,5-dimethyl-phenyl]-3,5-dioxo-2,3,4,5-tetrahydro-[1,2,4]triazine-6-carboxylic acid (pyridin-4-ylmethyl)-amide MS Calc.: 551.1; Found: 550.0 (M−1).

EXAMPLE 18-28

2-[4-(3-Bromo-4-methoxy-phenoxy)-3,5-dimethyl-phenyl]-3,5-dioxo-2,3,4,5-tetrahydro-[1,2,4]triazine-6-carboxylic acid (thiophen-2-ylmethyl)-amide MS Calc.: 556.0; Found: 554.9 (M−1).

EXAMPLE 18-29

2-[4-(3-Bromo-4-methoxy-phenoxy)-3,5-dimethyl-phenyl]-3,5-dioxo-2,3,4,5-tetrahydro-[1,2,4]triazine-6-carboxylic acid (1-hydroxymethyl-3-methylsulfanyl-propyl)-amide MS Calc.: 578.1; Found: 577.0 (M−1).

EXAMPLE 18-30

({2-[4-(3-Bromo-4-methoxy-phenoxy)-3,5-dimethyl-phenyl]-3,5-dioxo-2,3,4,5-tetrahydro-[1,2,4]triazine-6-carbonyl}-amino)-acetic acid methyl ester MS Calc.: 518; Found: 517 (M−1).

EXAMPLE 18-31

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(3,4-bis-benzyloxy-phenyl)-ethyl]-amide MS Calc.: 776.2; Found: 775.1 (M−1).

EXAMPLE 18-32

2-[4-(3-Bromo-4-methoxy-phenoxy)-3,5-dimethyl-phenyl]-3,5-dioxo-2,3,4,5-tetrahydro-[1,2,4]triazine-6-carboxylic acid thiochroman-4-ylamide MS Calc.: 608.1; Found: 606.9 (M−1).

EXAMPLE 18-33

2-[4-(3-Bromo-4-methoxy-phenoxy)-3,5-dimethyl-phenyl]-6-(piperidine-1-carbonyl)-2H-[1,2,4]triazine-3,5-dione MS Calc.: 528.1; Found: 526.9 (M−1).

EXAMPLE 18-34

2-[4-(3-Bromo-4-methoxy-phenoxy)-3,5-dimethyl-phenyl]-3,5-dioxo-2,3,4,5-tetrahydro-[1,2,4]triazine-6-carboxylic acid (5-cyano-pentyl)-amide MS Calc.: 555.1; Found: 553.9 (M−1).

EXAMPLE 18-35

2-[4-(3-Bromo-4-methoxy-phenoxy)-3,5-dimethyl-phenyl]-3,5-dioxo-2,3,4,5-tetrahydro-[1,2,4]triazine-6-carboxylic acid prop-2-ynylamide MS Calc.: 498.1; Found: 496.9 (M−1).

EXAMPLE 18-36

2-[4-(3-Bromo-4-methoxy-phenoxy)-3,5-dimethyl-phenyl]-3,5-dioxo-2,3,4,5-tetrahydro-[1,2,4]triazine-6-carboxylic acid (1,1-dioxo-tetrahydro-1H-thiophen-3-yl)-amide MS Calc.: 578.0; Found: 576.9 (M−1).

EXAMPLE 18-37

2-[4-(3-Bromo-4-methoxy-phenoxy)-3,5-dimethyl-phenyl]-6-(morpholine-4-carbonyl)-2H-[1,2,4]triazine-3,5-dione MS Calc.: 530.1; Found: 528.9 (M−1).

EXAMPLE 18-38

2-[4-(3-Bromo-4-methoxy-phenoxy)-3,5-dimethyl-phenyl]-6-(thiazolidine-3-carbonyl)-2H-[1,2,4]triazine-3,5-dione MS Calc.: 532.0; Found: 530.8 (M−1).

EXAMPLE 18-39

[2-({2-[4-(3-Bromo-4-methoxy-phenoxy)-3,5-dimethyl-phenyl]-3,5-dioxo-2,3,4,5-tetrahydro-[1,2,4]triazine-6-carbonyl}-amino)-thiazol-4-yl]-acetic acid ethyl ester MS Calc.: 629.1; Found: 627.9 (M−1).

EXAMPLE 18-40

2-[4-(3-Bromo-4-methoxy-phenoxy)-3,5-dimethyl-phenyl]-3,5-dioxo-2,3,4,5-tetrahydro-[1,2,4]triazine-6-carboxylic acid (5-methyl-thiazol-2-yl)-amide MS Calc.: 557.0; Found: 555.9 (M−1).

EXAMPLE 18-41

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-ethyl-2H-pyrazol-3-yl)-amide MS Calc.: 554.1; Found: 552.8 (M−1).

EXAMPLE 18-42

(4-{2-[4-(3-Bromo-4-methoxy-phenoxy)-3,5-dimethyl-phenyl]-3,5-dioxo-2,3,4,5-tetrahydro-[1,2,4]triazine-6-carbonyl}-piperazin-1-yl)-acetic acid ethyl ester MS Calc.: 615.1; Found: 614.1 (M−1).

EXAMPLE 18-43

2-[4-(3-Bromo-4-methoxy-phenoxy)-3,5-dimethyl-phenyl]-6-(3,4-dihydro-1H-isoquinoline-2-carbonyl)-2H-[1,2,4]triazine-3,5-dione MS Calc.: 576.1; Found: 574.8 (M−1).

EXAMPLE 18-44

6-(3-Aza-bicyclo[3.2.2]nonane-3-carbonyl)-2-[4-(3-bromo-4-methoxy-phenoxy)-3,5-dimethyl-phenyl]-2H-[1,2,4]triazine-3,5-dione MS Calc.: 568.1; Found: 566.9 (M−1).

EXAMPLE 18-45

1-{2-[4-(3-Bromo-4-methoxy-phenoxy)-3,5-dimethyl-phenyl]-3,5-dioxo-2,3,4,5-tetrahydro-[1,2,4]triazine-6-carbonyl}-piperidine-3-carboxylic acid amide MS Calc.: 571.1; Found: 569.9 (M−1).

EXAMPLE 18-46

2-[4-(3-Bromo-4-methoxy-phenoxy)-3,5-dimethyl-phenyl]-3,5-dioxo-2,3,4,5-tetrahydro-[1,2,4]triazine-6-carboxylic acid (6,6-dimethyl-bicyclo[3.1.1]hept-2-ylmethyl)-amide MS Calc.: 596.2; Found: 595.1 (M−1).

EXAMPLE 18-47

2-[4-(3-Bromo-4-methoxy-phenoxy)-3,5-dimethyl-phenyl]-6-(octahydro-isoquinoline-2-carbonyl)-2H-[1,2,4]triazine-3,5-dione MS Calc.: 582.1; Found: 581.0 (M−1).

EXAMPLE 18-48

2-[4-(3-Bromo-4-methoxy-phenoxy)-3,5-dimethyl-phenyl]-6-(1,3,3-trimethyl-6-aza-bicyclo[3.2.1]octane-6-carbonyl)-2H-[1,2,4]triazine-3,5-dione MS Calc.: 596.2; Found: 595.0 (M−1).

EXAMPLE 18-49

2-[4-(3-Bromo-4-methoxy-phenoxy)-3,5-dimethyl-phenyl]-3,5-dioxo-2,3,4,5-tetrahydro-[1,2,4]triazine-6-carboxylic acid bicyclo[2.2.1]hept-2-ylamide MS Calc.: 554.1; Found: 552.9 (M−1).

EXAMPLE 18-50

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2-dimethylamino-ethyl)-amide MS Calc.: 531.1; Found: 529.8 (M−1).

EXAMPLE 18-51

2-[4-(3-Bromo-4-methoxy-phenoxy)-3,5-dimethyl-phenyl]-3,5-dioxo-2,3,4,5-tetrahydro-[1,2,4]triazine-6-carboxylic acid (3-imidazol-1-yl-propyl)-amide MS Calc.: 568.1; Found: 566.8 (M−1).

EXAMPLE 18-52

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(1-methyl-1H-pyrrol-2-yl)-ethyl]-amide MS Calc.: 567.1; Found: 565.9 (M−1).

EXAMPLE 18-53

2-[4-(3-Bromo-4-methoxy-phenoxy)-3,5-dimethyl-phenyl]-6-(4-pyridin-2-yl-piperazine-1-carbonyl)-2H-[1,2,4]triazine-3,5-dione MS Calc.: 606.1; Found: 605.1 (M−1).

EXAMPLE 18-54

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,5-dimethoxy-benzylamide MS Calc.: 610.1; Found: 609.1 (M−1).

EXAMPLE 18-55

2-[4-(3-Bromo-4-methoxy-phenoxy)-3,5-dimethyl-phenyl]-3,5-dioxo-2,3,4,5-tetrahydro-[1,2,4]triazine-6-carboxylic acid [3-(2-methoxy-ethoxy)-propyl]-amide MS Calc.: 576.1; Found: 575.0 (M−1).

EXAMPLE 18-56

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(4-sulfamoyl-phenyl)-ethyl]-amide MS Calc.: 643.1; Found: 641.9 (M−1).

EXAMPLE 18-57

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(3,4,5-trihydroxy-phenyl)-ethyl]-amide MS Calc.: 612.1; Found: 613.0 (M+1).

EXAMPLE 18-58

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(5-bromo-2-methoxy-phenyl)-ethyl]-amide MS Calc.: 672.0; Found: 670.9 (M−1).

EXAMPLE 18-59

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(4-ethoxy-3-methoxy-phenyl)-ethyl]-amide MS Calc.: 638.1; Found: 637.0 (M−1).

EXAMPLE 18-60

2-[4-(3-Bromo-4-methoxy-phenoxy)-3,5-dimethyl-phenyl]-3,5-dioxo-2,3,4,5-tetrahydro-[1,2,4]triazine-6-carboxylic acid [2-(4-fluoro-phenyl)-ethyl]-amide MS Calc.: 582.1; Found: 581.0 (M−1).

EXAMPLE 18-61

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-trifluoromethoxy-benzylamide MS Calc.: 634.1; Found: 633.0 (M−1).

EXAMPLE 18-62

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4-trifluoromethyl-benzylamide MS Calc.: 618.1; Found: 617.0 (M−1).

EXAMPLE 18-63

2-[4-(3-Bromo-4-methoxy-phenoxy)-3,5-dimethyl-phenyl]-3,5-dioxo-2,3,4,5-tetrahydro-[1,2,4]triazine-6-carboxylic acid (benzo[1,3]dioxol-5-ylmethyl)-amide MS Calc.: 594.1; Found: 593.0 (M−1).

EXAMPLE 18-64

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4-dimethylamino-benzylamide MS Calc.: 593.1; Found: 592.0 (M−1).

EXAMPLE 18-65

2-[4-(3-Bromo-4-methoxy-phenoxy)-3,5-dimethyl-phenyl]-3,5-dioxo-2,3,4,5-tetrahydro-[1,2,4]triazine-6-carboxylic acid (2,5,9-trimethyl-7-oxo-7H-furo[3,2-g]chromen-4-ylmethyl)-amide MS Calc.: 700.1; Found: 699.1 (M−1).

EXAMPLE 18-66

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(2-hydroxymethyl-phenylsulfanyl)-benzylamide MS Calc.: 688.1; Found: 686.8 (M−1).

EXAMPLE 18-67

1-{2-[4-(3-Bromo-4-methoxy-phenoxy)-3,5-dimethyl-phenyl]-3,5-dioxo-2,3,4,5-tetrahydro-[1,2,4]triazine-6-carbonyl}-piperidine-4-carboxylic acid amide MS Calc.: 571.1; Found: 570.0 (M−1).

EXAMPLE 18-68

2-[4-(3-Bromo-4-methoxy-phenoxy)-3,5-dimethyl-phenyl]-6-(4-methyl-piperidine-1-carbonyl)-2H-[1,2,4]triazine-3,5-dione MS Calc.: 542.1; Found: 540.9 (M−1).

EXAMPLE 18-69

2-[4-(3-Bromo-4-methoxy-phenoxy)-3,5-dimethyl-phenyl]-6-(4-{3-[1-(2-hydroxy-ethyl)-piperidin-4-yl]-propyl}-piperidine-1-carbonyl)-2H-[1,2,4]triazine-3,5-dione MS Calc.: 697.2; Found: 696.2 (M−1).

EXAMPLE 18-70

1-{2-[4-(3-Bromo-4-methoxy-phenoxy)-3,5-dimethyl-phenyl]-3,5-dioxo-2,3,4,5-tetrahydro-[1,2,4]triazine-6-carbonyl}-piperidine-3-carboxylic acid diethylamide MS Calc.: 627.2; Found: 626.2 (M−1).

EXAMPLE 18-71

2-[4-(3-Bromo-4-methoxy-phenoxy)-3,5-dimethyl-phenyl]-6-[4-phenyl-4-(pyrrolidine-1-carbonyl)-piperidine-1-carbonyl]-2H-[1,2,4]triazine-3,5-dione MS Calc.: 701.2; Found: 700.0 (M−1).

EXAMPLE 18-72

2-[4-(3-Bromo-4-methoxy-phenoxy)-3,5-dimethyl-phenyl]-6-(4-oxo-1-phenyl-1,3,8-triaza-spiro[4.5]decane-8-carbonyl)-2H-[1,2,4]triazine-3,5-dione MS Calc.: 674.1; Found: 673.0 (M−1).

EXAMPLE 18-73

1-{2-[4-(3-Bromo-4-methoxy-phenoxy)-3,5-dimethyl-phenyl]-3,5-dioxo-2,3,4,5-tetrahydro-[1,2,4]triazine-6-carbonyl}-4-oxo-piperidine-3-carboxylic acid methyl ester MS Calc.: 600.1; Found: 598.9 (M−1).

EXAMPLE 18-74

2-[4-(3-Bromo-4-methoxy-phenoxy)-3,5-dimethyl-phenyl]-6-{4-[(4-chloro-phenyl)-phenyl-methyl]-piperazine-1-carbonyl}-2H-[1,2,4]triazine-3,5-dione MS Calc.: 729.1; Found: 727.9 (M−1).

EXAMPLE 18-75

2-[4-(3-Bromo-4-methoxy-phenoxy)-3,5-dimethyl-phenyl]-6-[4-(3-hydroxy-propyl)-piperazine-1-carbonyl]-2H-[1,2,4]triazine-3,5-dione MS Calc.: 587.1; Found: 586.1 (M−1).

EXAMPLE 18-76

4-{2-[4-(3-Bromo-4-methoxy-phenoxy)-3,5-dimethyl-phenyl]-3,5-dioxo-2,3,4,5-tetrahydro-[1,2,4]triazine-6-carbonyl}-piperazine-1-carboxylic acid tert-butyl ester MS Calc.: 629.1; Found: 628.0 (M−1).

EXAMPLE 18-77

2-[4-(3-Bromo-4-methoxy-phenoxy)-3,5-dimethyl-phenyl]-6-(4-phenyl-piperazine-1-carbonyl)-2H-[1,2,4]triazine-3,5-dione MS Calc.: 605.1; Found: 604.1 (M−1).

EXAMPLE 18-78

6-[4-(4-Acetyl-phenyl)-piperazine-1-carbonyl]-2-[4-(3-bromo-4-methoxy-phenoxy)-3,5-dimethyl-phenyl]-2H-[1,2,4]triazine-3,5-dione MS Calc.: 647.1; Found: 646.0 (M−1).

EXAMPLE 18-79

2-[4-(3-Bromo-4-methoxy-phenoxy)-3,5-dimethyl-phenyl]-6-[4-(3-chloro-phenyl)-piperazine-1-carbonyl]-2H-[1,2,4]triazine-3,5-dione MS Calc.: 639.1; Found: 638.0 (M−1).

EXAMPLE 18-80

2-[4-(3-Bromo-4-methoxy-phenoxy)-3,5-dimethyl-phenyl]-6-(4-phenethyl-piperazine-1-carbonyl)-2H-[1,2,4]triazine-3,5-dione MS Calc.: 633.2; Found: 632.1 (M−1).

EXAMPLE 18-81

2-[4-(3-Bromo-4-methoxy-phenoxy)-3,5-dimethyl-phenyl]-6-(4-naphthalen-1-yl-piperazine-1-carbonyl)-2H-[1,2,4]triazine-3,5-dione MS Calc.: 655.1; Found: 654.1 (M−1).

EXAMPLE 18-82

2-[4-(3-Bromo-4-methoxy-phenoxy)-3,5-dimethyl-phenyl]-6-[4-(4-fluoro-phenyl)-piperazine-1-carbonyl]-2H-[1,2,4]triazine-3,5-dione MS Calc.: 623.1; Found: 622.1 (M−1).

EXAMPLE 18-83

2-[4-(3-Bromo-4-methoxy-phenoxy)-3,5-dimethyl-phenyl]-6-[4-(2-trifluoromethyl-benzyl)-piperazine-1-carbonyl]-2H-[1,2,4]triazine-3,5-dione MS Calc.: 687.1; Found: 685.8 (M−1).

EXAMPLE 18-83A

2-[4-(3-Bromo-4-hydroxy-phenoxy)-3,5-dimethyl-phenyl]-3,5-dioxo-2,3,4,5-tetrahydro-[1,2,4]triazine-6-carboxylic acid benzylamide MS Calc.: 536.1; Found: 537.0 (M+1).

EXAMPLE 18-84

2-[4-(3-Bromo-4-hydroxy-phenoxy)-3,5-dimethyl-phenyl]-3,5-dioxo-2,3,4,5-tetrahydro-[1,2,4]triazine-6-carboxylic acid sec-butylamide MS Calc.: 502.1; Found: 501.1 (M−1).

EXAMPLE 18-85

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (4-methyl-cyclohexyl)-amide MS Calc.: 542.1; Found: 541.1 (M−1).

EXAMPLE 18-86

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (4-phenyl-butyl)-amide MS Calc.: 578.1; Found: 577.1 (M−1).

EXAMPLE 18-87

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-hydroxy-propyl)-amide MS Calc.: 504.1; Found: 502.9 (M−1).

EXAMPLE 18-88

2-[4-(3-Bromo-4-hydroxy-phenoxy)-3,5-dimethyl-phenyl]-3,5-dioxo-2,3,4,5-tetrahydro-[1,2,4]triazine-6-carboxylic acid cyclohexylamide MS Calc.: 528.1; Found: 527.0 (M−1).

EXAMPLE 18-89

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [2-(2-hydroxy-ethoxy)-ethyl]-amide MS Calc.: 534.1; Found: 533.2 (M−1).

EXAMPLE 18-90

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (pyrimidin-2-ylmethyl)-amide MS Calc.: 538.1; Found: 534.1 (M−1).

EXAMPLE 18-91

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (3-piperidin-1-yl-propyl)-amide MS Calc.: 571.1; Found: 570.1 (M−1).

EXAMPLE 18-92

2-[4-(3-Bromo-4-hydroxy-phenoxy)-3,5-dimethyl-phenyl]-3,5-dioxo-2,3,4,5-tetrahydro-[1,2,4]triazine-6-carboxylic acid butylamide MS Calc.: 502.1; Found: 501.0 (M−1).

EXAMPLE 18-93

2-[4-(3-Bromo-4-hydroxy-phenoxy)-3,5-dimethyl-phenyl]-3,5-dioxo-2,3,4,5-tetrahydro-[1,2,4]triazine-6-carboxylic acid undecylamide MS Calc.: 600.2; Found: 599.2 (M−1).

EXAMPLE 18-94

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (furan-2-ylmethyl)-amide MS Calc.: 526.0; Found: 525.1 (M−1).

EXAMPLE 18-95

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (4-cyano-cyclohexylmethyl)-amide MS Calc.: 567.1; Found: 566.1 (M−1).

EXAMPLE 18-96

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [3-(4-methyl-piperazin-1-yl)-propyl]-amide MS Calc.: 586.2; Found: 585.1 (M−1).

EXAMPLE 18-97

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (tetrahydro-furan-2-ylmethyl)-amide MS Calc.: 530.1; Found: 529.0 (M−1).

EXAMPLE 18-98

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-morpholin-4-yl-ethyl)-amide MS Calc.: 559.1; Found: 559.9 (M−1).

EXAMPLE 18-99

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-cyclohex-1-enyl-ethyl)-amide MS Calc.: 554.1; Found: 554.2.

EXAMPLE 18-100

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (3,3-diphenyl-propyl)-amide MS Calc.: 640.1; Found: 639.1 (M−1).

EXAMPLE 18-101

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-oxo-2-phenyl-ethyl)-amide MS Calc.: 564.1; Found: 565.5 (M+1).

EXAMPLE 18-102

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (pyridin-2-ylmethyl)-amide MS Calc.: 537.1; Found: 535.9 (M−1).

EXAMPLE 18-103

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (pyridin-4-ylmethyl)-amide MS Calc.: 537.1; Found: 536.2 (M−1).

EXAMPLE 18-104

({2-[4-(3-Bromo-4-hydroxy-phenoxy)-3,5-dimethyl-phenyl]-3,5-dioxo-2,3,4,5-tetrahydro-[1,2,4]triazine-6-carbonyl}-amino)-acetic acid methyl ester MS Calc.: 518.0; Found: 517.0 (M−1).

EXAMPLE 18-105

2-[4-(3-Bromo-4-hydroxy-phenoxy)-3,5-dimethyl-phenyl]-6-(piperidine-1-carbonyl)-2H-[1,2,4]triazine-3,5-dione MS Calc.: 514.1; Found: 513.1 (M−1).

EXAMPLE 18-106

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (5-cyano-pentyl)-amide MS Calc.: 541.1; Found: 540.1 (M−1).

EXAMPLE 18-107

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (1,1-dioxo-tetrahydro-1&-thiophen-3-yl)-amide MS Calc.: 564.0; Found: 563.0 (M−1).

EXAMPLE 18-108

2-[4-(3-Bromo-4-hydroxy-phenoxy)-3,5-dimethyl-phenyl]-6-(morpholine-4-carbonyl)-2H-[1,2,4]triazine-3,5-dione MS Calc.: 516.1; Found: 515.0 (M−1).

EXAMPLE 18-109

2-[4-(3-Bromo-4-hydroxy-phenoxy)-3,5-dimethyl-phenyl]-6-(thiazolidine-3-carbonyl)-2H-[1,2,4]triazine-3,5-dione MS Calc.: 518.0; Found: 517.1 (M−1).

EXAMPLE 18-110

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-ethyl-2H-pyrazol-3-yl)-amide MS Calc.: 540.1; Found: 539.0 (M−1).

EXAMPLE 18-111

2-[4-(3-Bromo-4-hydroxy-phenoxy)-3,5-dimethyl-phenyl]-6-(3,4-dihydro-1H-isoquinoline-2-carbonyl)-2H-[1,2,4]triazine-3,5-dione MS Calc.: 562.1; Found: 561.1 (M−1).

EXAMPLE 18-112

6-(3-Aza-bicyclo[3.2.2]nonane-3-carbonyl)-2-[4-(3-bromo-4-hydroxy-phenoxy)-3,5-dimethyl-phenyl]-2H-[1,2,4]triazine-3,5-dione MS Calc.: 554.1; Found: 553.1 (M−1).

EXAMPLE 18-113

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (6,6-dimethyl-bicyclo[3.1.1]hept-2-ylmethyl)-amide MS Calc.: 582.1; Found: 581.1 (M−1).

EXAMPLE 18-114

2-[4-(3-Bromo-4-hydroxy-phenoxy)-3,5-dimethyl-phenyl]-6-(octahydro-isoquinoline-2-carbonyl)-2H-[1,2,4]triazine-3,5-dione MS Calc.: 568.1; Found: 569.0 (M+1).

EXAMPLE 18-115

2-[4-(3-Bromo-4-hydroxy-phenoxy)-3,5-dimethyl-phenyl]-6-(1,3,3-trimethyl-6-aza-bicyclo[3.2.1]octane-6-carbonyl)-2H-[1,2,4]triazine-3,5-dione MS Calc.: 582.1; Found: 581.1 (M−1).

EXAMPLE 18-116

2-[4-(3-Bromo-4-hydroxy-phenoxy)-3,5-dimethyl-phenyl]-3,5-dioxo-2,3,4,5-tetrahydro-[1,2,4]triazine-6-carboxylic acid bicyclo[2.2.1]hept-2-ylamide MS Calc.: 540.1; Found: 539.1 (M−1).

EXAMPLE 18-117

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (2-dimethylamino-ethyl)-amide MS Calc.: 517.1; Found: 516.1 (M−1).

EXAMPLE 18-118

2-[4-(3-Bromo-4-hydroxy-phenoxy)-3,5-dimethyl-phenyl]-3,5-dioxo-2,3,4,5-tetrahydro-[1,2,4]triazine-6-carboxylic acid (3-imidazol-1-yl-propyl)-amide MS Calc.: 554.1; Found: 553.0 (M−1).

EXAMPLE 18-119

2-[4-(3-Bromo-4-hydroxy-phenoxy)-3,5-dimethyl-phenyl]-3,5-dioxo-2,3,4,5-tetrahydro-[1,2,4]triazine-6-carboxylic acid 3,5-dimethoxy-benzylamide MS Calc.: 596.1; Found: 595.3 (M−1).

EXAMPLE 18-120

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [3-(2-methoxy-ethoxy)-propyl]-amide MS Calc.: 562.1; Found: 502.9 (M-CH$_2$CH$_2$OCH$_3$).

EXAMPLE 18-121

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [2-(3,4,5-trihydroxy-phenyl)-ethyl]-amide MS Calc.: 598.1; Found: 473 (M-C$_6$H$_5$O$_3$).

EXAMPLE 18-122

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [2-(5-bromo-2-methoxy-phenyl)-ethyl]-amide MS Calc.: 658.0; Found: 643.0 (M-CH$_3$).

EXAMPLE 18-123

2-[4-(3-Bromo-4-hydroxy-phenoxy)-3,5-dimethyl-phenyl]-3,5-dioxo-2,3,4,5-tetrahydro-[1,2,4]triazine-6-carboxylic acid [2-(4-fluoro-phenyl)-ethyl]-amide MS Calc.: 568.1; Found: 567.0 (M−1).

EXAMPLE 18-124

2-[4-(3-Bromo-4-hydroxy-phenoxy)-3,5-dimethyl-phenyl]-3,5-dioxo-2,3,4,5-tetrahydro-[1,2,4]triazine-6-carboxylic acid 3-trifluoromethoxy-benzylamide MS Calc.: 620.1; Found: 618.8 (M−1).

EXAMPLE 18-125

2-[4-(3-Bromo-4-hydroxy-phenoxy)-3,5-dimethyl-phenyl]-3,5-dioxo-2,3,4,5-tetrahydro-[1,2,4]triazine-6-carboxylic acid 4-trifluoromethyl-benzylamide MS Calc.: 604.1; Found: 602.9 (M−1).

EXAMPLE 18-126

1-{2-[4-(3-Bromo-4-hydroxy-phenoxy)-3,5-dimethyl-phenyl]-3,5-dioxo-2,3,4,5-tetrahydro-[1,2,4]triazine-6-carbonyl}-piperidine-4-carboxylic acid amide MS Calc.: 557.1; Found: 569.0.

EXAMPLE 18-127

2-[4-(3-Bromo-4-hydroxy-phenoxy)-3,5-dimethyl-phenyl]-6-(4-methyl-piperidine-1-carbonyl)-2H-[1,2,4]triazine-3,5-dione MS Calc.: 528.1; Found: 527.0 (M−1).

EXAMPLE 18-128

2-[4-(3-Bromo-4-hydroxy-phenoxy)-3,5-dimethyl-phenyl]-6-(4-{3-[1-(2-hydroxy-ethyl)-piperidin-4-yl]-propyl}-piperidine-1-carbonyl)-2H-[1,2,4]triazine-3,5-dione MS Calc.: 683.2; Found: 682.3 (M−1).

EXAMPLE 18-129

1-{2-[4-(3-Bromo-4-hydroxy-phenoxy)-3,5-dimethyl-phenyl]-3,5-dioxo-2,3,4,5-tetrahydro-[1,2,4]triazine-6-carbonyl}-piperidine-3-carboxylic acid diethylamide MS Calc.: 613.2; Found: 612.2 (M−1).

EXAMPLE 18-130

2-[4-(3-Bromo-4-hydroxy-phenoxy)-3,5-dimethyl-phenyl]-6-[4-phenyl-4-(pyrrolidine-1-carbonyl)-piperidine-1-carbonyl]-2H-[1,2,4]triazine-3,5-dione MS Calc.: 687.2; Found: 685.1 (M−1).

EXAMPLE 18-131

2-[4-(3-Bromo-4-hydroxy-phenoxy)-3,5-dimethyl-phenyl]-6-(4-phenyl-piperazine-1-carbonyl)-2H-[1,2,4]triazine-3,5-dione MS Calc.: 591.1; Found: 591.5 (M+1).

EXAMPLE 18-132

2-[4-(3-Bromo-4-hydroxy-phenoxy)-3,5-dimethyl-phenyl]-6-(4-phenethyl-piperazine-1-carbonyl)-2H-[1,2,4]triazine-3,5-dione MS Calc.: 619.1; Found: 618.1 (M−1).

EXAMPLE 18-133

2-[4-(3-Bromo-4-hydroxy-phenoxy)-3,5-dimethyl-phenyl]-6-[4-(3-chloro-propyl)-piperazine-1-carbonyl]-2H-[1,2,4]triazine-3,5-dione MS Calc.: 591.1; Found: 591.7 (M+1).

EXAMPLE 18-134

2-[4-(3-Bromo-4-hydroxy-phenoxy)-3,5-dimethyl-phenyl]-6-[4-(4-fluoro-phenyl)-piperazine-1-carbonyl]-2H-[1,2,4]triazine-3,5-dione MS Calc.: 609.1; Found: 609.7 (M+1).

EXAMPLE 18-135

2-[4-(3-Bromo-4-hydroxy-phenoxy)-3,5-dimethyl-phenyl]-6-[4-(2-trifluoromethyl-benzyl)-piperazine-1-carbonyl]-2H-[1,2,4]triazine-3,5-dione MS Calc.: 673.1; Found: 672.0 (M−1).

EXAMPLE 18-136

1-{2-[4-(3-Bromo-4-hydroxy-phenoxy)-3,5-dimethyl-phenyl]-3,5-dioxo-2,3,4,5-tetrahydro-[1,2,4]triazine-6-carbonyl}-piperidine-3-carboxylic acid amide MS Calc.: 557.1; Found: 556.2 (M−1).

EXAMPLE 18-137

1-{2-[4-(3-Bromo-4-hydroxy-phenoxy)-3,5-dimethyl-phenyl]-3,5-dioxo-2,3,4,5-tetrahydro-[1,2,4]triazine-6-carbonyl}-4-oxo-piperidine-3-carboxylic acid methyl ester MS Calc.: 586.1; Found: 585.2 (M−1).

EXAMPLE 18-138

6-(4-Acetyl-piperazine-1-carbonyl)-2-[4-(3-bromo-4-hydroxy-phenoxy)-3,5-dimethyl-phenyl]-2H-[1,2,4]triazine-3,5-dione MS Calc.: 557.1; Found: 556.2 (M−1).

EXAMPLE 18-139

2-[4-(3-Bromo-4-hydroxy-phenoxy)-3,5-dimethyl-phenyl]-6-(4-methyl-piperazine-1-carbonyl)-2H-[1,2,4]triazine-3,5-dione MS Calc.: 529.1; Found: 528.2 (M−1).

EXAMPLE 18-140

2-[4-(3-Bromo-4-hydroxy-phenoxy)-3,5-dimethyl-phenyl]-6-(4-ethyl-3-hydroxy-piperazine-1-carbonyl)-2H-[1,2,4]triazine-3,5-dione MS Calc.: 559.1; Found: 558.2 (M−1).

EXAMPLE 18-141

2-(4-{2-[4-(3-Bromo-4-hydroxy-phenoxy)-3,5-dimethyl-phenyl]-3,5-dioxo-2,3,4,5-tetrahydro-[1,2,4]triazine-6-carbonyl}-piperazin-1-yl)-N-isopropyl-acetamide MS Calc.: 614.1; Found: 613.2 (M−1).

EXAMPLE 18-142

2-[4-(3-Bromo-4-hydroxy-phenoxy)-3,5-dimethyl-phenyl]-6-[4-(2-oxo-2-pyrrolidin-1-yl-ethyl)-piperazine-1-carbonyl]-2H-[1,2,4]triazine-3,5-dione MS Calc.: 626.1; Found: 625.2 (M−1).

EXAMPLE 18-143

2-[4-(3-Bromo-4-hydroxy-phenoxy)-3,5-dimethyl-phenyl]-6-[4-(3-phenyl-allyl)-piperazine-1-carbonyl]-2H-[1,2,4]triazine-3,5-dione MS Calc.: 631.1; Found: 630.2 (M−1).

EXAMPLE 18-144

2-[4-(3-Bromo-4-hydroxy-phenoxy)-3,5-dimethyl-phenyl]-6-[4-(2-morpholin-4-yl-2-oxo-ethyl)-piperazine-1-carbonyl]-2H-[1,2,4]triazine-3,5-dione MS Calc.: 642.1; Found: 641.2 (M−1).

EXAMPLE 18-145

6-{4-[Bis-(4-fluoro-phenyl)-methyl]-piperazine-1-carbonyl}-2-[4-(3-bromo-4-hydroxy-phenoxy)-3,5-dimethyl-phenyl]-2H-[1,2,4]triazine-3,5-dione MS Calc.: 717.1; Found: 716.2 (M−1).

EXAMPLE 18-146

6-(4-Benzyl-piperazine-1-carbonyl)-2-[4-(3-bromo-4-hydroxy-phenoxy)-3,5-dimethyl-phenyl]-2H-[1,2,4]triazine-3,5-dione MS Calc.: 605.1; Found: 604.2 (M−1).

EXAMPLE 18-147

2-[4-(6-Hydroxy-biphenyl-3-yloxy)-3,5-dimethyl-phenyl]-2H-[1,2,4]triazine-3,5-dione MS Calc.: 401.1; Found: 402.0 (M+1).

EXAMPLE 19

2-[4-(3-Bromo-4-methoxy-phenoxy)-3,5-dimethyl-phenyl]-3,5-dioxo-2,3,4,5-tetrahydro-[1,2,4]triazine-6-carboxylic acid cyclohexylmethyl ester To a solution of cyclohexylmethanol (9 μmol) in DMF were added sequentially solutions of 2-[4-(3-bromo-4-methoxy-phenoxy)-3,5-dimethyl-phenyl]-3,5-dioxo-2,3,4,5-tetrahydro-[1,2,4]triazine-6-carboxylic acid (5 μmol), diisopropylcarbodiimide (10 mmol) and 4-dimethylaminopyridine (10 μmol). The resulting soution was shaken at 50° C. for 18 h. HPLC and LCMS shows the starting material to be consumed and the desired product present. MS Calc.: 557.1; Found: 556.1 (M−1).

Using the appropriate starting materials, EXAMPLES 19-1 to 19-81 were prepared in an analogous manner to that described in EXAMPLE 19.

EXAMPLE 19-1

2-[4-(3-Bromo-4-methoxy-phenoxy)-3,5-dimethyl-phenyl]-3,5-dioxo-2,3,4,5-tetrahydro-[1,2,4]triazine-6-carboxylic acid biphenyl-2-ylmethyl ester MS Calc.: 627.1; Found: 626.1 (M−1).

EXAMPLE 19-2

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-ethoxy-propyl ester MS Calc.: 547.1; Found: 545.9 (M−1).

EXAMPLE 19-3

2-[4-(3-Bromo-4-methoxy-phenoxy)-3,5-dimethyl-phenyl]-3,5-dioxo-2,3,4,5-tetrahydro-[1,2,4]triazine-6-carboxylic acid isobutyl ester MS Calc.: 517.1; Found: 515.9 (M−1).

EXAMPLE 19-4

2-[4-(3-Bromo-4-methoxy-phenoxy)-3,5-dimethyl-phenyl]-3,5-dioxo-2,3,4,5-tetrahydro-[1,2,4]triazine-6-carboxylic acid decyl ester MS Calc.: 601.2; Found: 600.1 (M−1).

EXAMPLE 19-5

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,4-dimethoxy-benzyl ester MS Calc.: 611.1; Found: 610.0 (M−1).

EXAMPLE 19-6

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-oxo-2-phenyl-ethyl ester MS Calc.: 579.1; Found: 578.0 (M−1).

EXAMPLE 19-7

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2,2,2-trifluoro-ethyl ester MS Calc.: 543.0; Found: 541.9 (M−1).

EXAMPLE 19-8

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-cyano-ethyl ester MS Calc.: 514.0; Found: 512.8 (M−1).

EXAMPLE 19-9

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-chloro-benzyl ester MS Calc.: 585.0; Found: 584.0 (M−1).

EXAMPLE 19-10

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-dimethylamino-ethyl ester MS Calc.: 532.1; Found: 530.9 (M−1).

EXAMPLE 19-11

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(ethyl-phenyl-amino)-ethyl ester MS Calc.: 608.1; Found: 606.9 (M−1).

EXAMPLE 19-12

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-phenoxy-ethyl ester MS Calc.: 581.1; Found: 580.0 (M−1).

EXAMPLE 19-13

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-acetoxy-ethyl ester MS Calc.: 547.1; Found: 545.9 (M−1).

EXAMPLE 19-14

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(2-chloro-ethoxy)-ethyl ester MS Calc.: 567.0; Found: 566.0 (M−1).

EXAMPLE 19-15

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(2-methoxy-ethoxy)-ethyl ester MS Calc.: 563.1; Found: 562.0 (M−1).

EXAMPLE 19-16

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,7-dimethyl-octa-2,6-dienyl ester MS Calc.: 597.1; Found: 596.1 (M−1).

EXAMPLE 19-17

2-[4-(3-Bromo-4-methoxy-phenoxy)-3,5-dimethyl-phenyl]-3,5-dioxo-2,3,4,5-tetrahydro-[1,2,4]triazine-6-carboxylic acid allyl ester MS Calc.: 501.1; Found: 500.0 (M−1).

EXAMPLE 19-18

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-dimethylamino-propyl ester MS Calc.: 546.1; Found: 545.0 (M−1).

EXAMPLE 19-19

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4-oxo-pentyl ester MS Calc.: 545.1; Found: 543.9 (M−1).

EXAMPLE 19-20

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4-chloro-butyl ester MS Calc.: 551.0; Found: 550.0 (M−1).

EXAMPLE 19-21

2-[4-(3-Bromo-4-methoxy-phenoxy)-3,5-dimethyl-phenyl]-3,5-dioxo-2,3,4,5-tetrahydro-[1,2,4]triazine-6-carboxylic acid tetrahydro-furan-2-ylmethyl ester MS Calc.: 545.1; Found: 543.9 (M−1).

EXAMPLE 19-22

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4-nitro-benzyl ester MS Calc.: 596.1; Found: 594.8 (M−1).

EXAMPLE 19-23

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-phenyl-propyl ester MS Calc.: 579.1; Found: 578.0 (M−1).

EXAMPLE 19-24

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(4-tert-butyl-phenoxy)-ethyl ester MS Calc.: 637.1; Found: 636.1 (M−1).

EXAMPLE 19-25

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(4-dimethylamino-phenyl)-2-oxo-1-phenyl-ethyl ester MS Calc.: 698.1; Found: 696.9 (M−1).

EXAMPLE 19-26

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(4-methyl-thiazol-5-yl)-ethyl ester MS Calc.: 586.1; Found: 585.0 (M−1).

EXAMPLE 19-27

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-morpholin-4-yl-ethyl ester MS Calc.: 574.1; Found: 573.0 (M−1).

EXAMPLE 19-28

2-[4-(3-Bromo-4-methoxy-phenoxy)-3,5-dimethyl-phenyl]-3,5-dioxo-2,3,4,5-tetrahydro-[1,2,4]triazine-6-carboxylic acid pyridin-4-ylmethyl ester MS Calc.: 552.1; Found: 551.0 (M−1).

EXAMPLE 19-29

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-methyl-isoxazol-5-ylmethyl ester MS Calc.: 556.1; Found: 555.0 (M−1).

EXAMPLE 19-30

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(6,6-dimethyl-bicyclo[3.1.1]hept-2-en-2-yl)-ethyl ester MS Calc.: 609.1; Found: 608.0 (M−1).

EXAMPLE 19-31

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,4,5-trimethoxy-benzyl ester MS Calc.: 641.1; Found: 640.0 (M−1).

EXAMPLE 19-32

2-[4-(3-Bromo-4-methoxy-phenoxy)-3,5-dimethyl-phenyl]-3,5-dioxo-2,3,4,5-tetrahydro-[1,2,4]triazine-6-carboxylic acid ethoxycarbonylmethyl ester MS Calc.: 547.1; Found: 546.1 (M−1).

EXAMPLE 19-33

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-oxo-propyl ester MS Calc.: 517.0; Found: 515.8 (M−1).

EXAMPLE 19-34

2-[4-(3-Bromo-4-methoxy-phenoxy)-3,5-dimethyl-phenyl]-3,5-dioxo-2,3,4,5-tetrahydro-[1,2,4]triazine-6-carboxylic acid [1,3]dioxan-5-yl ester MS Calc.: 547.1; Found: 546.1 (M−1).

EXAMPLE 19-35

2-[4-(3-Bromo-4-methoxy-phenoxy)-3,5-dimethyl-phenyl]-3,5-dioxo-2,3,4,5-tetrahydro-[1,2,4]triazine-6-carboxylic acid pyridin-2-ylmethyl ester MS Calc.: 552.1; Found: 551.0 (M−1).

EXAMPLE 19-36

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2,3-dihydro-benzo[1,4]dioxin-2-ylmethyl ester MS Calc.: 609.1; Found: 608.0 (M−1).

EXAMPLE 19-37

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-chloro-benzyl ester MS Calc.: 585.0; Found: 583.9 (M−1).

EXAMPLE 19-38

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-isopropoxy-ethyl ester MS Calc.: 547.1; Found: 545.9 (M−1).

EXAMPLE 19-39

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-phenylsulfanyl-ethyl ester MS Calc.: 597.1; Found: 595.9 (M−1).

EXAMPLE 19-40

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-butylsulfanyl-ethyl ester MS Calc.: 577.1; Found: 576.0 (M−1).

EXAMPLE 19-41

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-methyl-allyl ester MS Calc.: 515.1; Found: 514.0 (M−1).

EXAMPLE 19-42

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-methoxy-butyl ester MS Calc.: 547.1; Found: 545.9 (M−1).

EXAMPLE 19-43

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-methylsulfanyl-propyl ester MS Calc.: 549.1; Found: 548.0 (M−1).

EXAMPLE 19-44

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-chloro-4-nitro-benzyl ester MS Calc.: 630.0; Found: 629.0 (M−1).

EXAMPLE 19-45

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-pyridin-2-yl-propyl ester MS Calc.: 580.1; Found: 579.0 (M−1).

EXAMPLE 19-46

2-[4-(3-Bromo-4-methoxy-phenoxy)-3,5-dimethyl-phenyl]-3,5-dioxo-2,3,4,5-tetrahydro-[1,2,4]triazine-6-carboxylic acid benzo[1,3]dioxol-5-ylmethyl ester MS Calc.: 595.1; Found: 594.0 (M−1).

EXAMPLE 19-47

2-[4-(3-Bromo-4-methoxy-phenoxy)-3,5-dimethyl-phenyl]-3,5-dioxo-2,3,4,5-tetrahydro-[1,2,4]triazine-6-carboxylic acid pent-4-enyl ester MS Calc.: 529.1; Found: 527.9 (M−1).

EXAMPLE 19-48

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-[4-(4-acetyl-phenyl)-piperazin-1-yl]-ethyl ester MS Calc.: 691.2; Found: 690.0 (M−1).

EXAMPLE 19-49

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(2-methylsulfanyl-4,5-dihydro-imidazol-1-yl)-ethyl ester MS Calc.: 603.1; Found: 605.4.

EXAMPLE 19-50

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,3-dimethyl-butyl ester MS Calc.: 545.1; Found: 544.0 (M−1).

EXAMPLE 19-51

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2,3-dimethoxy-benzyl ester MS Calc.: 611.1; Found: 609.9 (M−1).

EXAMPLE 19-52

2-[4-(3-Bromo-4-methoxy-phenoxy)-3,5-dimethyl-phenyl]-3,5-dioxo-2,3,4,5-tetrahydro-[1,2,4]triazine-6-carboxylic acid biphenyl-4-ylmethyl ester MS Calc.: 627.1; Found: 626.1 (M−1).

EXAMPLE 19-53

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-(4-chloro-phenoxy)-ethyl ester MS Calc.: 615.0; Found: 614.0 (M−1).

EXAMPLE 19-54

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3-phenyl-allyl ester MS Calc.: 577.1; Found: 576.0 (M−1).

EXAMPLE 19-55

2-[4-(3-Bromo-4-methoxy-phenoxy)-3,5-dimethyl-phenyl]-3,5-dioxo-2,3,4,5-tetrahydro-[1,2,4]triazine-6-carboxylic acid pyridin-3-ylmethyl ester MS Calc.: 552.1; Found: 551.0 (M−1).

EXAMPLE 19-56

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-cyclohexyl-ethyl ester MS Calc.: 571.1; Found: 570.0 (M−1).

EXAMPLE 19-57

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-thiophen-2-yl-ethyl ester MS Calc.: 571.0; Found: 570.0 (M−1).

EXAMPLE 19-58

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-adamantan-1-yl-ethyl ester MS Calc.: 623.2; Found: 622.1 (M−1).

EXAMPLE 19-59

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-bromo-1-bromomethyl-ethyl ester MS Calc.: 658.9; Found: 659.9 (M−1).

EXAMPLE 19-60

2-[4-(3-Bromo-4-methoxy-phenoxy)-3,5-dimethyl-phenyl]-3,5-dioxo-2,3,4,5-tetrahydro-[1,2,4]triazine-6-carboxylic acid cycloheptyl ester MS Calc.: 557.1; Found: 556.1 (M−1).

EXAMPLE 19-61

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-methyl-piperidin-4-yl ester MS Calc.: 558.1; Found: 557.0 (M−1).

EXAMPLE 19-62

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1,2-bis-(4-methoxy-phenyl)-2-oxo-ethyl ester MS Calc.: 715.1; Found: 714.0 (M−1).

EXAMPLE 19-63

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-chloromethyl-2-isopropoxy-ethyl ester MS Calc.: 595.1; Found: 594.0 (M−1).

EXAMPLE 19-64

2-[4-(3-Bromo-4-methoxy-phenoxy)-3,5-dimethyl-phenyl]-3,5-dioxo-2,3,4,5-tetrahydro-[1,2,4]triazine-6-carboxylic acid 4,4-dimethyl-2-oxo-tetrahydro-furan-3-yl ester MS Calc.: 573.1; Found: 571.9 (M−1).

EXAMPLE 19-65

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-bromo-indan-1-yl ester MS Calc.: 655.0; Found: 653.8 (M−1).

EXAMPLE 19-66

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-chloro-1-methyl-ethyl ester MS Calc.: 537.0; Found: 536.0 (M−1).

EXAMPLE 19-67

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-ethoxycarbonyl-ethyl ester MS Calc.: 561.1; Found: 559.9 (M−1).

EXAMPLE 19-68

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-methoxy-1-methyl-ethyl ester MS Calc.: 533.1; Found: 532.0 (M−1).

EXAMPLE 19-69

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-ethyl-propyl ester MS Calc.: 531.1; Found: 530.0 (M−1).

EXAMPLE 19-70

2-[4-(3-Bromo-4-methoxy-phenoxy)-3,5-dimethyl-phenyl]-3,5-dioxo-2,3,4,5-tetrahydro-[1,2,4]triazine-6-carboxylic acid tetrahydro-furan-3-yl ester MS Calc.: 531.1; Found: 530.0 (M−1).

EXAMPLE 19-71

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-methyl-hexyl ester MS Calc.: 559.1; Found: 557.9 (M−1).

EXAMPLE 19-72

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1-cyclopentyl-ethyl ester MS Calc.: 557.1; Found: 556.0 (M−1).

EXAMPLE 19-73

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2,5-dimethyl-cyclohexyl ester MS Calc.: 571.1; Found: 570.1 (M−1).

EXAMPLE 19-74

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,4-dimethyl-cyclohexyl ester MS Calc.: 571.1; Found: 570.1 (M−1).

EXAMPLE 19-75

2-[4-(3-Bromo-4-methoxy-phenoxy)-3,5-dimethyl-phenyl]-3,5-dioxo-2,3,4,5-tetrahydro-[1,2,4]triazine-6-carboxylic acid 3,5-dimethyl-cyclohexyl ester MS Calc.: 571.1; Found: 570.1 (M−1).

EXAMPLE 19-76

2-[4-(3-Bromo-4-methoxy-phenoxy)-3,5-dimethyl-phenyl]-3,5-dioxo-2,3,4,5-tetrahydro-[1,2,4]triazine-6-carboxylic acid 2-ethoxycarbonyl-1-methyl-ethyl ester MS Calc.: 575.1; Found: 574.0 (M−1).

EXAMPLE 19-77

2-[4-(3-Bromo-4-methoxy-phenoxy)-3,5-dimethyl-phenyl]-3,5-dioxo-2,3,4,5-tetrahydro-[1,2,4]triazine-6-carboxylic acid bicyclohexyl-4-yl ester MS Calc.: 625.2; Found: 624.1 (M−1).

EXAMPLE 19-78

2-[4-(3-Bromo-4-methoxy-phenoxy)-3,5-dimethyl-phenyl]-3,5-dioxo-2,3,4,5-tetrahydro-[1,2,4]triazine-6-carboxylic acid 9H-fluoren-9-yl ester MS Calc.: 625.1; Found: 624.0 (M−1).

EXAMPLE 19-79

2-[4-(3-Bromo-4-methoxy-phenoxy)-3,5-dimethyl-phenyl]-3,5-dioxo-2,3,4,5-tetrahydro-[1,2,4]triazine-6-carboxylic acid 1,7,7-trimethyl-bicyclo[2.2.1]hept-2-yl ester MS Calc.: 597.1; Found: 595.9 (M−1).

EXAMPLE 19-80

2-[4-(3-Bromo-4-methoxy-phenoxy)-3,5-dimethyl-phenyl]-3,5-dioxo-2,3,4,5-tetrahydro-[1,2,4]triazine-6-carboxylic acid bicyclo[2.2.1]hept-2-yl ester MS Calc.: 555.1; Found: 554.0 (M−1).

EXAMPLE 19-81

2-[4-(3-Bromo-4-hydroxy-phenoxy)-3,5-dimethyl-phenyl]-3,5-dioxo-2,3,4,5-tetrahydro-[1,2,4]triazine-6-carboxylic acid MS Calc.: 447.0; Found: 446.1 (M−1).

EXAMPLE 20

2-{4-[3-(4-Fluoro-benzoyl)-4-methoxy-phenoxy]-3,5-dimethyl-phenyl}-4-methyl-2H-[1,2,4]triazine-3,5-dione To a stirred solution of 2-{4-[3-4-fluoro-benzoyl)-4-methoxy-phenoxy]-3,5-dimethyl-phenyl}-2H-[1,2,4]triazine-3,5-dione (50 mg) and potassium hydroxide (12 mg) in methanol (2 mL) was added dimethylsulfate (41 mg) to produce a thick slurry. After 3 h, the reaction mixture was diluted into ethyl acetate, washed with 1N aqueous sodium hydroxide, the organic layer dried over sodium sulfate, filtered and concentrated in vacuo. The resulting oil was flash chromatographed on silica gel (20%–35% ethyl acetate/hexanes) to afford the title compound of this EXAMPLE as a colorless solid, 24 mg. MS Calc.:475.5 Found:476.2 (M+1).

Using the appropriate starting materials, EXAMPLES 21-1 to 21-9 are prepared by the methods described in Scheme D-1 above:

EXAMPLE 21-1

2-[3-Chloro-4-(3-cyclobutylmethanesulfonyl-4-hydroxy-phenoxy)-5-methyl-phenyl]-2H-[1,2,4]triazine-3,5-dione

EXAMPLE 21-2

2-[3,5-Dichloro-4-(3-cyclobutylmethanesulfonyl-4-hydroxy-phenoxy)-phenyl]-2H-[1,2,4]triazine-3,5-dione

EXAMPLE 21-3

2-[3,5-Dimethyl-4-(3-cyclobutylmethanesulfonyl-4-hydroxy-phenoxy)-phenyl]-2H-[1,2,4]triazine-3,5-dione

EXAMPLE 21-4

2-[3-Chloro-4-(3-cyclopentylmethanesulfonyl-4-hydroxy-phenoxy)-5-methyl-phenyl]-2H-[1,2,4]triazine-3,5-dione

EXAMPLE 21-5

2-[3,5-Dichloro-4-(3-cyclopentylmethanesulfonyl-4-hydroxy-phenoxy)-phenyl]-2H-[1,2,4]triazine-3,5-dione

EXAMPLE 21-6

2-[3,5-Dimethyl-4-(3-cyclopentylmethanesulfonyl-4-hydroxy-phenoxy)-phenyl]-2H-[1,2,4]triazine-3,5-dione

EXAMPLE 21-7

2-[3-Chloro-4-(3-cyclohexylmethanesulfonyl-4-hydroxy-phenoxy)-5-methyl-phenyl]-2H-[1,2,4]triazine-3,5-dione

EXAMPLE 21-8

2-[3,5-Dichloro-4-(3-cyclohexylmethanesulfonyl-4-hydroxy-phenoxy)-phenyl]-2H-[1,2,4]triazine-3,5-dione

EXAMPLE 21-9

2-[3,5-Dimethyl-4-(3-cyclohexylmethanesulfonyl-4-hydroxy-phenoxy)-phenyl]-2H-[1,2,4]triazine-3,5-dione

What is claimed is:

1. A compound of the formula:

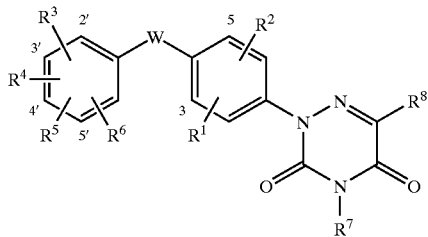

(I)

or a pharmaceutically acceptable salt of said compound, in which:

W is —O—, $R^1$ is located at the 3-position and is selected from methyl, bromo, or chloro, $R^2$ is located at the 5-position and is selected from methyl, bromo, or chioro, $R^3$ is located at the 2' position and is represented by hydrogen, $R^4$ is located at the 3' position and is represented by —C($R^{14}$)($R^{15}$)($R^{16}$), $R^5$ is located at the 4' position and is represented by hydroxy or methoxy, $R^6$ is located at the 5' position and is represented by hydrogen, $R^7$ is hydrogen, $R^8$ is hydrogen, $R^{14}$ is hydrogen, or —($C_1$–$C_6$)alkyl, $R^{15}$ is hydrogen or —($C_1$–$C_6$)alkyl, $R^{16}$ is —($C_0$–$C_6$)alkyl-aryl, aryl is (a) phenyl optionally substituted with one or mare substituents independently selected from Group Z; (b) naphthyl optionally substituted with one, or more substituents independently selected from Group Z or (c) biphenyl optionally substituted with one or more substituents independently selected from Group Z, and;

Group Z, for each occurrence, is independently selected from the group consisting of (a) hydrogen, (b) halogen, (c) trifluoromethyl, (d) hydroxy, (e) —$OCF_3$, (f) —CN, (g) —$NO_2$, and (h) —($C_1$–$C_6$)alkyl.

2. A compound according to claim 1 in which $R^1$ and $R^2$ are each methyl.

3. A compound according to claim 1 in which $R^5$ is hydroxy.

4. A compound according to claim 1 in which $R^{16}$ is ($C_1$)alkyl-aryl.

5. A compound according to claim 4 in which aryl is phenyl, optionally substituted with one or more substituents independently selected from Group Z.

6. A compound according to claim 1 selected from the group consisting of:

i) 2-{3-chloro-4-[3-(4-fluoro-benzyl)-4-hydroxy-phenoxy]-5-methyl-phenyl}-2H[1,2,4]triazine-3,5-dione;

ii) 2-{4-[3-(4-fluoro-benzyl)-4-methoxy-phenoxy]-3,5-dimethyl-phenyl}-2H-[1,2,4]triazine-3,5-dione;

iii) 2-(4-{3-[(4-fluoro-phenyl)-hydroxy-methyl]-4-hydroxy-phenoxy}-3,5-dimethyl-phenyl)-2H-[1,2,4]triazine-3,5-dione;

iv) 2-{4-[3-(4-fluoro-benzyl)-4-hydroxy-phenoxy]-3,6-dimethyl-phenyl}-2H-[1,2,4]triazine-3,5-dione v) 2-{3,5-dichloro-4-[3-(4-fluoro-benzyl)-4-hydroxy-phenoxy]-phenyl}-2H-[1,2,4]triazine-3,5-dione, and;

vi) 2-{3,5-dibromo-4-[3-(4-fluoro-benzyl)-4-hydroxy-phenoxy]-phenyl}-2H-[1,2,4]triazine-3,5-dione.

7. A pharmaceutical composition comprising an effective amount of a compound of claim 5 or a pharmaceutically acceptable salt of said compound, in admixture with a pharmaceutically acceptable carrier.

8. 2-{4-[3-(4-Fluoro-benzyl)-4-hydroxy-phenoxy]-3,5-dimethyl-phenyl}-2H-[1,2,4]triazine-3,5-dione, or a pharmaceutically acceptable salt of said compound.

9. A topical pharmaceutical composition comprising an effective amount of a compound of claim 8, in admixture with a pharmaceutically acceptable topical carrier.

* * * * *